United States Patent
Antle et al.

(10) Patent No.: US 11,795,241 B2
(45) Date of Patent: Oct. 24, 2023

(54) FRACTIONATED ALKYLATED CYCLODEXTRIN COMPOSITIONS AND PROCESSES FOR PREPARING AND USING THE SAME

(71) Applicant: CyDex Pharmaceuticals, Inc., San Diego, CA (US)

(72) Inventors: Vincent D. Antle, Olathe, KS (US); Charles Alan Watson, Louisburg, KS (US); David W. Miles, Kansas City, MO (US)

(73) Assignee: CyDex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 17/103,328

(22) Filed: Nov. 24, 2020

(65) Prior Publication Data

US 2021/0147582 A1    May 20, 2021

Related U.S. Application Data

(63) Continuation of application No. 15/505,428, filed as application No. PCT/US2015/046408 on Aug. 21, 2015, now Pat. No. 10,851,184.

(60) Provisional application No. 62/040,568, filed on Aug. 22, 2014.

(51) Int. Cl.
| | | |
|---|---|---|
| *C08B 37/00* | (2006.01) | |
| *B01D 15/32* | (2006.01) | |
| *C08L 5/16* | (2006.01) | |
| *C08B 37/16* | (2006.01) | |
| *A61K 47/69* | (2017.01) | |
| *A61K 47/40* | (2006.01) | |

(52) U.S. Cl.
CPC .......... *C08B 37/0006* (2013.01); *A61K 47/40* (2013.01); *A61K 47/6951* (2017.08); *B01D 15/325* (2013.01); *C08B 37/0003* (2013.01); *C08B 37/0012* (2013.01); *C08L 5/16* (2013.01)

(58) Field of Classification Search
CPC ............ C08B 37/0003; C08B 37/0012; B01D 15/32–38
See application file for complete search history.

(56) References Cited

U.S. PATENT DOCUMENTS

| | | |
|---|---|---|
| 2,744,938 A | 7/1952 | Urban |
| 3,033,900 A | 5/1962 | Holstein |
| 3,426,011 A | 2/1969 | Parmerter et al. |
| 3,453,257 A | 7/1969 | Parmerter et al. |
| 3,453,259 A | 7/1969 | Parmerter et al. |
| 3,459,731 A | 8/1969 | Gramera et al. |
| 4,317,881 A | 3/1982 | Yagi et al. |
| 4,477,568 A | 10/1984 | Hokse et al. |
| 4,597,946 A | 7/1986 | Ward |
| 4,658,058 A | 4/1987 | Umezawa et al. |
| 4,727,064 A | 2/1988 | Pitha |
| 4,738,923 A | 4/1988 | Ammeraal |
| 4,835,105 A | 5/1989 | Seres |
| 4,904,306 A | 2/1990 | Ammeraal |
| 4,920,214 A | 4/1990 | Friedman |
| 5,007,967 A | 4/1991 | Ammeraal |
| 5,019,562 A | 5/1991 | Folkman |
| 5,134,127 A | 7/1992 | Stella et al. |
| 5,135,919 A | 8/1992 | Folkman |
| 5,173,481 A | 12/1992 | Pitha et al. |
| 5,183,809 A | 2/1993 | Weisz et al. |
| 5,241,059 A | 8/1993 | Yoshinaga |
| 5,257,985 A | 11/1993 | Puhl |
| 5,324,718 A | 6/1994 | Loftsson |
| 5,376,537 A | 12/1994 | Cami et al. |
| 5,376,645 A | 12/1994 | Stella et al. |
| 5,393,880 A | 2/1995 | Shieh et al. |
| 5,472,954 A | 12/1995 | Loftsson |
| 5,479,254 A | 12/1995 | Woskov et al. |
| 5,512,665 A | 4/1996 | Uchiyama et al. |
| 5,536,826 A | 7/1996 | Hirsenkorn |
| 5,550,222 A | 8/1996 | Shieh |
| 5,569,756 A | 10/1996 | Qi et al. |
| 5,578,719 A | 11/1996 | Gadelle et al. |
| 5,594,125 A | 1/1997 | Seyschab |
| 5,620,872 A | 4/1997 | Shieh et al. |
| 5,658,390 A | 8/1997 | Shieh et al. |
| 5,658,894 A | 8/1997 | Weisz et al. |
| 5,661,151 A | 8/1997 | Saksena et al. |
| 5,710,268 A | 1/1998 | Wimmer |
| 5,756,484 A | 5/1998 | Fuertes et al. |
| 5,760,015 A | 6/1998 | Joullie et al. |

(Continued)

FOREIGN PATENT DOCUMENTS

| | | |
|---|---|---|
| CN | 102040675 | 5/2011 |
| CN | 104892797 | 9/2015 |

(Continued)

OTHER PUBLICATIONS

Bansal, P. et al "Regioselective alkylation of beta-cyclodextrins" Australian J. Chem., ovl 51, iss. 10, pp. 915-923. (abstract only) (Year: 1998).*
Boger, J. et al "Cyclodextrin chemistry . . . " Helv. Chim. Acta, vol. 61, pp. 2190-2218. (Year: 1978).*
Jindrich, J. et al "Separation of cyclodextrins and their derivatives . . . " Carbohyd. Res., vol. 275, pp. 1-7. (Year: 1995).*
Welch, C. et al "Microscale HPLC predicts preparative performance . . . " Org. Proc. Res. Dev., vol. 12, pp. 674-677. (Year: 2008).*
U.S. Appl. No. 60/133,847, filed May 12, 1999, Crews et al.
Adam et al., 2002, Cyclodextrin-derived host molecules as reversal agents for the neuromuscular blocker rocuronium bromide: synthesis and structure-activity relationships, J. Med. Chem. 45:1806-1816.

(Continued)

*Primary Examiner* — Leigh C Maier
(74) *Attorney, Agent, or Firm* — Knobbe, Martens, Olson & Bear LLP

(57) ABSTRACT

The present invention relates to compositions comprising fractionated alkylated cyclodextrin compositions having a single degree of substitution, and processes for preparing and using the same.

8 Claims, 6 Drawing Sheets

(56) References Cited

U.S. PATENT DOCUMENTS

| | | | |
|---|---|---|---|
| 5,831,081 | A | 11/1998 | Reuscher |
| 5,846,954 | A | 12/1998 | Joullie et al. |
| 5,874,418 | A | 2/1999 | Stella et al. |
| 5,914,122 | A | 6/1999 | Otterbeck et al. |
| 5,935,941 | A | 8/1999 | Pitha |
| 6,033,573 | A | 3/2000 | Toles et al. |
| 6,046,177 | A | 4/2000 | Stella et al. |
| 6,133,248 | A | 10/2000 | Stella |
| 6,153,746 | A | 11/2000 | Shah et al. |
| 6,235,505 | B1 | 5/2001 | Grull et al. |
| 6,267,979 | B1 | 7/2001 | Raad et al. |
| 6,316,613 | B1 | 11/2001 | Chen et al. |
| 6,337,302 | B1 | 1/2002 | Teng et al. |
| 6,391,862 | B1 | 5/2002 | Vigh |
| 6,407,079 | B1 | 6/2002 | Muller et al. |
| 6,479,467 | B1 | 11/2002 | Buchanan et al. |
| 6,509,319 | B1 | 1/2003 | Issam |
| 6,524,595 | B1 | 2/2003 | Perrier et al. |
| 6,610,671 | B2 | 8/2003 | Buchanan et al. |
| 6,670,340 | B1 | 12/2003 | Zhang et al. |
| 6,831,099 | B1 | 12/2004 | Crews |
| 6,869,939 | B2 | 3/2005 | Mosher et al. |
| 7,034,013 | B2 | 4/2006 | Thompson et al. |
| 7,582,758 | B2 | 9/2009 | Martin |
| 7,625,878 | B2 | 12/2009 | Stella et al. |
| 7,629,331 | B2 | 12/2009 | Pipkin et al. |
| 7,635,773 | B2 | 12/2009 | Antle |
| 8,114,438 | B2 | 2/2012 | Pipkin et al. |
| 8,236,782 | B2 | 8/2012 | Mosher et al. |
| 8,278,437 | B2 | 10/2012 | Ren et al. |
| 8,410,077 | B2 | 4/2013 | Antle |
| 8,492,538 | B1 | 7/2013 | Matos |
| 9,200,088 | B2 | 12/2015 | Antle |
| 9,493,582 | B2 | 11/2016 | Antle et al. |
| 9,750,822 | B2 | 9/2017 | Antle |
| 9,751,957 | B2 | 9/2017 | Antle et al. |
| 10,040,872 | B2 | 8/2018 | Antle et al. |
| 10,117,951 | B2 | 11/2018 | Antle |
| 10,323,103 | B2 | 6/2019 | Antle et al. |
| 10,633,462 | B2 | 4/2020 | Antle et al. |
| 10,780,177 | B2 | 9/2020 | Antle et al. |
| 10,800,861 | B2 | 10/2020 | Antle et al. |
| 10,851,184 | B2 | 12/2020 | Antle et al. |
| 2003/0055023 | A1 | 3/2003 | Rajewski |
| 2005/0164986 | A1 | 7/2005 | Mosher et al. |
| 2005/0186267 | A1 | 8/2005 | Thompson et al. |
| 2005/0250738 | A1 | 11/2005 | Mosher et al. |
| 2006/0009469 | A1 | 1/2006 | Witchey |
| 2006/0045850 | A1 | 3/2006 | Namburi |
| 2006/0128611 | A1 | 6/2006 | Lewis et al. |
| 2006/0258537 | A1 | 11/2006 | Stella et al. |
| 2007/0020196 | A1 | 1/2007 | Pipkin et al. |
| 2007/0020298 | A1 | 1/2007 | Pipkin et al. |
| 2007/0020299 | A1 | 1/2007 | Pipkin et al. |
| 2007/0082870 | A1 | 4/2007 | Buchanan |
| 2007/0175472 | A1 | 8/2007 | Pipkin et al. |
| 2007/0202054 | A1 | 8/2007 | Pipkin et al. |
| 2008/0194519 | A1 | 8/2008 | Cloyd |
| 2009/0011037 | A1 | 1/2009 | Pipkin et al. |
| 2009/0012042 | A1 | 1/2009 | Ren et al. |
| 2009/0123540 | A1 | 5/2009 | Pipkin et al. |
| 2009/0239942 | A1 | 9/2009 | Cloyd |
| 2009/0270348 | A1 | 10/2009 | Antle |
| 2010/0093663 | A1 | 4/2010 | Antle |
| 2010/0292268 | A1 | 7/2010 | Mosher et al. |
| 2010/0311838 | A1 | 12/2010 | Pipkin et al. |
| 2012/0021013 | A1 | 1/2012 | Esaki |
| 2012/0136072 | A1 | 5/2012 | Mosher et al. |
| 2013/0331356 | A1 | 12/2013 | Olhava et al. |
| 2014/0046061 | A1 | 2/2014 | Matos |
| 2020/0157252 | A1 | 5/2020 | Antle et al. |

FOREIGN PATENT DOCUMENTS

| | | |
|---|---|---|
| CN | 104974275 | 10/2015 |
| EP | 0 579 435 | 1/1994 |
| EP | 0 274 259 | 2/1994 |
| EP | 1 067 143 | 1/2001 |
| EP | 1 950 227 | 7/2008 |
| EP | 2 018 866 | 1/2009 |
| EP | 2 261 236 | 7/2015 |
| JP | 04-57801 | 2/1992 |
| JP | 05-001102 | 1/1993 |
| JP | 05-504783 | 7/1993 |
| JP | 07-149801 | 6/1995 |
| JP | 07-216002 | 8/1995 |
| JP | 10-504351 | 4/1998 |
| JP | 2001-31703 | 2/2001 |
| WO | WO 90/012035 | 10/1990 |
| WO | WO 91/11172 | 8/1991 |
| WO | WO 99/27932 | 6/1999 |
| WO | WO 99/42111 | 8/1999 |
| WO | WO 01/01955 | 1/2001 |
| WO | WO 01/40316 | 6/2001 |
| WO | WO 02/055562 | 7/2002 |
| WO | WO 04/064787 | 8/2004 |
| WO | WO 04/064788 | 8/2004 |
| WO | WO 05/042584 | 5/2005 |
| WO | WO 05/118277 | 5/2005 |
| WO | WO 05/111008 | 11/2005 |
| WO | WO 06/017842 | 2/2006 |
| WO | WO 06/071491 | 7/2006 |
| WO | WO 08/005053 | 1/2008 |
| WO | WO 08/005691 | 1/2008 |
| WO | WO 08/005692 | 1/2008 |
| WO | WO 08/005802 | 1/2008 |
| WO | WO 08/005819 | 1/2008 |
| WO | WO 08/034040 | 3/2008 |
| WO | WO 08/134600 | 11/2008 |
| WO | WO 08/134601 | 11/2008 |
| WO | WO 08/140782 | 11/2008 |
| WO | WO 09/018069 | 2/2009 |
| WO | WO 09/045497 | 4/2009 |
| WO | WO 09/129301 | 10/2009 |
| WO | WO 09/134347 | 11/2009 |
| WO | WO 10/053487 | 5/2010 |
| WO | WO 13/123254 | 8/2013 |
| WO | WO 13/130666 | 9/2013 |
| WO | WO 14/66274 | 5/2014 |

OTHER PUBLICATIONS

Adams, Julian, "Proteasome Inhibitors as Therapeutic Agents," *Expert Opinion Therapeutic Patents* (2003) 13(1), pp. 45-57.

Aldrich, "Activated Carbon," *Technical Information Bulletin, AL-143, Mineral Adsorbents, Filter Agents and Drying Agents*, Section III.

Armarego et al., "Common Physical Techniques in Purification," *Purification of Laboratory Chemicals Fifth Edition*, Butterworth-Heinemann an Imprint of Elsevier Science, © 2003, pp. 20 and 159.

Avis et al., Chapter 10, "Parenteral Medications," in Dispensing of Medication (Hoover ed., 8th ed.) (1976 Mack Publishing Co.).

Avis, Kenneth E., "Sterile Products," Chapter 22, in *The Theory and Practice of Industrial Pharmacy* (Lachman, Lieberman and Kanig eds., 3rd ed.) (1986 Lea & Fabiger; Fourth Indian Reprint 1991 Varghese Publishing House).

Baptista et al., 1996, Near-infrared detection of flow injection analysis by acoustooptic tunable filter-based spectrophotometry, Anal. Chem., 68(6):971-976.

Betadex, Jan.-Feb. 2008, Pharmacopeial Forum, The United States Pharmacopeial Convention, 34(1):127-130.

Blanchard et al., 1999, Some important considerations in the use of cyclodextrins, Pharmaceutical Research, 16(12):1796-1798.

Brewster et al., "Comparative interaction of 2-hydroxypropyl-B-cyclodextrin and sulfobutylether-β-cyclodextrin with itraconazole: Phase-solubility behavior and stabilization of supersaturated drug solutions," Eur. J. Pharm. Sci. 34 (2008) pp. 94-103.

Brustugun et al., "Formation and reactivity of free radicals in 5-hydroxymethyl-2-furaldehyde—the effect on isoprenaline photostabil-

(56) References Cited

OTHER PUBLICATIONS ity," *Journal of Photochemistry and Photobiology B: Biology*, 79 (2005) pp. 109-119.

Burdurlu et al., "Effect of storage on nonenzymatic browning of apple juice concentrates," *Food Chemistry*, 80 (2003) 91-97.

Canilha et al., "Eucalyptus hydrolysate detoxification with activated charcoal adsorption or ion-exchange resins for xylitol production," *Process Biochemistry*, 39 (2004) 1909-1912.

Carlson et al., "Effect of pH on Disintegration and Dissolution of Ketoconazole Tablets," *Am J Hosp Pharm. 1983*; 40:1334-1336.

Caturla et al., "Preparation of activated carbon by chemical activation with $ZnCl_2$," Carbon vol. 29, No. 7, pp. 999-1007, 1991.

Certificate of Analysis for Captisol® batch 17CX01.HQ00029 first sold on Feb. 6, 2007 and described in U.S. Pat. No. 7,635,773 (of record).

Certificate of Analysis for Captisol® batch 17CX01.HQ00038 first sold on May 5, 2009 and described in U.S. Pat. No. 7,635,773 (of record).

Certificate of Analysis for Captisol® batch 17CX01.HQ00044 first sold on Nov. 9, 2007 and described in U.S. Pat. No. 7,635,773 (of record).

Challa et al., "Cyclodextrins in Drug Delivery: An Updated Review," AAPS PharmSciTech 2005; 6 (2) Article 43, E329-E357.

ClinicalTrials.Gov, Feb. 21, 2011, Carfilzomib plus panobinostat in relapsed/refractory multiple myeloma (mm), NTC01301807, 8 pp.

Comprehensive Supramolecular Chemistry, vol. 3 Cyclodextrins, Szejtli et al., eds., Elsevier Science Inc., Tarrytown, NY, 1996.

Connors et al., eds., Chemical Stability of Pharmaceuticals, 1st Ed., John Wiley & Sons, New York, 1979, pp. 134-135.

Connors et al., eds., Chemical Stability of Pharmaceuticals, 2nd Ed., John Wiley & Sons, New York, 1986, pp. 564-565, 584-585, 770-771, 776-779.

Crowley et al., Drug-Excipient Interactions, Pharmaceutical Technology, Mar. 2001, pp. 1-6, Advanstar Publication.

Cyclodextrins in Pharmacy, Fromming et al., eds., Kluwer Academic Publishing, Dordrecht, Netherlands, 1994.

Darco G-60, "Does Your Application Require *Ultra* Pure Activated Carbon? Darco® G-60 is Your Answer," ICI Americas Inc., tech sheet. Chem. Eng. News, 1984, 62 (3), p. 5.

Demo et al., "Antitumor Activity of PR-171, a Novel Irreversible Inhibitor of the Proteasome," *Cancer Research* 2007; 67:(13), Jul. 1, 2007, pp. 6383-6391.

Elofsson et al., "Towards subunit-specific proteasome inhibitors: synthesis and evaluation of peptide $\alpha',\beta'$-epoxyketones," *Chemistry & Biology* 1999, vol. 6, No. 11, pp. 811-822.

Flynn, Gordon L. "Buffers-pH Control within Pharmaceutical Systems," *J. Parenteral Drug Assoc.*, Mar.-Apr. 1980 vol. 34, No. 2, pp. 139-162.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of $17\beta$-estradiol HP$\beta$CD sublingual tablets, Die Pharmazie, 51(1):39-42.

Fridriksdottir et al., Mar. 31-Apr. 2, 1996, Solubilization of $\beta$-cyclodextrin: the effect of polymers and various drugs on the solubility of $\beta$-cyclodextrin, Proceedings of the Eighth International Symposium on Cyclodextrins, eds. Szejtli et al., Budapest, 373-376.

Grard et al., "Analysis of sulfobutyl ether-$\beta$-cyclodextrin mixtures by ion-spray mass spectrometry and liquid chromotography-ion-spray mass spectrometry," J. Chromatography A, 925 (2001) pp. 79-87.

Grard et al., "Characterization of sulfobutyl ether-$\beta$-cyclodextrins mixtures by anion exchange chromatography using evaporative light scattering detection," *J. Chromatography A*, 897 (2000) pp. 185-193.

Grard et al., Sulfobutyl Ether-$\beta$-Cyclodextrin Fingerprint Using Ion Pair Reversed-Phase Chromatography, *Chromatographia*, vol. 50, No. 11, Dec. 12, 1999, pp. 695-700.

Greer et al., "Posaconazole (Noxafil): a new triazole antifungal agent," *Baylor University Medical Center Proceedings*, (2007) vol. 20, No. 2, pp. 188-196.

Guieu et al., 2008, Multiple homo- and hetero-functionalization of alpha-cyclodextrin, JOC, 72:2819-2828.

Hallal et al., "Electrochemical Polymerization of Furfural on a Platinum Electrode in Aqueous Solutions of Potassium Biphthalate," *Materials Research*, (2005) vol. 8, No. 1. pp. 23-29.

Hartman et al., 2011, Deciding whether to go with the flow: evaluating the merits of flow reactors for synthesis, Angew Chem Int Ed., 50:7502-7519.

Helbig, W.A., "Activated Carbon," *Journal of Chemical Education*, Feb. 1946, pp. 98-102.

Hewala et al., "Detection and determination of interfering 5-hydroxymethylfurfural in the analysis of caramel-coloured pharmaceutical syrups," *Journal of Clinical Pharmacy and Therapeutics*, (1993) 18:49-53.

Hughes et al., 2004, Array reactors for parallel synthesis, Journal of Combinatorial Chemistry, 6(3):308-311.

Ii et al., "Effect of renin inhibitor, ES-8891, on renal renin secretion and storage in the marmoset: comparison with captopril," *Journal of Hypertension*, 1991, vol. 9, No. 12, pp. 1119-1125.

Jacquet et al., 2004, Liquid chromatography analysis of monosubstituted sulfobutyl ether-$\beta$-cyclodextrin isomers on porous graphitic carbon, J. Sep. Sci. 27(14):1221-1228.

Jacquet et al., 2005, Characterization of a new methylated $\beta$-cyclodextrin with a low degree of substitution by matrix-assisted laser desorption/ionization mass spectrometry and liquid chromatography using evaporative light scattering detection, Journal of Chromatography A, 1083(1-2):106-112.

Johnson et al., "Solubilization of a Tripeptide HIV Protease Inhibitor Using a Combination of Ionization and Complexation with Chemically Modified Cyclodextrins," Journal of Pharmaceutical Sciences, vol. 83, No. 8, Aug. 1994, pp. 1142-1148.

Kageyama et al., "In Vitro Anti-Human Immunodeficiency Virus (HIV) Activites of Transition State Mimetic HIV Protease Inhibitors Containing Allophenylnorstatine," *Antimicrobial Agents and Chemotherapy*, Apr. 1993, vol. 37, No. 4, pp. 810-817.

Kauffman et al., "Zygomycosis: An Emerging Fungal Infection with New Options for Management," Invited Commentary, *Current Infectious Disease Reports*, 2007, 9(6):435-440.

Kisselev et al., Proteasome inhibitors: from research tools to drug candidates, *Chemistry & Biology*, 8 (2001) pp. 739-758.

Kokubu et al., "An Orally Active Inhibitor of Human Renin, ES-8891," *Cardiovascular Drug Reviews*, © 1991 Neva Press, Branford, CT, vol. 9, No. 1, pp. 49-58.

Kokubu et al., "ES-8891, An Orally Active Inhibitor of Human Renin," *Hypertension*, © 1990, 15, pp. 909-913.

Kraus et al., 2002, Per(6-amino-2-O-carboxymethyl-6-deoxy-3-)-methyl)-alpha-cyclodextrin: helical self-assembly of a polyionic amino acid into nanotubes, Angew. Chem. Int. Ed., 41(10):1715-1717.

Kristinsson et al., 1996, Dexamethasone-cyclodextrin-polymer co-complexes in aqueous eye drops, Investigative Ophthalmology & Visual Science, 37(6):1199-1203.

Kuhn et al., "Potent activity of carfilzomib, a novel, irreversible inhibitor of the ubiquitin-proteasome pathway, against preclinical models of multiple myeloma," *Blood*, Nov. 1, 2007, vol. 110, No. 9, pp. 3281-3290.

Lammers et al., 1971, Properties of cyclodextrins: Part VI. Water-soluble cyclodextrin-derivatives. Preparation and Analysis, Die Starke, 23(5):167-171.

Lammers et al., 1972, Properties of cyclodextrins, Part VIII Determination of the composition of inclusion complexes of hexane and 2,3-dimethylbutane with cyclodextrin derivatives in aqueous solution, Recl. Trav. Chim. Pays-Bas, 91(6):733-753.

Lima et al., "$\beta$-Cyclodextrin Production by Simultaneous Fermentation and Cyclization," *Applied Biochemistry Biotechnology*, vol. 70-72 (1998) pp. 789-804.

Loftsson et al., 1994, The effect of polyvinylpyrrolidone and hydroxypropyl methylcellulose on HP$\beta$CD complexation of hydrocortisone and its permeability through hairless mouse skin, European Journal of Pharmaceutical Sciences, 2:297-301.

(56) References Cited

OTHER PUBLICATIONS

Loftsson et al., 1994, The effect of water-soluble polymers on drug-cyclodextrin complexation, International Journal of Pharmaceutics (Netherlands), 110(2):169-177.
Loftsson et al., 1996, Effects of cyclodextrins and polymers on topical drug delivery to the eye—evaluations in humans, Proceedings of the 23rd International Symposium on Controlled Release of Bioactive Materials, pp. 453-454.
Loftsson et al., 1996, The influence of water-soluble polymers and pH on hydroxypropyl-β-cyclodextrin complexation of drugs, Drug Development and Industrial Pharmacy, 22(5):401-405.
Loftsson et al., 1997, Cyclodextrins as pharmaceutical excipients, Pharm. Technol. Eur. 9(5):26-34.
Loftsson et al., 1997, Enhanced complexation efficiency of cyclodextrins, Pharmaceutical Research, 14(11):S203.
Loftsson et al., 1998, Cyclodextrin solubilization of ETH-615, a zwitterionic drug, Drug Development and Industrial Pharmacy, 24(4):365-370.
Loftsson et al., 1998, The effect of water-soluble polymers on the aqueous solubility and complexing abilities of β-cyclodextrin, International Journal of Pharmaceutics, 163(1-2):115-121.
Loftsson et al., 1999, Methods to enhance the complexation efficiency of cyclodextrins, S.T.P. Pharma Sciences, 9(3):237-242.
Loftsson et al., 2001, Cyclodextrin solubilization of benzodiazepines: formulation of midazolam nasal spray, International Journal of Pharmaceutics, 212(1):29-40.
Loftsson et al., 2005, Cyclodextrins in drug delivery, Expert Opin. Drug Deliv., 2:335-351.
Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):S225.
Loftsson et al., Oct. 1996, Pharmaceutical applications of cyclodextrins. 1. Drug solubilization and stabilization, Journal of Pharmaceutical Sciences, , 85(10):1017-1025.
Loftsson et al., Sep. 16, 1996, Drug-cyclodextrin-polymer ternary complexes, European Journal of Pharmaceutical Sciences, 4(Suppl):S144.
Loftsson et al., Sep. 1996, Solubilization of β-cyclodextrin, Eur. J. Pharm. Sci, 4(Suppl.):S143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Loftsson, Nov. 1988, Increasing the cyclodextrin complexation of drugs and drug bioavailability through addition of water-soluble polymers, Pharmazie, 53(11):733-740.
Lucas et al., "Adsorption isotherms for ethylacetate and furfural on activated carbon from supercritical carbon dioxide," *Fluid Phase Equilibria*, 219 (2004) pp. 171-179.
Luna et al., 1996 Evaluation of the utility of capillary electrophoresis for the analysis of sulfobutyl ether β-cyclodextrin mixtures, J. Pharmaceutical and Biomedical Analysis 15:63-71.
Luna et al., 1996, Characterization of sulfobutyl ether β-cyclodextrin mixtures, Proceedings of the Eighth International Symposium on Cyclodextrins 133-136.
Luna et al., 1997, Fractionation and characterization of 4-sulfobutyl ether derivatives of cyclomaltoheptaose (β-cyclodextrin), Carbohydrate Research, 299:103-110.

Luna et al., 1997, Isolation and characterization by NMR spectroscopy of three monosubstituted 4-sulfobutyl ether derivatives of cyclomaltoheptose (β-cyclodextrin), Carbohydrate Research, 299(3):111-118.
Malaekeh-Nikouei et al., 2009, Evaluation the effect of cyclodextrin complexation on aqueous solubility of fluorometholone to achieve ophthalmic solution, J Incl Phemon Macrocycl Chem, 65(3-4):335-340.
Marshall et al., "Flax Shive as a Source of Activated Carbon for Metals Remediation," *BioResources*, (2007) 2(1), pp. 82-90.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
McDougall, G.J., "The physical nature and manufacture of activated carbon," *Journal of the South African Institute of Mining and Metallurgy*, Apr. 1991, vol. 91, No. 4, pp. 109-120.
Meng et al., "Eponemycin Exerts Its Antitumor Effect through the Inhibition of Proteasome Function," *Cancer Research*, Jun. 15, 1999, 59, pp. 2798-2801.
Modified Cyclodextrins: Scaffolds and Templates for Supramolecular Chemistry, Easton et al. eds., Imperial College Press, London, UK, 1999.
Molina-Sabio et al., "Porosity in Granular Carbons Activated With Phosphoric Acid," *Carbon*, © 1994, vol. 33, No. 8, pp. 1105-1113.
Mosher et al., "Sulfobutylether β-Cyclodextrin," *Handbook of Pharmaceutical Excipients*, Fifth Edition Pharmaceutical Press, Edited by Rowe et al., © 2006, pp. 754-757.
Mosher et al., "Sulfobutylether β-Cyclodextrin," *Handbook of Pharmaceutical Excipients, Sixth Edition*, Pharmaceutical Press, Edited by Rowe et al., © 2009, pp. 714-717.
Mosher et al., 2001, Complexation and Cyclodextrins, in Encyclopedia of Pharmaceutical Technology, Swarbrick et al., eds., Marcel Dekker, Inc., New York, pp. 49-71.
Murney, Peter, "To mix or not to mix—compatibilities of parenteral drug solutions," *Australian Prescriber*, vol. 31, No. 4, Aug. 2008, pp. 98-101.
Murty et al., "Quality control and drug analysis," *Am J Hosp Pharma*, Feb. 1977, vol. 34, No. 2, pp. 205-206.
Namasivayam et al., "Equilibrium and kinetic studies of adsorption of phosphate onto $ZnCl_2$ activated coir pith carbon," *Journal of Colloid and Interface Science*, 280 (2004) pp. 359-365.
Neunert et al., 2009, Glycosidic moiety changes the spectroscopic properties of DL-α-tocopherol in DMSO/water solution and in organic solvents, Molecular and biomolecular spectroscopy, Spectrochimica Acta Part A, 73:301-308.
New Trends in Cyclodextrins and Derivatives, Duchene ed., Editions de Sante, Parks, France, 1991.
Norit Americas Inc., Jul. 2007, Darco® KB-G Powdered Activated Carbon Product Datasheet, 2 pp.
Peeters et al., "Characterization of the Interaction of 2-Hydroxypropyl-β-cyclodextrin with Itraconazole at pH 2, 4, and 7," *Journal of Pharmaceutical Sciences*, vol. 91, No. 6, Jun. 2002, pp. 1414-1422.
Petrikkos et al., "Recent advances in antifungal chemotherapy," *International Journal of Antimicrobial Agents*, 30 (2007) pp. 108-117.
Pitha, "Amorphous Water-Soluble Derivatives of Cyclodextrins: from Test Tube to Patient," *Advances in Drug Delivery Systems*, 3, Third International Symposium on Recent Advances in Drug Delivery Systems, Feb. 24-27, 1987, Salt Lake City, UT, © Elsevier Science Publishers B.V., 1987, pp. 309-313.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Qu et al., 2002, Sulfoalkyl ether β-cyclodextrin derivatives: synthesis and characterizations, J. Inclusion Phenom. Macro. Chem, 43:213-221.
Rajewski et al., "Pharmaceutical Applications of Cyclodextrins. 2. In Vivo Drug Delivery," *Journal of Pharmaceutical Sciences*, vol. 85, No. 11, Nov. 1996, pp. 1142-1169.

(56) References Cited

OTHER PUBLICATIONS

Remington, "Instrumental Methods of Analysis," *Remington's Pharmaceutical Sciences*, Chapter 34, 17th Ed. (1985) pp. 623-624.
Remington's Pharmaceutical Sciences, 18th Edition, Gennaro ed., 1990, Hydrophilic Dispersions, pp. 436-437.
Remington's Pharmaceutical Sciences, 18th Edition, Gennaro ed., 1990, Hydrophilic Dispersions, pp. 291-294.
Sacco et al., 2011, Carfilzomib-dependent selective inhibition of the chymotrypsin-like activity of the proteasome leads to anti-tumor activity in Waldstrom's macroglobulinemia, Clinical Cancer Research, 17(7):1753-64.
Sandarusi et al., 1988, An automated flow calorimeter for heat capacity and enthalpy measurements, International Journal of Thermophysics, 9(6):993-1002.
Sanderink et al., "Human Aminopeptidases: A Review of the Literature," *J. Clin. Chem. Clin. Biochem.*, vol. 26, No. 12 (1988) pp. 795-807.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Seaman, Christine, "Spectroscopy Basics," in *Handbook of Food Science, Technology and Engineering*, © 2005 by Taylor & Francis Group, LLC, vol. 1, Chap. 43, pp. 43-1-43-23.
Schmitt et al., 2004, Chiral capillary electrophoresis: facts and fiction on the reproducibility of resolution with randomly substituted cyclodextrins, Electrophoresis, 25(16):2801-2807.
Sebestyen et al., 2013, Pharmaceutical applications of sulfobuthyleter-β-cyclodestrin, Acta Pharmaceutica Hungarica 83:57-68.
SEC Form 10-K as of Dec. 31, 2009 by Onyx Pharmaceuticals Inc. at Exhibit 10.22.
Shklyarev et al., "Synthesis, Acute Toxicity, and Antiarrhythmic Activity of Orthosubstituted Arylamides of Morpholinoacetic Acid," *Translated from Khimiko-farmatsevticheskii Zhurnal*, vol. 26, No. 3, Mar. 1992, © 1992 Plenum Publishing Corporation, pp. 235-238.
Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78.
Sokoloski, Theodore D., "Solutions and Phase Equilibria," *Remington's Pharmaceutical Sciences*, 17th Edition, 1985, Alfonso R. Gennaro, Editor, Mack Publishing Co., Chapter 16., pp. 207-229.
Sotthivirat et al., 2007, Evaluation of various properties of alternative salt forms of sulfobutylether-β-cyclodextrin, $(SBE)_{7M}$-β-CD, Int. J. Pharm. 330:73-81.
Sporanox® (itraconazole) Injection, Marketing Tech Info, Manufactured for: Ortho Biotech Products, L.P, Raritan, NJ 08869; Manufactured by: Hospira, Inc., Lake Forest, IL 60045, Revised Mar. 2009, 28 pages.
Stella, Mar. 31-Apr. 2, 1996, SBE7-β-CD, a new, novel and safe polyanionic β-cyclodextrin derivative: characterization and biomedical applications, Proceedings of the Eighth International Symposium on Cyclodextrins, Budapest, Hungary, pp. 471-476.

Sugawara et al., "Eponemycin [†], A New Antibiotic Active Against B16 Melanoma, I. Production, Isolation, Structure and Biological Activity," *The Journal of Antibiotics*, Jan. 1990, vol. XLIII, No. 1, pp. 8-18.
Szejtli, József, "Introduction and General Overview of Cyclodextrin Chemistry," *Chemical Reviews*, 1998, vol. 98, No. 5, pp. 1743-1753.
Szente et al., 1999, Highly soluble cyclodextrin derivatives: chemistry, properties, and trends in development, Advanced Drug Delivery Reviews 36:17-28.
Tarver et al., 2002, 2-O-substituted cyclodextrins as reversal agents for the neuromuscular blocker rocuronium bromide, Bioorganic & Medicinal Chemistry, 10:1819-1827.
The Handbook of Pharmaceutical Excipients, 5th Ed., Rowe et al., eds., The Pharmaceutical Press and American Pharmacists Association, London, UK and Washington, DC (2006).
Third European Congress of Pharmaceutical Sciences, Edinburgh, Scotland, UK, Sep. 15-17, 1996.
Thompson, Diane O., "Cyclodextrins-Enabling Excipients: A Case Study of the Development of a New Excipient—Sulfobutylether β-Cyclodextrin (Captisol®)," Chapt. 5, 51-67, *Excipient Development for Pharmaceutical, Biotechnology, and Drug Delivery Systems*, Edited by Katdare et al., © 2006 by Informa Healthcare USA, Inc., Chapter 5, pp. 51-67.
Thompson, Diane O., "Cyclodextrins—Enabling Excipients: Their Present and Future Use in Pharmaceuticals," *Critical Reviews™ in Therapeutic Drug Carrier Systems*, vol. 14, Issue 1 (1997) pp. 1-104.
Tongiani et al., 2005, Sulfoalkyl ether-alkyl ether-cyclodextrin derivatives, their synthesis, NMR characterization, and binding of 6α-methylprednisolone, J. Pharm. Sci., 94(11):2380-2392.
Trotta et al., 2000, Thermal degradation of cyclodextrins, Polymer Degradation and Stability, 69:373-379.
U.S. Department of Health and Human Services, Food and Drug Administration, Jul. 2006, Guidance for industry: Q3B(R2) impurities in new drug products, 18 pp.
USP 24, Official Monographs, "Cetylpyridinium Chloride," *The United States Pharmacopeia, The National Formulary*, Official from Jan. 1, 2000, pp. 370-373.
Vegvari et al., 2000, A new easy-to-prepare continuous electrochromatographic bed for enantiomer recognition, Electrophoresis, 21:3116-3125.
Wang et al., 2004, Bioavailability and anticataract effects of a topical ocular drug, Curr. Eye Res., 29(1):51-58.
Waterman et al., "Impurities in Drug Products," *Handbook of Isolation and Characterization of Impurities in Pharmaceuticals*, Academic Press, © 2003 Elsevier Science, Edited by Ahuja et al., Chapter 4, pp. 75-88.
Weatherhead et al., "Some Effects of Activated Charcoal as an Additive to Plant Tissue Culture Media," *Z. Pflanzenphysiol. Bd.* 89. S. (1978) pp. 141-147.
Wenz et al., 1999, Synthesis of highly water-soluble cyclodextrin sulfonates by addition of hydrogen sulfite to cyclodextrin allyl ethers, Carbohydr. Res. 322:153-165.
Wittung et al., 1994, Absorption flattening in the optical spectra of liposome-entrapped substances, FEBS Letters 352:37-40.
Yang et al., 2011, Pharmacokinetics, pharmacodynamics, metabolism, distribution, and excretion of carfilzomib in rats, Drug Metabolism and Distribution, 39(10):1873-1882.
Zia et al., 1997, Effect of alkyl chain length and degree of substitution on the complexation of sulfoalkyl ether β-cyclodextrins with steroids, Journal of Pharmaceutical Sciences, 86(2):220-224.

\* cited by examiner

FRACTIONATED ALKYLATED CYCLODEXTRIN COMPOSITIONS AND PROCESSES FOR PREPARING AND USING THE SAME

This application is a continuation of U.S. application Ser. No. 15/505,428, filed Feb. 27, 2017, now U.S. Pat. No. 10,851,184, which is the National Phase Entry of PCT/US2015/046408, filed Aug. 21, 2015, which claims the benefit of U.S. Provisional Patent Application No. 62/040,568 entitled "FRACTIONATED ALKYLATED CYCLODEXTRIN COMPOSITIONS AND PROCESSES FOR PREPARING AND USING THE SAME" filed on Aug. 22, 2014, the contents of each of which is incorporated by reference in its entirety.

BACKGROUND OF THE INVENTION

Field

The present invention relates to compositions comprising fractionated alkylated cyclodextrin compositions having a single degree of substitution, and processes for preparing and using the same.

Background Description

Hydrophobic, hydrophilic, polymerized, ionized, nonionized and many other derivatives of cyclodextrins have been developed, and their use in various industries has been established. Generally, cyclodextrin derivatization proceeds via reactions in which —OH groups at the 2-, 3-, and/or 6-position of the amylose rings of a cyclodextrin are replaced with substituent groups. Substituents include neutral, anionic and/or cationic functional groups.

Known cyclodextrin derivatives such as alkylated cyclodextrins include, but are not limited to, sulfoalkyl ether cyclodextrins, alkyl ether cyclodextrins (e.g., methyl, ethyl and propyl ether cyclodextrins), hydroxyalkyl cyclodextrins, thioalkyl ether cyclodextrins, carboxylated cyclodextrins (e.g., succinyl-β-cyclodextrin, and the like), sulfated cyclodextrins, and the like. Alkylated cyclodextrins having more than one type of functional group are also known, such as sulfoalkyl ether-alkyl ether-cyclodextrins (see, e.g., WO 2005/042584 and US 2009/0012042, each of which is hereby incorporated by reference in its entirety). In particular, alkylated cyclodextrins having 2-hydroxypropyl groups and/or sulfoalkyl ether groups have found use in pharmaceutical formulations.

A sulfobutyl ether derivative of β-cyclodextrin ("SBE-β-CD") has been commercialized by CyDex Pharmaceuticals, Inc. as Captisol® and Advasep®. The anionic sulfobutyl ether substituent improves the aqueous solubility and safety of the parent β-cyclodextrin, which can reversibly form complexes with active pharmaceutical agents, thereby increasing the solubility of active pharmaceutical agents and, in some cases, increase the stability of active pharmaceutical agents in aqueous solution. Captisol® has a chemical structure according to Formula I:

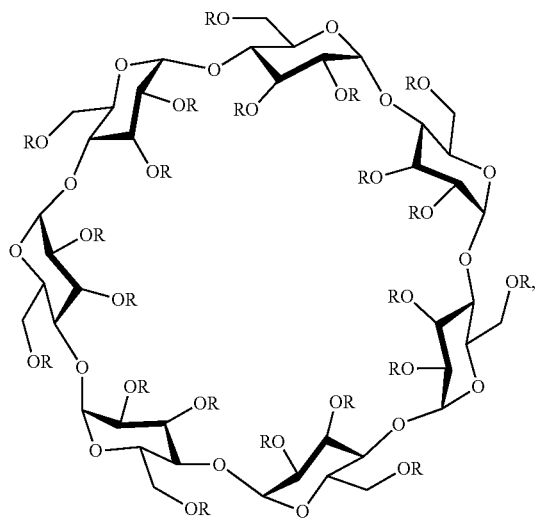

where R is $(-H)_{21-n}$ or $((-CH_2)_4-SO_3^-Na^+)_n$, and n is 6 to 7.1 and refers to an average degree of substitution.

SUMMARY

A fractionated alkylated cyclodextrin composition comprising 60% by weight or more alkylated cyclodextrin having a single degree of substitution relative to all alkylated cyclodextrin in the composition is provided herein.

In some embodiments, the fractionated alkylated cyclodextrin composition has a single degree of substitution of 1, 2, 3, 4, 5, 6, 7, 8, 9, 10, 11, or 12.

In some embodiments, the fractionated alkylated cyclodextrin composition comprises 70% by weight or more alkylated cyclodextrin having a single degree of substitution relative to all alkylated cyclodextrin in the composition. In some embodiments, the fractionated alkylated cyclodextrin composition comprises 80% by weight or more alkylated cyclodextrin having a single degree of substitution relative to all alkylated cyclodextrin in the composition.

In some embodiments, the alkylated cyclodextrin in the fractionated alkylated cyclodextrin composition is a sulfoalkyl ether cyclodextrin of Formula (11):

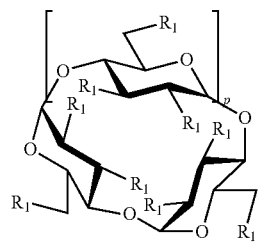

Formula (II)

wherein p is 4, 5, or 6, and $R_1$ is independently selected at each occurrence from —OH or —O—$(C_2$-$C_6$ alkylene)-$SO_3^-$-T, wherein T is independently selected at each occurrence from pharmaceutically acceptable cations, provided that at least one $R_1$ is —OH and at least one $R_1$ is O—$(C_2$-$C_6$ alkylene)-$SO_3^-$-T. In some embodiments, $R_1$ is independently selected at each occurrence from —OH or —O—(C$_4$ alkylene)-SO$_3^-$-T, and -T is Na$^+$ at each occurrence.

In some embodiments, the fractionated alkylated cyclodextrin composition is combined with one or more excipients.

In some embodiments, the fractionated alkylated cyclodextrin composition is combined with an active agent.

Also provided herein is a combination composition comprising a mixture of at least two different fractionated alkylated cyclodextrins, the mixture comprising:
(a) a first fractionated alkylated cyclodextrin having a single degree of substitution;
(b) a second fractionated alkylated cyclodextrin having a single degree of substitution,
wherein the first fractionated alkylated cyclodextrin composition and the second fractionated alkylated cyclodextrin composition are different and the combination of the first and second fractionated alkylated cyclodextrin is 60% by weight or more of all alkylated cyclodextrin in the composition.

In some embodiments, the single degree of substitution of the first fractionated alkylated cyclodextrin of the combination differs from the single degree of substitution of the second fractionated alkylated cyclodextrin by at least 1, 2, 3, 4, 5, 6, 7, 8, 9, 10, or 11.

In some embodiments, substituents on the first fractionated alkylated cyclodextrin and substituents on the second fractionated alkylated cyclodextrin are different. In some embodiments, substituents on the first fractionated alkylated cyclodextrin and substituents on the second fractionated alkylated cyclodextrin are the same.

In some embodiments, the first fractionated alkylated cyclodextrin, the second fractionated alkylated cyclodextrin, or both the first and second fractionated alkylated cyclodextrin of the combination composition is a sulfoalkyl ether cyclodextrin of Formula (II):

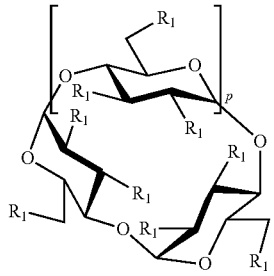

Formula (II)

wherein p is 4, 5, or 6, and R$_1$ is independently selected at each occurrence from —OH or —O—(C$_2$-C$_6$ alkylene)-SO$_3^-$-T, wherein T is independently selected at each occurrence from pharmaceutically acceptable cations, provided that at least one R$_1$ is —OH and at least one R$_1$ is O—(C$_2$-C$_6$ alkylene)-SO$_3^-$-T. In some embodiments, R$_1$ is independently selected at each occurrence from —OH or —O—(C$_4$ alkylene)-SO$_3^-$-T, and -T is Na$^+$ at each occurrence.

In some embodiments, the combination composition further comprises one or more excipients.

In some embodiments, the combination composition further comprises an active agent.

Also provided herein is a process for preparing a fractionated alkylated cyclodextrin composition comprising an alkylated cyclodextrin, the process comprising:

(a) preparing a solution comprising an alkylated cyclodextrin composition;
(b) passing the solution through a chromatographic separation system having a stationary phase and a mobile phase; and
(c) collecting a fractionated alkylated cyclodextrin composition comprising 60% by weight or more alkylated cyclodextrin having a selected single degree of substitution substitution relative to all alkylated cyclodextrin in the composition.

In some embodiments, the chromatographic separation system is high performance liquid chromatography. In some embodiments, the chromatographic separation system is reversed phase high performance liquid chromatography.

In some embodiments, the stationary phase of the chromatographic separation system comprises is a silica gel column.

In some embodiments, the mobile phase comprises acetonitrile. In some embodiments, the mobile phase further comprises an ammonium acetate buffer.

In some embodiments, the fractionated alkylated cyclodextrin composition prepared by a process described herein has a single degree of substitution of 1, 2, 3, 4, 5, 6, 7, 8, 9, 10, 11, or 12.

In some embodiments, the fractionated alkylated cyclodextrin composition prepared by a process described herein comprises 70% by weight or more alkylated cyclodextrin having a single degree of substitution relative to all alkylated cyclodextrin in the composition. In some embodiments, the fractionated alkylated cyclodextrin composition prepared by a process described herein comprises 80% by weight or more alkylated cyclodextrin having a single degree of substitution relative to all alkylated cyclodextrin in the composition.

In some embodiments, the alkylated cyclodextrin of the fractionated alkylated cyclodextrin composition prepared by process described herein is a sulfoalkyl ether cyclodextrin of Formula (II):

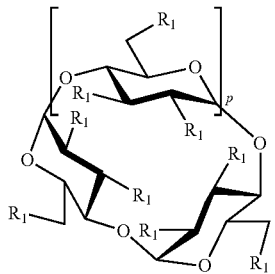

Formula (II)

wherein p is 4, 5, or 6, and R$_1$ is independently selected at each occurrence from —OH or —O—(C$_2$-C$_6$ alkylene)-SO$_3^-$-T, wherein T is independently selected at each occurrence from pharmaceutically acceptable cations, provided that at least one R$_1$ is —OH and at least one R$_1$ is O—(C$_2$-C$_6$ alkylene)-SO$_3^-$-T. In some embodiments, R$_1$ is independently selected at each occurrence from —OH or —O—(C$_4$ alkylene)-SO$_3^-$-T, and -T is Na$^+$ at each occurrence.

In some embodiments, the fractionated alkylated cyclodextrin composition prepared by a process described hereinfurther comprises combining the fractionated alkylated cyclodextrin composition with one or more excipients.

In some embodiments, the fractionated alkylated cyclodextrin composition prepared by a process described hereinfurther comprises combining the fractionated alkylated cyclodextrin composition with an active agent.

Products prepared by the processes described herein are also provided.

Further embodiments, features, and advantages of the present disclosure, as well as the composition, structure, and operation of various embodiments of the present disclosure, are described in detail below with reference to the accompanying drawings.

BRIEF DESCRIPTION OF THE DRAWINGS

The accompanying drawings, which are incorporated herein and form a part of the specification, illustrate one or more embodiments of the present invention and, together with the description, further serve to explain the principles of the invention and to enable a person skilled in the pertinent art to make and use the invention. The following drawings are given by way of illustration only, and thus are not intended to limit the scope of the present invention.

DETAILED DESCRIPTION

Figure 1:
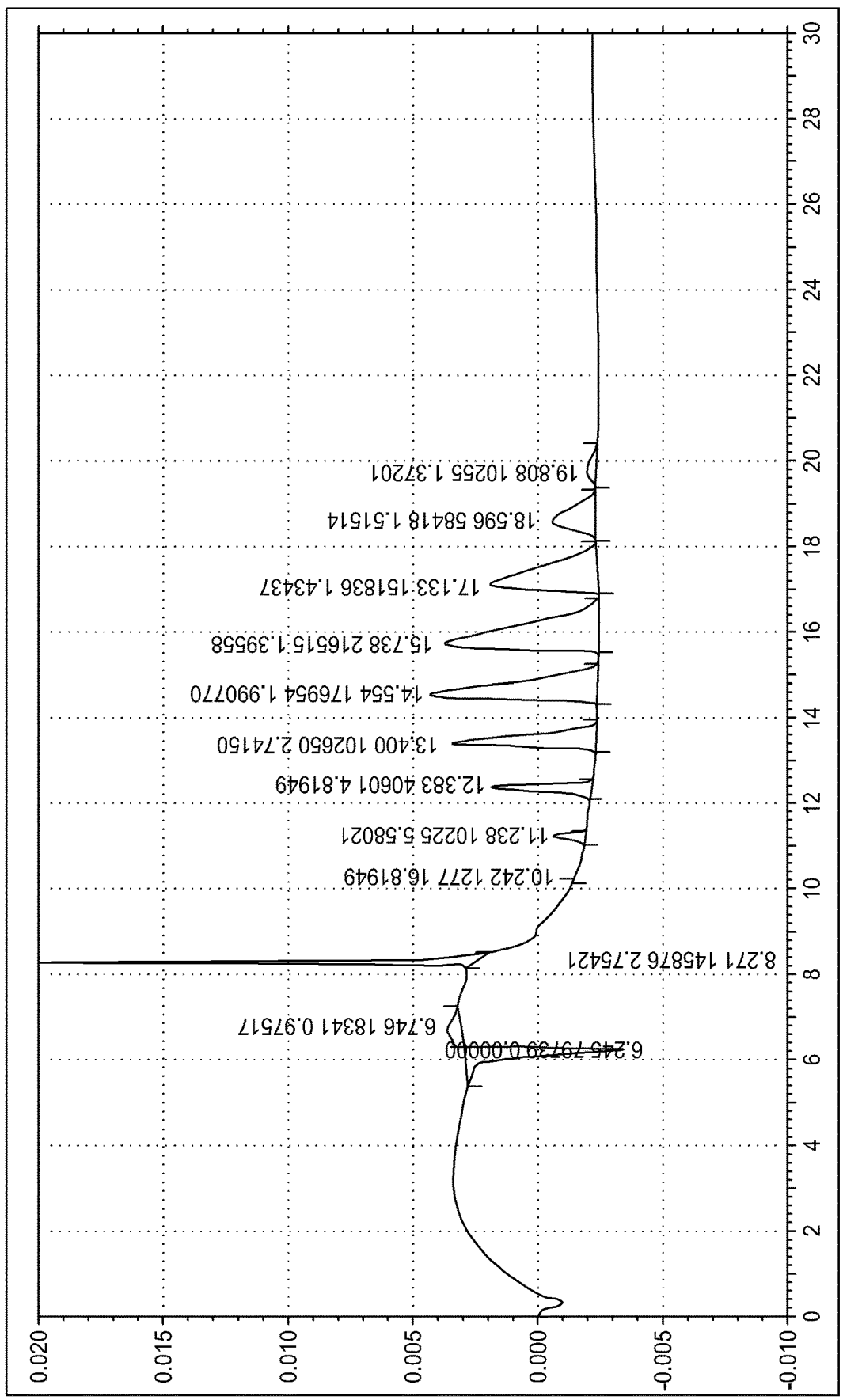
FIG. 1 provides an exemplary capillary electrophoresis electropherogram of a sample of Captisol® (Batch 17CX01.HQ00026).

The invention can include combinations and sub-combinations of the various aspects and embodiments disclosed herein. Further, when a particular feature, structure, or characteristic is described in connection with an embodiment, it is understood that it is within the knowledge of one skilled in the art to affect such feature, structure, or characteristic in connection with other embodiments whether or not explicitly described. These and other aspects will be apparent upon reference to the following detailed description, examples, claims and attached figures.

As used herein, percentages refer to "% by weight" and/or "w/w" (weight by weight concentration) unless otherwise indicated.

Fractionated Alkylated Cyclodextrin

An "alkylated cyclodextrin" refers to an α-, β-, or γ-cyclodextrin in which one or more —OH groups at the 2-, 3-, and/or 6-position of the amylose rings of the cyclodextrin are replaced with an —OR substituent group, wherein each R is an independently selected optionally substituted alkyl, —C(O)alkyl, or —C(O)Oalkyl moiety. The alkyl moiety can be straight-chained or branched and can include any degree of saturation (i.e., it includes alkenyl and alkynyl moieties). The optional substituents may include, but are not limited to, halo, hydroxy, sulfonate, thio, carboxy, amino, and nitro groups.

A "substituent precursor" refers to an agent capable of reacting with a hydroxyl group of a cyclodextrin starting material. A substituent precursor will react with the oxygen atom of a hydroxyl moiety of a parent cyclodextrin thereby converting the hydroxyl moiety to a target moiety (substituent) on the cyclodextrin. A substituent precursor can also be referred to herein as an alkylating agent. Exemplary alkylating agents that can be used to derivatize (etherify) the cyclodextrin include, by way of example and without limitation, various alkyl sulfate esters. Specific alkyl ether (AE) precursors include sulfate esters such as diethyl sulfate, dimethyl sulfate, and dipropyl sulfate, or methylating agents such as trimethyloxonium tetrafluoroborate (TMOTFB), trimethyloxonium p-toluenesulfonate, trimethyloxonium hexafluorophosphate, trimethyloxonium hexafluoroantimonate, trimethyloxonium alkane/aryl sulfonate, dimethoxycarbenium tetrafluoroborate, and O-methyldibenzofuranium tetrafluoroborate, or trialkylsulfonium halide agents such as trimethylsulfonium iodide. Exemplary sulfoalkylating agents that can be used to derivatize (etherify) the cyclodextrin include, by way of example and without limitation, alkyl sultone. Specific sulfoalkyl ether (SAE) precursors include 1,4-butane sultone, 1,5-pentane sultone, 1,3-propane sultone, and other sulfoalkylating agents. Exemplary hydroxyalkyl ether (HAE) precursors that can be used to derivatize the cyclodextrin include 2,3-epoxy alcohols or halohydrins and others described in references cited herein. Exemplary hydroxyalkenyl ether (HANE) precursor that can be used to derivatize the cyclodextrin include 3,4-epoxy-1-butene, 4,5-epoxy-1-pentene, 5,6-epoxy-1-hexene and other epoxy alkenyl agents. An exemplary EPPE (epoxyalkyl ether; epoxyalkylating agent) precursor includes epichlorohydrin.

As used herein, "alkylene" and "alkyl" refer to (e.g., in the —O—($C_2$-$C_6$-alkylene)$SO_3^-$ group), linear, cyclic, and branched, saturated and unsaturated (i.e., containing one double bond) divalent alkylene groups and monovalent alkyl groups, respectively. The term "alkanol" as used herein likewise includes linear, cyclic and branched as well as saturated and unsaturated alkyl components of the alkanol groups, in which the hydroxyl groups can be situated at any position on the alkyl moiety. The term "cycloalkanol" includes unsubstituted or substituted (e.g., by methyl or ethyl) cyclic alcohols.

An "alkylated cyclodextrin composition" is a composition comprising alkylated cyclodextrins having a degree of substitution or an average degree of substitution (ADS) for a specified substituent. In some embodiments, an alkylated cyclodextrin composition comprises a distribution of alkylated cyclodextrin species differing in the individual degree of substitution specified substituent for each species, wherein the specified substituent for each species is the same. The alkylated cyclodextrin composition is a substantially pharmaceutically inactive composition (i.e., a composition which does not contain a pharmaceutically active agent). For example, a cyclodextrin composition may comprise at least 90% by weight cyclodextrin, at least 95% by weight cyclodextrin, at least 97% by weight cyclodextrin, at least 99% by weight cyclodextrin, at least 99.9% by weight cyclodextrin, or at least 99.99% by weight cyclodextrin.

The alkylated cyclodextrin can be a water soluble alkylated cyclodextrin, which is any alkylated cyclodextrin exhibiting enhanced water solubility over its corresponding underivatized parent cyclodextrin and having a molecular structure based upon α-, β- or γ-cyclodextrin. In some embodiments, a derivatized cyclodextrin prepared by a process of the present disclosure has a solubility in water of 100 mg/mL or higher, or a solubility in water of less than 100 mg/mL.

The cyclodextrin can be derivatized with neutral, anionic or cationic substituents at the C2, C3, or C6 positions of the individual saccharides forming the cyclodextrin ring. Suitable water soluble alkylated cyclodextrins are described herein. The alkylated cyclodextrin can also be a water insoluble alkylated cyclodextrin or a alkylated cyclodextrin possessing a lower water solubility than its corresponding underivatized parent cyclodextrin.

Sulfoalkyl ether derivatized cyclodextrins (such as Captisol®) are prepared using batch methods as described in, e.g., U.S. Pat. Nos. 5,134,127, 5,376,645 and 6,153,746, each of which is hereby incorporated by reference in its entirety.

Sulfoalkyl ether cyclodextrins and other derivatized cyclodextrins can also be prepared according to the methods described in the following patents and published patent applications: U.S. Pat. Nos. 3,426,011, 3,453,257, 3,453,259, 3,459,731, 4,638,058, 4,727,06, 5,019,562, 5,173,481, 5,183,809, 5,241,059, 5,536,826, 5,594,125, 5,658,894, 5,710,268, 5,756,484, 5,760,015, 5,846,954, 6,407,079, 6,670,340, 7,625,878, 7,629,331, 7,635,773, 8,278,437, and JP 05001102, as well as in the following non-patent publications: Lammers et al., *Recl. Trav. Chim. Pays-Bas* 91:733 (1972); Lammers et al., *Staerke* 23:167 (1971), Adam et al., *J. Med Chem.* 45:1806 (2002), Qu et al., *J. Inclusion Phenom. Macrocyclic Chem.* 43:213 (2002), Tarver et al., *Bioorg. Med. Chem.* 10:1819 (2002), Fromming et al., *Cyclodextrins in Pharmacy* (Kluwer Academic Publishing, Dordrecht, 1994), *Modified Cyclodextrins: Scaffolds and Templates for Supramolecular Chemistry* (C. J. Easton et al. eds., Imperial College Press, London, UK, 1999), *New Trends in Cyclodextrins and Derivatives* (Dominique Duchene ed., Editions de Santé, Paris, FR, 1991), *Comprehensive Supramolecular Chemistry* 3 (Elsevier Science Inc., Tarrytown, N.Y.), the entire disclosures of which are hereby incorporated by reference.

Impurities present in an alkylated cyclodextrin composition can reduce the shelf-life and potency of an active agent composition. Impurities can be removed from an alkylated cyclodextrin composition by exposure to (e.g., mixing with) activated carbon. The treatment of cyclodextrin-containing aqueous solutions and suspensions with activated carbon is known. See, e.g., U.S. Pat. Nos. 4,738,923, 5,393,880, and 5,569,756.

A "fractionated alkylated cyclodextrin composition" is a composition having alkylated cyclodextrins that are enriched with respect to a single degree of substitution for a specified substituent. In some embodiments, a fractionated alkylated cyclodextrin composition is one of the purified fractions of an alkylated cyclodextrin composition prepared by a process described herein.

Cyclodextrin species are distinguished in part by the substituents attached to them. "SAE" refers to a sulfoalkyl ether derivative. "HAE" refers to a hydroxyalkyl ether derivative. "AE" is an alkyl ether derivative.

The "degree of substitution" for a specific moiety (SAE, HAE, or AE, for example) is a measure of the number of substituents attached to an individual cyclodextrin molecule, in other words, the moles of a substituent per mole of cyclodextrin. Therefore, each substituent has its own degree of substitution for an individual cyclodextrin derivative species. The "average degree of substitution" for a substituent is a measure of the total number of substituents per molecule for the distribution of cyclodextrin derivatives within a cyclodextrin derivative composition. Therefore, a $SAE_4$-CD has an average degree of substitution (per cyclodextrin molecule) of 4.

The alkylated cyclodextrin compositions prior to fractionation can comprise plural individual alkylated cyclodextrin species differing in individual degree of substitution, such that the average degree of substitution is calculated, as described herein, from the individual degrees of substitution of the species. The process described herein separates (or fractionates) the individual alkylated cyclodextrin species with a single degree of substitution from individual alkylated cyclodextrin species with different single degrees of substitution.

The term "single degree of substitution" as used herein, is a measure of the total number of substituents (SAE, HAE, or AE, for example) present per cyclodextrin molecule for an alkylated cyclodextrin.

Some embodiments provide a fractionated alkylated cyclodextrin composition having a single degree of substitution of 60% by weight or more of an individual alkylated cyclodextrin species with a single degree of substitution relative to all alkylated cyclodextrin within the alkylated cyclodextrin composition. In some embodiments, a fractionated alkylated cyclodextrin composition having a single degree of substitution comprises 60% or more, 65% or more, 70% or more, 75% or more, 80% or more, 85% or more, 90% or more, 95% or more, 96% or more, 97% or more, 98% or more, or 99% or more by weight of an individual alkylated cyclodextrin species with a single degree of substitution relative to all alkylated cyclodextrin within the alkylated cyclodextrin composition.

In some embodiments, the single degree of substitution and the average degree of substitution for a fractionated alkylated cyclodextrin composition are the same. In some embodiments, the single degree of substitution and the average degree of substitution for a fractionated alkylated cyclodextrin composition are different. For example, a fractionated alkylated cyclodextrin composition with single degree of substitution of 6 comprising 60% by weight of an individual alkylated cyclodextrin species of 6, can have an average degree of substitution of 4, 5, 6, 7, or 8.

In some embodiments, the fractionated alkylated cyclodextrin having a single degree of substitution comprises 1, 2, 3, 4, 5, 6, 7, 8, 9, 10, 11, or 12 substituents per alkylated cyclodextrin within the alkylated cyclodextrin composition.

The fractionated alkylated cyclodextrin can be a water-soluble alkylated cyclodextrin, which is any alkylated cyclodextrin exhibiting enhanced water solubility over its corresponding underivatized parent cyclodextrin and having a molecular structure based upon $\alpha$-, $\beta$- or $\gamma$-cyclodextrin. In some embodiments, the fractionated alkylated cyclodextrin composition has a solubility in water of 100 mg/mL or higher, or a solubility in water of less than 100 mg/mL.

The fractionated alkylated cyclodextrin can be derivatized with neutral, anionic, or cationic substituents at the C2, C3, or C6 positions of the individual saccharides forming the cyclodextrin ring. Suitable water-soluble fractionated alkylated cyclodextrins are described herein. The fractionated alkylated cyclodextrin can also be a water insoluble alkylated cyclodextrin or an alkylated cyclodextrin possessing a lower water solubility than its corresponding underivatized parent cyclodextrin.

As used herein, a "substituent precursor" or "alkylating agent" refers to a compound, reagent, moiety, or substance capable of reacting with an —OH group present on a cyclodextrin. In some embodiments, the fractionated alkylated cyclodextrin includes a substituent such as a sulfoalkyl ether group, an ether group, an alkyl ether group, an alkenyl ether group, a hydroxyalkyl ether group, a hydroxyalkenyl ether group, a thioalkyl ether group, an aminoalkyl ether group, a mercapto group, an amino group, an alkylamino group, a carboxyl group, an ester group, a nitro group, a halo group, an aldehyde group, a 2,3-epoxypropyl group, and combinations thereof. In some embodiments, alkylating agents include an alkyl sultone (e.g., 1,4-butane sultone, 1,5-pentane sultone, 1,3-propane sultone, and the like).

In some embodiments, fractionated alkylated cyclodextrins such as mixed ether alkylated cyclodextrins include, by way of example, those listed in Table 1 below.

TABLE 1

| Mixed ether CD derivative | Mixed ether CD derivative | Mixed ether CD derivative |
| --- | --- | --- |
| Sulfobutyl-hydroxybutyl-CD (SBE-HBE-CD) | Sulfopropyl-hydroxybutyl-CD (SPE-HBE-CD) | Sulfoethyl-hydroxybutyl-CD (SEE-HBE-CD) |
| Sulfobutyl-hydroxypropyl-CD (SBE-HPE-CD) | Sulfopropyl-hydroxypropyl-CD (SPE-HPE-CD) | Sulfoethyl-hydroxypropyl-CD (SEE-HPE-CD) |
| Sulfobutyl-hydroxyethyl-CD (SBE-HEE-CD) | Sulfopropyl-hydroxyethyl-CD (SPE-HEE-CD) | Sulfoethyl-hydroxyethyl-CD (SEE-HEE-CD) |
| Sulfobutyl-hydroxybutenyl-CD (SBE-HBNE-CD) | Sulfopropyl-hydroxybutenyl-CD (SPE-HBNE-CD) | Sulfoethyl-hydroxybutenyl-CD (SEE-HBNE-CD) |
| Sulfobutyl-ethyl (SBE-EE-CD) | Sulfopropyl-ethyl (SPE-EE-CD) | Sulfoethyl-ethyl (SEE-EE-CD) |
| Sulfobutyl-methyl (SBE-ME-CD) | Sulfopropyl-methyl (SPE-ME-CD) | Sulfoethyl-methyl (SEE-ME-CD) |
| Sulfobutyl-propyl (SBE-PE-CD) | Sulfopropyl-propyl (SPE-PE-CD) | Sulfoethyl-propyl (SEE-PE-CD) |
| Sulfobutyl-butyl (SBE-BE-CD) | Sulfopropyl-butyl (SPE-BE-CD) | Sulfoethyl-butyl (SEE-BE-CD) |
| Sulfobutyl-carboxymethyl-CD (SBE-CME-CD) | Sulfopropyl-carboxymethyl-CD (SPE-CME-CD) | Sulfoethyl-carboxymethyl-CD (SEE-CME-CD) |
| Sulfobutyl-carboxyethyl-CD (SBE-CEE-CD) | Sulfopropyl-carboxyethyl-CD (SPE-CEE-CD) | Sulfoethyl-carboxyethyl-CD (SEE-CEE-CD) |
| Sulfobutyl-acetate-CD (SBE-AA-CD) | Sulfopropyl-acetate-CD (SPE-AA-CD) | Sulfoethyl-acetate-CD (SEE-AA-CD) |
| Sulfobutyl-propionate-CD (SBE-PA-CD) | Sulfopropyl-propionate-CD (SPE-PA-CD) | Sulfoethyl-propionate-CD (SEE-PA-CD) |
| Sulfobutyl-butyrate-CD (SBE-BA-CD) | Sulfopropyl-butyrate-CD (SPE-BA-CD) | Sulfoethyl-butyrate-CD (SEE-BA-CD) |
| Sulfobutyl-methoxycarbonyl-CD (SBE-MC-CD) | Sulfopropyl-methoxycarbonyl-CD (SPE-MC-CD) | Sulfoethyl-methoxycarbonyl-CD (SEE-MC-CD) |
| Sulfobutyl-ethoxycarbonyl-CD (SBE-EC-CD) | Sulfopropyl-ethoxycarbonyl-CD (SPE-EC-CD) | Sulfoethyl-ethoxycarbonyl-CD (SEE-EC-CD) |
| Sulfobutyl-propoxycarbonyl-CD (SBE-PC-CD) | Sulfopropyl-propoxycarbonyl-CD (SPE-PC-CD) | Sulfoethyl-propoxycarbonyl-CD (SEE-PC-CD) |
| Hydroxybutyl-hydroxybutenyl-CD (HBE-HBNE-CD) | Hydroxypropyl-hydroxybutenyl-CD (HPE-HBNE-CD) | Hydroxyethyl-hydroxybutenyl-CD (HEE-HBNE-CD) |
| Hydroxybutyl-ethyl (HBE-EE-CD) | Hydroxypropyl-ethyl (HPE-EE-CD) | Hydroxyethyl-ethyl (HEE-EE-CD) |
| Hydroxybutyl-methyl (HBE-ME-CD) | Hydroxypropyl-methyl (HPE-ME-CD) | Hydroxyethyl-methyl (HEE-ME-CD) |
| Hydroxybutyl-propyl (HBE-PE-CD) | Hydroxypropyl-propyl (HPE-PE-CD) | Hydroxyethyl-propyl (HEE-PE-CD) |
| Hydroxybutyl-butyl (HBE-BE-CD) | Hydroxypropyl-butyl (HPE-BE-CD) | Hydroxyethyl-butyl (HEE-BE-CD) |
| Hydroxybutyl-carboxymethyl-CD (HBE-CME-CD) | Hydroxypropyl-carboxymethyl-CD (HPE-CME-CD) | Hydroxyethyl-carboxymethyl-CD (HEE-CME-CD) |
| Hydroxybutyl-carboxyethyl-CD (HBE-CEE-CD) | Hydroxypropyl-carboxyethyl-CD (HPE-CEE-CD) | Hydroxyethyl-carboxyethyl-CD (HEE-CEE-CD) |
| Hydroxybutyl-acetate-CD (HBE-AA-CD) | Hydroxypropyl-acetate-CD (HPE-AA-CD) | Hydroxyethyl-acetate-CD (HEE-AA-CD) |
| Hydroxybutyl-propionate-CD (HBE-PA-CD) | Hydroxypropyl-propionate-CD (HPE-PA-CD) | Hydroxyethyl-propionate-CD (HEE-PA-CD) |
| Hydroxybutyl-butyrate-CD (HBE-BA-CD) | Hydroxypropyl-butyrate-CD (HPE-BA-CD) | Hydroxyethyl-butyrate-CD (HEE-BA-CD) |
| Hydroxybutyl-methoxycarbonyl-CD (HBE-MC-CD) | Hydroxypropyl-methoxycarbonyl-CD (HPE-MC-CD) | Hydroxyethyl-methoxycarbonyl-CD (HEE-MC-CD) |
| Hydroxybutyl-ethoxycarbonyl-CD (HBE-EC-CD) | Hydroxypropyl-ethoxycarbonyl-CD (HPE-EC-CD) | Hydroxyethyl-ethoxycarbonyl-CD (HEE-EC-CD) |
| Hydroxybutyl-propoxycarbonyl-CD | Hydroxypropyl-propoxycarbonyl-CD | Hydroxyethyl-propoxycarbonyl-CD |

TABLE 1-continued

| Mixed ether CD derivative | Mixed ether CD derivative | Mixed ether CD derivative |
|---|---|---|
| (HBE-PC-CD) Hydroxybutenyl-ethyl (HBNE-EE-CD) Hydroxybutenyl-methyl (HBNE-ME-CD) Hydroxybutenyl-propyl (HBNE-PE-CD) Hydroxybutenyl-butyl (HBNE-BE-CD) Hydroxybutenyl-carboxymethyl-CD (HBNE-CME-CD) Hydroxybutenyl-carboxyethyl-CD (HBNE-CEE-CD)- Hydroxybutenyl-acetate-CD (HBNE-AA-CD) Hydroxybutenyl-propionate-CD (HBNE-PA-CD) Hydroxybutenyl-butyrate-CD (HBNE-BA-CD) Hydroxybutenyl-methoxycarbonyl-CD (HBNE-MC-CD) Hydroxybutenyl-ethoxycarbonyl-CD (HBNE-EC-CD) Hydroxybutenyl-propoxycarbonyl-CD (HBNE-PC-CD) | (HPE-PC-CD) Hydroxypropenyl-ethyl (HPNE-EE-CD) Hydroxypropenyl-methyl (HPNE-ME-CD) Hydroxypropenyl-propyl (HPNE-PE-CD) Hydroxypropenyl-butyl (HPNE-BE-CD) Hydroxypropenyl-carboxymethyl-CD (HPNE-CME-CD) Hydroxypropenyl-carboxyethyl-CD (HPNE-CEE-CD) Hydroxypropenyl-acetate-CD (HPNE-AA-CD) Hydroxypropenyl-propionate-CD (HPNE-PA-CD) Hydroxypropenyl-butyrate-CD (HPNE-BA-CD) Hydroxypropenyl-methoxycarbonyl-CD (HPNE-MC-CD) Hydroxypropenyl-ethoxycarbonyl-CD (HPNE-EC-CD) Hydroxypropenyl-propoxycarbonyl-CD (HPNE-PC-CD) | (HEE-PC-CD) Hydroxypentenyl-ethyl (HPTNE-EE-CD) Hydroxypentenyl-methyl (HPTNE-ME-CD) Hydroxypentenyl-propyl (HPTNE-PE-CD) Hydroxypentenyl-butyl (HPTNE-BE-CD) Hydroxypentenyl-carboxymethyl-CD (HPTNE-CME-CD) Hydroxypentenyl-carboxyethyl-CD (HPTNE-CEE-CD) Hydroxypentenyl-acetate-CD (HPTNE-AA-CD) Hydroxypentenyl-propionate-CD (HPTNE-PA-CD) Hydroxypentenyl-butyrate-CD (HPTNE-BA-CD) Hydroxypentenyl-methoxycarbonyl-CD (HPTNE-MC-CD) Hydroxypentenyl-ethoxycarbonyl-CD (HPTNE-EC-CD) Hydroxypentenyl-propoxycarbonyl-CD (HPTNE-PC-CD) |

After reaction, purification, isolation, and/or fractionation, the fractionated alkylated cyclodextrin composition can comprise small amounts (e.g., 1% or less, 0.5% or less, 0.1% or less, 0.05% or less, 0.001% or less, 0.0005% or less, or 0.0001% or less, by weight) of a cyclodextrin starting material (e.g., an underivatized parent cyclodextrin).

The fractionated alkylated cyclodextrin can be present in high purity form. See U.S. Pat. No. 7,635,773, which is incorporated herein by reference in its entirety. In some embodiments, the fractionated alkylated cyclodextrin is a high purity SAE-CD composition having a reduced amounts of UV active impurities, which may cause drug-degradation. The composition optionally has a reduced amount of phosphate or excludes phosphate entirely The fractionated SAE-CD composition can also have reduced amounts of 1,4-butane sultone and 4-hydroxy-butane-1-sulfonic acid.

A fractionated alkylated cyclodextrin composition of the present disclosure provides unexpected advantages over other structurally related alkylated cyclodextrin compositions. By "structurally related" is meant, for example, that the substituent of the fractionated alkylated cyclodextrin in the composition is essentially the same as the substituent of the other alkylated cyclodextrin to which it is being compared. Exemplary advantages can include an enhanced purity, reduced content of pyrogens, reduced content of drug-degrading components, reduced content of color-forming agents, reduced content of unreacted substituent precursor, and/or reduced content of unreacted cyclodextrin starting material. An exemplary advantage also includes a reduced chloride content. These advantages stem in part from the fact that the presently disclosed process by which a fractionated alkylated cyclodextrin composition is prepared will, in addition to producing the fractionated composition, remove impurities, reduce endotoxins, and remove color-forming agents. Additionally, a fractionated alkylated cyclodextrin composition having a single degree of substitution can provide the advantage of a lower molecular weight than other structurally related alkylated cyclodextrin species. For example, a fractionated alkylated cyclodextrin composition having a single degree of substitution of 3 would be expected to have a molecular weight of about 1609 Da, while a structurally related alkylated cyclodextrin having an average degree of substitution of 6.5 would be expected to have a molecular weight of 2162 Da. For drug compounds wherein an alkylated cyclodextrin having an individual degree of substitution of 3 provides the highest solubility, a lower amount of alkylated cyclodextrin would be required to solubilize the drug when the cyclodextrin composition is a fractionated alkylated cyclodextrin composition having a single degree of substitution of 3. In turn, the use of less alkylated cyclodextrin could lead to better safety markers in animal studies.

A water-soluble fractionated alkylated cyclodextrin composition can comprise a sulfoalkyl ether cyclodextrin (SAE-CD) compound, or mixture of compounds, of the Formula II:

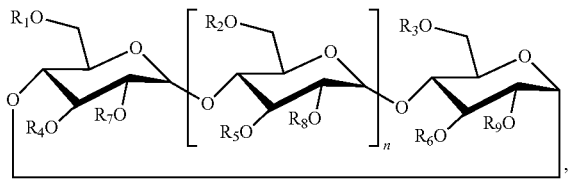

wherein: n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group.

In some embodiments, a fractionated SAE-CD composition comprises a water-soluble alkylated cyclodextrin of Formula III:

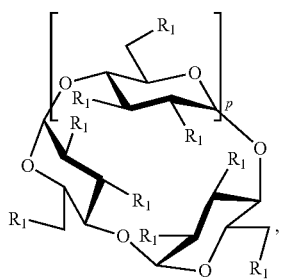

wherein: p is 4, 5 or 6;
$R_1$ is independently selected at each occurrence from —OH or -SAE-T;
-SAE- is a —O—($C_2$-$C_6$ alkylene)-$SO_3^-$ group, wherein at least one SAE is independently a —O—($C_2$-$C_6$ alkylene)-$SO_3^-$ group, a —O—($CH_2$)$SO_3^-$ group, wherein g is 2 to 6, or 2 to 4, (e.g., —$OCH_2CH_2CH_2SO_3^-$ or —$OCH_2CH_2CH_2CH_2SO_3^-$); and -T is independently selected at each occurrence from the group consisting of pharmaceutically acceptable cations, which group includes, for example, $H^+$, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine among others; provided that at least one $R_1$ is a hydroxyl moiety and at least one $R_1$ is -SAE-T.

When at least one $R_1$ of a derivatized cyclodextrin molecule is -SAE-T, the single degree of substitution, in terms of the -SAE-T moiety, is understood to be at least one (1). When the term -SAE- is used to denote a sulfoalkyl-(alkylsulfonic acid)-ether moiety it being understood that the -SAE- moiety comprises a cation (-T) unless otherwise specified. Accordingly, the terms "SAE" and "—SAE-T" can, as appropriate, be used interchangeably herein.

Since SAE-CD is a poly-anionic cyclodextrin, it can be provided in different salt forms. Suitable counterions include cationic organic atoms or molecules and cationic inorganic atoms or molecules. The fractionated SAE-CD can include a single type of counterion or a mixture of different counterions. The properties of the fractionated SAE-CD can be modified by changing the identity of the counterion present. For example, a first salt form of a fractionated SAE-CD composition can possess greater osmotic potential or greater water activity reducing power than a different second salt form of the same fractionated SAE-CD.

In some embodiments, a sulfoalkyl ether cyclodextrin is complexed with one or more pharmaceutically acceptable cations selected from, e.g., $H^+$, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine, and the like, and combinations thereof.

Further exemplary SAE-CD derivatives include:

TABLE 2

| $SAE_x$-α-CD | $SAE_x$-β-CD | $SAE_x$-γ-CD |
| --- | --- | --- |
| (Sulfoethyl ether)$_x$-α-CD | (Sulfoethyl ether)$_x$-β-CD | (Sulfoethyl ether)$_x$-γ-CD |
| (Sulfopropyl ether)$_x$-α-CD | (Sulfopropyl ether)$_x$-β-CD | (Sulfopropyl ether)$_x$-γ-CD |
| (Sulfobutyl ether)$_x$-α-CD | (Sulfobutyl ether)$_x$-β-CD | (Sulfobutyl ether)$_x$-γ-CD |
| (Sulfopentyl ether)$_x$-α-CD | (Sulfopentyl ether)$_x$-β-CD | (Sulfopentyl ether)$_x$-γ-CD |
| (Sulfohexyl ether)$_x$-α-CD | (Sulfohexyl ether)$_x$-β-CD | (Sulfohexyl ether)$_x$-γ-CD | wherein x denotes the single degree of substitution. In some embodiments, the alkylated cyclodextrins are formed as salts.

Various embodiments of a fractionated sulfoalkyl ether cyclodextrin include eicosa-O-(methyl)-6G-O-(4-sulfobutyl)-β-cyclodextrin, heptakis-O-(sulfomethyl)-tetradecakis-O-(3-sulfopropyl)-β-cyclodextrin, heptakis-O-[(1,1-dimethylethyl)dimethylsilyl]-tetradecakis-O-(3-sulfopropyl)-β-cyclodextrin, heptakis-O-(sulfomethyl)-tetradecakis-O-(3-sulfopropyl)-β-cyclodextrin, and heptakis-O-[(1,1-dimethylethyl)dimethylsilyl]-tetradecakis-O-(sulfomethyl)-β-cyclodextrin. Other known fractionated alkylated cyclodextrins containing a sulfoalkyl moiety include sulfoalkylthio and sulfoalkylthioalkyl ether derivatives such as octakis-(S-sulfopropyl)-octathio-γ-cyclodextrin, octakis-O-[3-[(2-sulfoethyl)thio]propyl]-β-cyclodextrin], and octakis-S-(2-sulfoethyl)-octathio-γ-cyclodextrin.

In some embodiments, the fractionated alkylated cyclodextrin composition is a sulfoalkyl ether-β-cyclodextrin composition having a single degree of substitution of 1, 2, 3, 4, 5, 6, 7, 8, 9, 10, 11, or 12 substituents per alkylated cyclodextrin, and the remaining substituents are —H.

In some embodiments, the fractionated alkylated cyclodextrin is a compound of Formula IV:

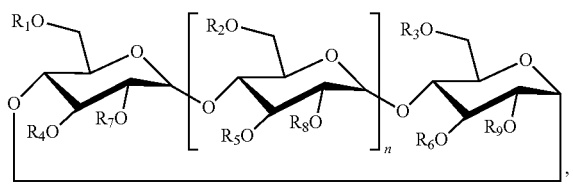

IV n is 4, 5 or 6, wherein $R_1$, $R_2$, $R_3$, $R_4$, $R_5$, $R_6$, $R_7$, $R_8$ and $R_9$ are independently selected from: —H, a straight-chain or branched $C_1$-$C_5$-(alkylene)-$SO_3^-$ group, and an optionally substituted straight-chain or branched $C_1$-$C_6$ group.

A water-soluble fractionated alkylated cyclodextrin composition can comprise an alkyl ether cyclodextrin (AE-CD) compound, or mixture of compounds, of the Formula V:

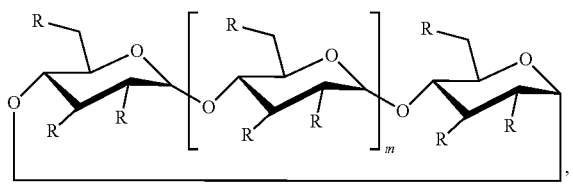

V wherein: m is 4, 5 or 6; R is independently selected at each occurrence from the group consisting of —OH and AE; and AE is —O—($C_1$-$C_6$ alkyl); provided that at least one R is —OH; and at least one AE is present.

Further exemplary AE-CD derivatives include:

TABLE 3

| (Alkylether)$_y$-α-CD | (Alkylether)$_y$-β-CD | (Alkylether)$_y$-γ-CD |
|---|---|---|
| ME$_y$-α-CD | ME$_y$-β-CD | ME$_y$-γ-CD |
| EE$_y$-α-CD | EE$_y$-β-CD | EE$_y$-γ-CD |
| PE$_y$-α-CD | PE$_y$-β-CD | PE$_y$-γ-CD |
| BE$_y$-α-CD | BE$_y$-β-CD | BE$_y$-γ-CD |
| PtE$_y$-α-CD | PtE$_y$-β-CD | PtE$_y$-γ-CD |
| HE$_y$-α-CD | HE$_y$-β-CD | HE$_y$-γ-CD | wherein ME denotes methyl ether, EE denotes ethyl ether, PE denotes propyl ether, BE denotes butyl ether, PtE denotes pentyl ethyl, HE denotes hexyl ether, and y denotes the single degree of substitution.

A water-soluble fractionated alkylated cyclodextrin composition can comprise a hydroxyalkyl ether cyclodextrin (HAE-CD) compound, or mixture of compounds, of the Formula VI:

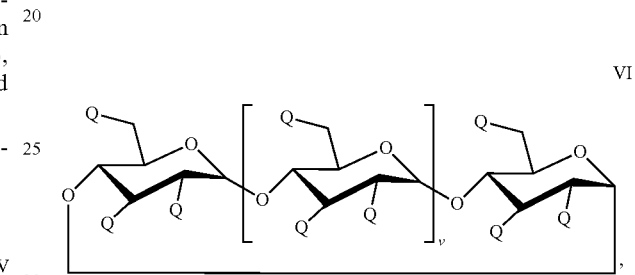

VI wherein: v is 4, 5 or 6; Q is independently selected at each occurrence from the group consisting of —OH, and -HAE; and HAE is HO($C_1$-$C_6$ alkyl)-O—, provided that at least one -HAE moiety is present.

Further exemplary hydroxyalkyl ether cyclodextrin (HAE-CD) derivatives include:

TABLE 4

| (HAE)$_z$-α-CD | (HAE)$_z$-β-CD | (HAE)$_z$-γ-CD |
|---|---|---|
| HME$_z$-α-CD | HME$_z$-β-CD | HME$_z$-γ-CD |
| HEE$_z$-α-CD | HEE$_z$-β-CD | HEE$_z$-γ-CD |
| HPE$_z$-α-CD | HPE$_z$-β-CD | HPE$_z$-γ-CD |
| HBE$_z$-α-CD | HBE$_z$-β-CD | HBE$_z$-γ-CD |
| HPtE$_z$-α-CD | HPtE$_z$-β-CD | HPtE$_z$-γ-CD |
| HHE$_z$-α-CD | HHE$_z$-β-CD | HHE$_z$-γ-CD | wherein HME denotes hydroxymethyl ether, HEE denotes hydroxyethyl ether, HPE denotes hydroxypropyl ether, HBE denotes hydroxybutyl ether, HPtE denotes hydroxypentyl ether, HHE denotes hydroxyhexyl ether, and z denotes the single degree of substitution.

A water-soluble fractionated alkylated cyclodextrin composition can comprise a sulfoalkyl-ether alkyl-ether cyclodextrin (SAE-AE-CD) compound, or mixture of compounds, of Formula VII:

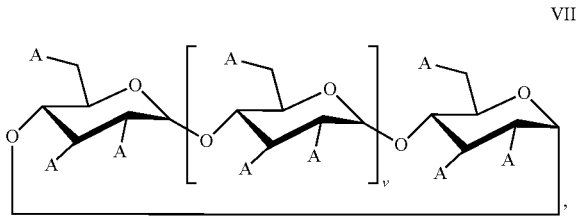

VII wherein: v is 4, 5 or 6; A is independently selected at each occurrence from the group consisting of —OH, -SAE-T and -AE; x is the single degree of substitution for the SAE-T moiety and is 1 to 3v+5; y is the single degree of substitution for the AE moiety and is 1 to 3v+5; -SAE is —O—($C_2$-$C_6$ alkylene)-$SO_3^-$; T is independently at each occurrence a cation; and AE is —O($C_1$-$C_3$ alkyl); provided that at least one -SAE-T moiety and at least one -AE moiety are present; and the sum of x, y and the total number of —OH groups in an alkylated cyclodextrin is 3v+6.

Specific embodiments of the derivatives described herein include those wherein: 1) the alkylene moiety of the SAE has the same number of carbons as the alkyl moiety of the AE; 2) the alkylene moiety of the SAE has a different number of carbons than the alkyl moiety of the AE; 3) the alkyl and alkylene moieties are independently selected from the group consisting of a straight chain or branched moiety; 4) the alkyl and alkylene moieties are independently selected from the group consisting of a saturated or unsaturated moiety; 5) the single degree of substitution for the SAE group is greater than or approximates the single degree of substitution for the AE group; or 6) the single degree of substitution for the SAE group is less than the single degree of substitution for the AE group.

A water-soluble fractionated alkylated cyclodextrin composition can comprise a sulfoalkyl ether hydroxyalkyl ether cyclodextrin (SAE-HAE-CD) compound, or mixture of compounds, of Formula VIII:

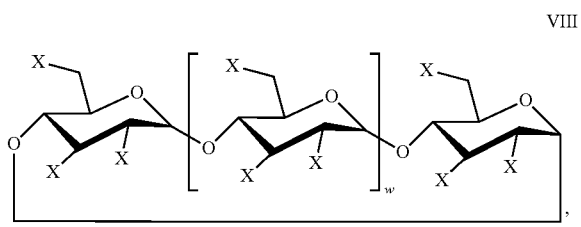

VIII wherein: w is 4, 5 or 6; X is independently selected at each occurrence from the group consisting of —OH, SAE-T and HAE; x is the single degree of substitution for the SAE-T moiety and is 1 to 3w+5; y is the single degree of substitution for the HAE moiety and is 1 to 3w+5; -SAE is —O—($C_2$-$C_6$ alkylene)-$SO_3^+$; T is independently at each occurrence a cation; and HAE is HO—($C_1$-$C_6$ alkyl)-O—; provided that at least one -SAE-T moiety and at least one -HAE moiety are present; and the sum of x, y and the total number of —OH groups in an alkylated cyclodextrin is 3w+6.

The fractionated alkylated cyclodextrin can include SAE-CD, HAE-CD, SAE-HAE-CD, HANE-CD, HAE-AE-CD, HAE-SAE-CD, AE-CD, SAE-AE-CD, neutral cyclodextrin, anionic cyclodextrin, cationic cyclodextrin, halo-derivatized cyclodextrin, amino-derivatized cyclodextrin, nitrile-derivatized cyclodextrin, aldehyde-derivatized cyclodextrin, carboxylate-derivatized cyclodextrin, sulfate-derivatized cyclodextrin, sulfonate-derivatized cyclodextrin, mercapto-derivatized cyclodextrin, alkylamino-derivatized cyclodextrin, or succinyl-derivatized cyclodextrin.

Within a given fractionated alkylated cyclodextrin composition, the substituents of the fractionated alkylated cyclodextrin(s) thereof can be the same or different. For example, SAE or HAE moieties can have the same type or different type of alkylene (alkyl) radical upon each occurrence in a fractionated alkylated cyclodextrin composition. In such embodiments, the alkylene radical in the SAE or HAE moiety can be ethyl, propyl, butyl, pentyl or hexyl in each occurrence in a fractionated alkylated cyclodextrin composition.

The regiochemistry of substitution of the hydroxyl groups of the fractionated alkylated cyclodextrin is variable with regard to the substitution of specific hydroxyl groups of the ring. For this reason, substitution of the different hydroxyl groups is likely to occur during manufacture of the derivatized cyclodextrin, and a particular derivatized cyclodextrin will possess a preferential, although not exclusive or specific, substitution pattern.

In a single parent cyclodextrin molecule, there are 3v+6 hydroxyl moieties available for derivatization. Where v=4 (α-cyclodextrin), y, the single degree of substitution for the moiety, can range in value from 1 to 18. Where v=5 (β-cyclodextrin), y, the single degree of substitution for the moiety, can range in value from 1 to 21. Where v=6 (γ-cyclodextrin), y, the single degree of substitution for the moiety, can range in value from 1 to 24. In general, y also ranges in value from 1 to 3v+g, where g ranges in value from 0 to 5. In some embodiments, y ranges from 1 to 2v+g, or from 1 to 1v+g.

The parent cyclodextrin includes a secondary hydroxyl group on the C-2 and C-3 positions of the glucopyranose residues forming the cyclodextrin and a primary hydroxyl on the C-6 position of the same. Each of these hydroxyl moieties is available for derivatization by substituent precursor. Depending upon the synthetic methodology employed, the substituent moieties can be distributed randomly or in a somewhat ordered manner among the available hydroxyl positions. The regioisomerism of derivatization by the substituent can also be varied as desired. The regioisomerism of each composition is independently selected. For example, a majority of the substituents present can be located at a primary hydroxyl group or at one or both of the secondary hydroxyl groups of the parent cyclodextrin. In some embodiments, the primary distribution of substituents is C-3>C-2>C-6, while in other embodiments the primary distribution of substituents is C-2>C-3>C-6. Some embodiments include a fractionated alkylated cyclodextrin molecule wherein a minority of the substituent moieties is located at the C-6 position, and a majority of the substituent moieties is located at the C-2 and/or C-3 position. Still other embodiments include a fractionated alkylated cyclodextrin molecule wherein the substituent moieties are substantially evenly distributed among the C-2, C-3, and C-6 positions.

The above-mentioned variations among the individual species of alkylated cyclodextrins in a distribution can lead to changes in the complexation equilibrium constant $K_{1:1}$ which in turn will affect the required molar ratios of the derivatized cyclodextrin to active agent. The equilibrium constant is also somewhat variable with temperature and allowances in the ratio are required such that the agent remains solubilized during the temperature fluctuations that can occur during manufacture, storage, transport, and use. The equilibrium constant can also vary with pH and allowances in the ratio can be required such that the agent remains solubilized during pH fluctuations that can occur during manufacture, storage, transport, and use. The equilibrium constant can also vary due the presence of other excipients (e.g., buffers, preservatives, antioxidants). Accordingly, the ratio of derivatized cyclodextrin to active agent can be varied from the ratios set forth herein in order to compensate for the above-mentioned variables.

The fractionated alkylated cyclodextrins described herein can be employed in compositions, formulations, methods and systems such as those disclosed in U.S. Pat. Nos. 5,134,127, 5,376,645, 5,914,122, 5,874,418, 6,046,177, 6,133,248, 6,153,746, 6,407,079, 6,869,939, 7,034,013, 7,625,878, 7,629,331, and 7,635,773; U.S. Pub. Nos. 2005/0164986, 2005/0186267, 2005/0250738, 2006/0258537, 2007/0020196, 2007/0020298, 2007/0020299, 2007/0175472, 2007/0202054, 2008/0194519, 2009/0011037, 2009/0012042, and 2009/0123540; U.S. application Ser. Nos. 12/404,174, 12/407,734, 61/050,918, 61/177,718, and 61/182,560; and PCT International Application Nos. PCT/US06/62346, PCT/US07/71758, PCT/US07/71748, PCT/US07/72387, PCT/US07/72442, PCT/US07/78465, PCT/US08/61697, PCT/US08/61698, PCT/US08/70969, and PCT/US08/82730, the entire disclosures of which are hereby incorporated by reference. The fractionated alkylated cyclodextrins prepared according to the processes herein can also be used as suitable substitutes for other known grades of alkylated cyclodextrins possessing the same functional groups.

In some embodiments, a fractionated alkylated cyclodextrin possesses greater water solubility than a corresponding cyclodextrin from which a fractionated alkylated cyclodextrin composition is prepared. For example, in some embodiments, an underivatized cyclodextrin is utilized as a starting material, e.g., α-, β- or γ-cyclodextrin, commercially available from, e.g., Wacker Biochem Corp. (Adrian, Mich.), and other sources. Underivatized cyclodextrins have limited water solubility compared to the alkylated cyclodextrins compositions described herein. For example, underivatized α-CD, β-CD, γ-CD have a solubility in water solubility of about 145 g/L, 18.5 g/L, and 232 g/L, respectively, at saturation.

The water-soluble fractionated alkylated cyclodextrin composition is optionally processed to remove a major portion (e.g., >50% by weight) of an underivatized cyclodextrin, or other contaminants.

The terms "alkylene" and "alkyl," as used herein (e.g., in the —O—($C_2$-$C_6$-alkylene)$SO_3^-$ group or in the alkylamine cations), include linear, cyclic, and branched, saturated and unsaturated (i.e., containing one or more double bonds), divalent alkylene groups and monovalent alkyl groups, respectively. For example, SAE or HAE moieties can have the same type or different type of alkylene (alkyl) radical upon each occurrence in an alkylated cyclodextrin composition. In such embodiments, the alkylene radical in the SAE or HAE moiety can be ethyl, propyl, butyl, pentyl or hexyl in each occurrence in a fractionated alkylated cyclodextrin composition.

The term "alkanol" in this text likewise includes both linear, cyclic and branched, saturated and unsaturated alkyl components of the alkanol groups, in which the hydroxyl groups can be situated at any position on the alkyl moiety. The term "cycloalkanol" includes unsubstituted or substituted (e.g., by methyl or ethyl) cyclic alcohols.

In some embodiments, the disclosure is directed to the following Particular Embodiments:

I. A fractionated alkylated cyclodextrin composition comprising 60% by weight or more alkylated cyclodextrin having a single degree of substitution relative to all alkylated cyclodextrin in the composition.

II. The composition of Particular Embodiment I, wherein the single degree of substitution is 1, 2, 3, 4, 5, 6, 7, 8, 9, 10, 11, or 12.

III. The composition of Particular Embodiment I or II, wherein the fractionated alkylated cyclodextrin composition comprises 70% by weight or more alkylated cyclodextrin having a single degree of substitution relative to all alkylated cyclodextrin in the composition.

IV. The composition of Particular Embodiment I or II, wherein the fractionated alkylated cyclodextrin composition comprises 80% by weight or more alkylated cyclodextrin having a single degree of substitution relative to all alkylated cyclodextrin in the composition.

V. The composition of any one of Particular Embodiments I-IV, wherein the alkylated cyclodextrin is a sulfoalkyl ether cyclodextrin of Formula (II):

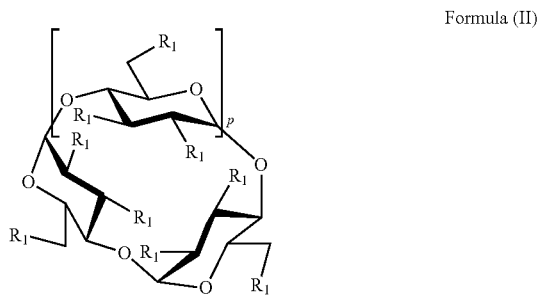

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

VI. The composition of Particular Embodiment V, wherein $R_1$ is independently selected at each occurrence from —OH or —O—($C_4$ alkylene)-$SO_3^-$-T, and -T is $Na^+$ at each occurrence.

VII. A composition comprising the fractionated alkylated cyclodextrin composition of any one of Particular Embodiments I-VI and one or more excipients.

VIII. A composition comprising the fractionated alkylated cyclodextrin composition of any one of Particular Embodiments I-VI and an active agent.

IX. A combination composition comprising a mixture of at least two different fractionated alkylated cyclodextrins, the mixture comprising:
(a) a first fractionated alkylated cyclodextrin having a single degree of substitution;
(b) a second fractionated alkylated cyclodextrin,
wherein the first fractionated alkylated cyclodextrin composition and the second fractionated alkylated cyclodextrin composition are different and the combination of the first and second fractionated alkylated cyclodextrin is 60% by weight or more of all alkylated cyclodextrin in the composition.

X. The combination composition of Particular Embodiment IX, wherein the single degree of substitution of the first fractionated alkylated cyclodextrin differs from the single degree of substitution of the second fractionated alkylated cyclodextrin by at least 1, 2, 3, 4, 5, 6, 7, 8, 9, 10, or 11.

XI. The combination composition of Particular Embodiment IX or X, wherein substituents on the first fractionated alkylated cyclodextrin and substituents on the second fractionated alkylated cyclodextrin are different.

XII. The combination composition of Particular Embodiment IX or X, wherein substituents on the first fractionated alkylated cyclodextrin and substituents on the second fractionated alkylated cyclodextrin are the same.

XIII. The combination composition of any one of Particular Embodiments IX-XII, wherein the first fractionated alkylated cyclodextrin, the second fractionated alkylated cyclodextrin, or both the first and second fractionated alkylated cyclodextrin is a sulfoalkyl ether cyclodextrin of Formula (II):

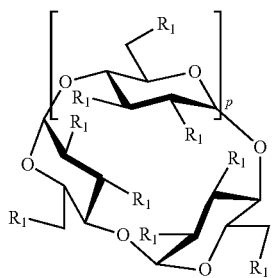

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

XIV. The combination composition of Particular Embodiment XIII, wherein $R_1$ is independently selected at each occurrence from —OH or —O—($C_4$ alkylene)-$SO_3^-$-T, and -T is $Na^+$ at each occurrence.

XV. The combination composition of any one of Particular Embodiments IX-XIV, wherein the combination composition further comprises one or more excipients.

XVI. The combination composition of any one of Particular Embodiments IX-XV, wherein the combination composition further comprises an active agent.

XVII. A process for preparing a fractionated alkylated cyclodextrin composition comprising an alkylated cyclodextrin, the process comprising:
(a) preparing a solution comprising an alkylated cyclodextrin composition;
(b) passing the solution through a chromatographic separation system having a stationary phase and a mobile phase; and
(c) collecting a fractionated alkylated cyclodextrin composition comprising 60% by weight or more alkylated cyclodextrin having a selected single degree of substitution relative to all alkylated cyclodextrin in the composition.

XVIII. The process of Particular Embodiment XVII, wherein the chromatographic separation system is high performance liquid chromatography.

XIX. The process of Particular Embodiment XVII, wherein the chromatographic separation system is reversed phase high performance liquid chromatography.

XX. The process of any one of Particular Embodiments XVII-XIX, wherein the stationary phase is a silica gel column.

XXI. The process of any one of Particular Embodiments XVII-XX, wherein the mobile phase comprises acetonitrile.

XXII. The process of Particular Embodiment XXI, wherein the mobile phase further comprises an ammonium acetate buffer.

XXII. The process of any one of Particular Embodiments XVII-XXII, wherein the single degree of substitution is 1, 2, 3, 4, 5, 6, 7, 8, 9, 10, 11, or 12.

XXIV. The process of any one of Particular Embodiments XVII-XXIII, wherein the fractionated alkylated cyclodextrin composition comprises 70% by weight or more alkylated cyclodextrin having a single degree of substitution relative to all alkylated cyclodextrin in the composition.

XXV. The process of any one of Particular Embodiments XVII-XXIII, wherein the fractionated alkylated cyclodextrin composition comprises 80% by weight or more alkylated cyclodextrin having a single degree of substitution relative to all alkylated cyclodextrin in the composition.

XVI. The process of any one of Particular Embodiments XVII-XXV, wherein the alkylated cyclodextrin is a sulfoalkyl ether cyclodextrin of Formula (II):

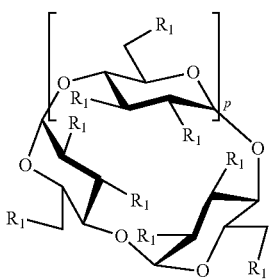

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

XXVII. The process of Particular Embodiment XVI, wherein $R_1$ is independently selected at each occurrence from —OH or —O—($C_4$ alkylene)-$SO_3^-$-T, and -T is $Na^+$ at each occurrence.

XXVIII. The process of any one of Particular Embodiments XVII-XXVII, further comprising combining the fractionated alkylated cyclodextrin composition with one or more excipients.

XXIX. The process of any one of Particular Embodiments XVII-XXVIII, further comprising combining the fractionated alkylated cyclodextrin composition with an active agent.

XXX. A product prepared by the process of any one of Particular Embodiments XVII-XXIX.

Preparation of Alkylated Cyclodextrin Compositions

In some embodiments, the alkylated cyclodextrin composition prior to fractionation is a sulfoalkyl ether-β-cyclodextrin composition having an ADS of 2 to 9, 4 to 8, 4 to 7.5, 4 to 7, 4 to 6.5, 4.5 to 8, 4.5 to 7.5, 4.5 to 7, 5 to 8, 5 to 7.5, 5 to 7, 5.5 to 8, 5.5 to 7.5, 5.5 to 7, 5.5 to 6.5, 6 to 8, 6 to 7.5, 6 to 7.1, 6.5 to 7.1, 6.2 to 6.9, or 6.5 per alkylated cyclodextrin, and the remaining substituents are —H.

In some embodiments, the alkylated cyclodextrin composition prior to fractionation include those wherein: 1) more than half of the hydroxyl moieties of the alkylated cyclodextrin are derivatized; 2) half or less than half of the hydroxyl moieties of the alkylated cyclodextrin are derivatized; 3) the substituents of the alkylated cyclodextrin are the same upon each occurrence; 4) the substituents of the alkylated cyclodextrin comprise at least two different substituents; or 5) the substituents of the alkylated cyclodextrin comprise one or more substituents selected from the group consisting of unsubstituted alkyl, substituted alkyl, halide (halo), haloalkyl, amine (amino), aminoalkyl, aldehyde, carbonylalkyl, nitrile, cyanoalkyl, sulfoalkyl, hydroxyalkyl, carboxyalkyl, thioalkyl, unsubstituted alkylene, substituted alkylene, aryl, arylalkyl, heteroaryl, and heteroarylalkyl.

The alkylated cyclodextrin compositions prior to fractionation can comprise plural individual alkylated cyclodextrin species differing in individual degree of substitution, such that the average degree of substitution is calculated, as described herein, from the individual degrees of substitution of the species. More specifically, a SAE-CD derivative composition can comprise plural SAE-CD species each having a specific individual degree of substitution with regard to the SAE substituent. As a consequence, the ADS for SAE of a SAE-CD derivative composition represents an average of the IDS values of the population of individual molecules in the composition. For example, a $SAE_{5.2}$-CD composition comprises a distribution of plural $SAE_x$-CD molecules, wherein x (the DS for SAE groups) can range from 1 to 10-11 for individual cyclodextrin molecules; however, the population of SAE-cyclodextrin molecules is such that the average value for x (the ADS for SAE groups) is 5.2.

The alkylated cyclodextrin compositions prior to fractionation can have a high to moderate to low ADS. The alkylated cyclodextrin compositions can also have a wide or narrow "span," which is the number of individual DS species within an alkylated cyclodextrin composition. For example, an alkylated cyclodextrin composition comprising a single species of alkylated cyclodextrin having a single specified individual DS is said to have a span of one, and the individual DS of the alkylated cyclodextrin equals the ADS of its alkylated cyclodextrin composition. An electropherogram, for example, of an alkylated cyclodextrin with a span of one should have only one alkylated cyclodextrin species with respect to DS. An alkylated cyclodextrin composition having a span of two comprises two individual alkylated cyclodextrin species differing in their individual DS, and its electropherogram, for example, would indicate two different alkylated cyclodextrin species differing in DS. Likewise, the span of an alkylated cyclodextrin composition having a span of three comprises three individual alkylated cyclodextrin species differing in their individual DS. The span of an alkylated cyclodextrin composition typically ranges from 5 to 15, or 7 to 12, or 8 to 11. An alkylated cyclodextrin composition comprises a distribution of plural individual alkylated cyclodextrin species, each species having an individual degree of substitution ("IDS"). The content of each of the cyclodextrin species in a particular composition can be quantified using capillary electrophoresis. The method of analysis (capillary electrophoresis, for example, for charged alkylated cyclodextrins) is sufficiently sensitive to distinguish between compositions having only 5% by weight of one alkylated cyclodextrin and 95% by weight of another alkylated cyclodextrin from starting alkylated cyclodextrin compositions containing.

The alkylated cyclodextrin composition can be prepared using any method. In general, an underivatized cyclodextrin starting material in neutral to alkaline aqueous media is exposed to substituent precursor. The substituent precursor can be added incrementally or as a bolus, and the substituent precursor can be added before, during, or after exposure of the cyclodextrin starting material to the optionally alkaline aqueous media. Additional alkaline material or buffering material can be added as needed to maintain the pH within a desired range. The derivatization reaction can be conducted at ambient to elevated temperatures. Once derivatization has proceeded to the desired extent, the reaction is optionally quenched by addition of an acid. The reaction milieu is further processed (e.g., solvent precipitation, filtration, centrifugation, evaporation, concentration, drying, chromatography, dialysis, and/or ultrafiltration) to remove undesired materials such as remaining starting materials or by-products and form the target composition.

Also provided is a process of making an alkylated cyclodextrin composition comprising an alkylated cyclodextrin, optionally having a pre-determined average degree of substitution, the process comprising: combining an unsubstituted cyclodextrin starting material with an alkylating agent in an amount sufficient to effect the pre-determined degree of substitution, in the presence of an alkali metal hydroxide; conducting alkylation of the cyclodextrin within a pH of 9 to 11 until residual unreacted cyclodextrin is less than 0.5% by weight, or less than 0.1% by weight; adding additional hydroxide in an amount sufficient to achieve the degree of substitution and allowing the alkylation to proceed to completion; and adding additional hydroxide to destroy any residual alkylating agent.

Adding an additional hydroxide can be conducted using a quantity of hydroxide, and under conditions (i.e., amount of additional hydroxide added, temperature, length of time during which the alkylating agent hydrolysis is conducted) such that the level of residual alkylating agent in the aqueous crude product is reduced to less than 20 ppm or less than 2 ppm.

It is possible that the reaction milieu or the partially purified aqueous solution will comprise unreacted alkylating agent. The alkylating agent can be degraded in situ by adding additional alkalizing agent or by heating a solution containing the agent. Degrading an excess alkylating agent will be required where unacceptable amounts of alkylating agent are present in the reaction milieu following termination of the mixing. The alkylating agent can be degraded in situ by adding additional alkalizing agent or by heating a solution containing the agent.

Degrading can be conducted by: exposing the reaction milieu to an elevated temperature of at least 60° C., at least 65° C., or 60° C. to 85° C., 60° C. to 80° C., or 60° C. to 95° C. for a period of at least 6 hours, at least 8 hours, 8 hours to 12 hours, 6 hours to 72 hours, or 48 hours to 72 hours, thereby degrading the alkylating agent in situ and reducing the amount of or eliminating the alkylating agent in the aqueous liquid.

After the reaction has been conducted as described herein, the aqueous medium containing the alkylated cyclodextrin can be neutralized to a pH of 7 in order to quench the reaction. The solution can then be diluted with water in order to lower viscosity, particularly if further purification is to be conducted. Further purifications can be employed, including, but not limited to, diafiltration on an ultrafiltration unit to purge the solution of reaction by-products such as salts (e.g., NaCl if sodium hydroxide was employed as the base) and other low molecular weight by-products. The product can further be concentrated by ultrafiltration. The product solution can then be treated with activated carbon in order to improve its color, reduce bioburden, and substantially remove one or more UV-active impurities, which may have drug degrading properties. The product can be isolated by a suitable drying technique such as freeze drying, spray drying, or vacuum drum drying.

The reaction can initially be prepared by dissolving an unsubstituted α-, β-, or γ-cyclodextrin starting material in an aqueous solution of base, usually a hydroxide such as lithium, sodium, or potassium hydroxide. The base is present in a catalytic amount (i.e., a molar ratio of less than 1:1 relative to the cyclodextrin), to achieve a pre-determined or desired degree of substitution. That is, the base is present in an amount less than one molar equivalent for each hydroxyl sought to be derivatized in the cyclodextrin molecule. Because cyclodextrins become increasingly soluble in aqueous solution as the temperature is raised, the aqueous reaction mixture containing base and cyclodextrin should be raised to a temperature of 50° C. to ensure complete dissolution. Agitation is generally employed throughout the course of the alkylation reaction.

After dissolution is complete, the alkylating agent is added to start the alkylation reaction. The total amount of alkylating agent added throughout the reaction will generally be in excess of the stoichiometric amount required to complete the reaction relative to the amount of cyclodextrin, since some of the alkylating agent is hydrolyzed and/or otherwise destroyed/degraded during the reaction such that it is not available for use in the alkylation reaction. The exact amount of alkylating agent to use for a desired degree of substitution can be determined through the use of trial runs. The entire amount of alkylating agent needed to complete the reaction can be added prior to initiating the reaction. Because the system is aqueous, the reaction is generally conducted at a temperature 50° C. and 100° C. The reaction can be conducted at a temperature less than 100° C., so that specialized pressure equipment is not required. In general, a temperature of 65° C. to 95° C. is suitable.

During the initial phase of the reaction (herein referred to as the pH-control phase), care should be taken to monitor the pH and maintain it at least basic, or at a pH of 8 to 11. Monitoring of pH can be effected conventionally by using a standard pH meter. Adjustment of the pH can be effected by adding an aqueous solution of hydroxide, e.g., a 10-15% solution. During the initial pH-control phase, unreacted cyclodextrin is reacted to the extent that less than 0.5% by weight, or less than 0.1% by weight, of unreacted cyclodextrin remains in solution. Substantially the entire initial charge of cyclodextrin is thus reacted by being partially substituted, but to less than the desired pre-determined degree of substitution. Residual cyclodextrin can be monitored throughout this initial phase, for example by HPLC as described below, until a desired endpoint of less than 0.5% by weight, or less than 0.1% by weight, of residual cyclodextrin starting material, has been achieved. The pH can be maintained and/or raised by adding concentrated hydroxide to the reaction medium continuously or in discrete amounts as small increments. Addition in small increments is particularly suitable.

Once an alkylation procedure has been standardized or optimized so that it is known that particular amounts of reactants can be combined in a procedure which produces the desired degree of substitution in conjunction with low residual cyclodextrin, then the procedure can simply be checked at the end, as opposed to throughout or during the initial pH-control, to ensure that a low level of residual (unreacted) cyclodextrin starting material has been achieved. The following table sets forth a relationship between the amount of butane sultone charged into a reactor and the resulting average degree of substitution of the SAE-CD.

| Butane Sultone Charged (Approximate equivalents of BS per mole of cyclodextrin) | Corresponding Approximate Predetermined ADS for SAE-CD formed |
|---|---|
| 2 | 2 |
| 3 | 3 |
| 4 | 4 |
| 5 | 5 |
| 6 | 5-5.5 |
| 7 | 5.5 to 6.5 |
| 8 | 6.5 to 7 |
| 9 | 7-8 |
| 12 | 8-9 |

It is noted that the initial pH of the reaction medium can be above 11, for example after combining the initial charge of cyclodextrin starting material and base, but prior to addition of alkylating agent. After an alkylating agent has been added and the reaction commences, however, the pH quickly drops, necessitating addition of base to maintain a basic pH of about 8 to about 11.

Once the level of residual unreacted cyclodextrin has reached a desired level, e.g., below 0.5% by weight, during the pH control stage, the pH can be raised to above 11, for example a level above 12, by adding additional base to drive the reaction to completion. The pH can be at least 12 so that the reaction proceeds at a reasonable rate, but not so high that unreacted alkylating agent is hydrolyzed rapidly rather than reacting with cyclodextrin. During this latter phase of the reaction, additional substitution of the cyclodextrin molecule is effected until the pre-determined degree of substitution has been attained. The total amount of hydroxide added throughout the reaction is typically on the order of the amount stoichiometrically required plus a 10-20% molar excess relative to the amount of alkylating agent employed. The addition of more than a 10-20% excess is also feasible. The reaction end point, as noted above, can be detected by HPLC.

Once the alkylation reaction is complete and the low residual cyclodextrin end point has been reached, additional hydroxide can be added to destroy and/or degrade any residual alkylating agent. The additional hydroxide is typically added in an amount of 0.5 to 3 molar equivalents relative to cyclodextrin, and the reaction medium is allowed to continue heating at 65° C. to 95° C., typically for 6 hours to 72 hours.

After residual alkylating agent destruction, the resulting crude product can be diluted, diafiltered to reduce or rid the product of low molecular weight components such as salts, concentrated, carbon treated, and dried.

Reduction and Removal of Impurities in an Alkylated Cyclodextrin Composition

Initial pH control provides a means for reducing certain by-products from the reaction mixture. For example, an acid is produced as a result of the alkylation and the pH of the reaction mixture tends to decrease (i.e., become more acidic) as the reaction proceeds. On one hand, the reaction is maintained basic because if the reaction medium becomes acidic, then the reaction will slow considerably or stop. Accordingly, the pH of the reaction medium should be maintained at a level of at least 8 by adding aqueous hydroxide as needed. On the other hand, if the pH is allowed to exceed a certain level, for example, a pH greater than 12, then the reaction can produce a high level of by-products such as 4-hydroxyalkylsulfonate and bis-sulfoalkyl ether, thus consuming the alkylating agent starting material. By monitoring the pH of the reaction solution and maintaining the pH at 8 to 12, or 8 to 11, the reaction proceeds while producing a relatively low-level of by-products, and a relatively clean reaction mixture containing relatively low levels of the aforementioned by-products is provided.

Typically, the crude aqueous cyclodextrin product solution obtained following residual alkylating agent destruction is purified by ultrafiltration, a process in which the crude product is contacted with a semipermeable membrane that passes low molecular weight impurities through the membrane. The molecular weight of the impurities passed through the membrane depends on the molecular weight cut-off for the membrane. A membrane having a molecular weight cutoff of 1,000 Daltons ("Da") can typically be employed. Diafiltrations and/or ultrafiltrations can be conducted with filtration membranes having a molecular weight cut-off of 500 Da to 2,000 Da, 500 Da to 1,500 Da, 750 Da to 1,250 Da, or 900 Da to 1,100 Da, or about 1,000 Da. The desired product which is in the retentate is then further treated with activated carbon to substantially remove drug-degrading impurities. The crude aqueous cyclodextrin product solution (i.e., obtained after residual alkylating agent destruction but before purification) is advantageous in that it contains less than 2 ppm residual alkylating agent based on the weight of the solution, less than 1 ppm, or less than 250 ppb. The crude solution can also contain essentially no residual alkylating agent.

Activated carbon suitable for use can be phosphate-free, and can be powder or granular, or a suspension or slurry produced therefrom. Generally, phosphate-free activated carbon is a carbon that was not activated using, or otherwise exposed to, phosphoric acid.

A wide variety of activated carbon is available. For example, Norit-Americas commercializes over 150 different grades and varieties of activated carbon under trademarks such as Darco®, Hydrodarco®, Norit®, Bentonorit®, Petrodarco®, and Sorbonorit®. The carbons differ in particle size, application, method of activation, and utility. For example, some activated carbons are optimized for color and/or flavor removal. Other activated carbons are optimized for removal of protein, mineral, and/or amino acid moieties, or for clarifying solutions.

Activated carbons suitable for use include, but are not limited to: Darco® 4×12, 12×20, or 20×40 granular from lignite, steam activated (Norit Americas, Inc., Marshall, Tex.); Darco® S 51 HF (from lignite, steam activated, powder); and Shirasagi® DC-32 (Takeda Chemical Industries, Ltd., Osaka, JP) powered or granular carbon from wood, zinc chloride activated.

Carbon that is activated with phosphoric acid, as used in the prior art for purifying alkyl ether cyclodextrins, is generally unsuitable, and includes: Darco® KB-G (Norit Americas Inc., Marshall, Tex.), Darco® KB-B (Norit Americas Inc., Marshall, Tex.), and Darco® KB-WJ (Norit Americas Inc., Marshall, Tex.), as well as Norit® CASP (Norit Americas Inc., Marshall, Tex.) and Norit® CN1 (Norit Americas Inc., Marshall, Tex.).

The loading ratio of activated carbon ultimately depends upon the amount or concentration of the alkylated cyclodextrin, color-forming agents, and UV-active impurities in solution as well as the physical properties of the activated carbon used. In general, the weight ratio of a cyclodextrin to activated carbon is 5:1 to 10:1, 6:1 to 9:1, 7:1 to 9:1, 8:1 to 9:1, 8.3:1 to 8.5:1, 8.4:1 to 8.5:1, or 8.44:1 by weight per treatment cycle.

As used herein, "treatment cycle" refers to contacting a predetermined amount of a cyclodextrin composition with a predetermined amount of activated carbon. A treatment cycle can be performed as a single treatment or as a multiple (recycling) pass-through treatment.

In general, an in-process milieu or solution is treated with activated carbon and agitated for 120 min. If a loose, particulate, or powdered form of activated carbon is used, it can be removed by filtration of a liquid containing the carbon through a filtration medium to provide the clarified solution.

The filtration membrane can include nylon, Teflon®, PVDF, or another compatible material. The pore size of the filtration membrane can be varied as needed according to the particle size or molecular weight of species being separated from the alkylated cyclodextrin in solution.

A reaction solution is diluted with aqueous solution and subjected to diafiltration during which the volume of the retentate is maintained substantially constant. The diafiltration can be conducted over a 1,000 Da filter such that one or more unwanted components pass through the filter but the majority of the alkyl ether present in the alkylated cyclodextrin composition is retained in the retentate rather than passing through with the filtrate. The ultrafiltration is then conducted by allowing the volume of the retentate to decrease thereby concentrating the retentate. A filter having a molecular weight cut-off of about 1,000 Da can also be used for the ultrafiltration. The retentate comprises the alkylated cyclodextrin, which can then be treated with activated carbon as described herein.

The one or more unwanted components can include, but are not limited to, low molecular weight impurities (i.e., impurities having a molecular weight of about 500 Da or less), water-soluble and/or water-insoluble ions (i.e., salts), hydrolyzed alkylating agent, 5-(hydroxymethyl)-2-furaldehyde, unreacted cyclodextrin starting material, degraded cyclodextrin species (e.g., degraded and/or ring-opened species formed from unreacted cyclodextrin, partially reacted cyclodextrin, and/or SAE-CD), unreacted alkylating agent (e.g., 1,4-butane sultone), and combinations thereof.

The final yield of the alkylated cyclodextrin (in isolated and/or purified or partially purified form) obtained at completion of the process will vary. The final yield of alkylated cyclodextrin based on the cyclodextrin starting material can range from 10% to 95%, 10% to 90%, 10% to 80%, 10% to 70%, 10% to 60%, 10% to 50%, 10% to 40%, 10% to 30%, 10% to 20%, 20% to 95%, 20% to 90%, 20% to 80%, 20% to 70%, 20% to 60%, 20% to 50%, 20% to 40%, 20% to 30%, 30% to 95%, 30% to 90%, 30% to 80%, 30% to 70%, 30% to 60%, 30% to 50%, 30% to 40%, 40% to 95%, 40% to 90%, 40% to 80%, 40% to 70%, 40% to 60%, 40% to 50%, 50% to 95%, 50% to 90%, 50% to 80%, 50% to 70%, 50% to 60%, 60% to 95%, 60% to 90%, 60% to 80%, 60% to 70%, 70% to 95%, 70% to 90%, 70% to 80%, 80% to 95%, 80% to 90%, or 90% to 95%. In some embodiments, the final yield of alkylated cyclodextrin based on the cyclodextrin starting material is 10% or more, 20% or more, 30% or more, 40% or more, 50% or more, 60% or more, 70% or more, 80% or more, 90% or more, or 95% or more.

Fractionation of Alkylated Cyclodextrin Compositions

In the synthetic chemical/pharmaceutical excipient industry, the ability to separate and purify a product from a complex mixture is an important and necessary step in production. Chromatography is a separation process for any material with an affinity for an adsorbent material.

In some embodiments, a process is provided for preparing a fractionated alkylated cyclodextrin composition comprising an alkylated cyclodextrin, the process comprising:

(a) preparing a solution comprising an alkylated cyclodextrin composition;
(b) passing the solution through a chromatographic separation system having a stationary phase and a mobile phase; and
(c) collecting a fractionated alkylated cyclodextrin composition comprising 60% by weight or more alkylated cyclodextrin having a selected single degree of substitution relative to all alkylated cyclodextrin in the composition.

In some embodiments, the chromatographic separation system is a liquid chromatograph. In some embodiments, the chromatographic separation system is a high performance liquid chromatograph. In some embodiments, the chromatographic separation system is a reversed phase high performance liquid chromatograph. In some embodiments, the chromatographic separation system is a Series 20A Prominence HPLC (Shimadzu Scientific Instruments).

The ultimate goal of chromatography is to separate different components from a solution mixture. Typically, column chromatography is set up with pumps, flowing buffers and the solution sample through a column. The solutions and buffers pass through the column where a fraction collector collects the eluted samples. A fraction collector is a device that allows regular or specified samples to be taken from a column eluent and stored in a retrievable form. Prior to the fraction collection, the samples that are eluted from the column pass through a detector such as a spectrophotometer so that the concentration of the separated samples in the sample solution mixture can be determined. The fractions can be collected on a basis of time either at regular intervals or at specific times to collect specific mixture components. High performance liquid chromatography (HPLC) typically utilizes different types of stationary phases, a pump that moves the mobile phase(s) and analyte through the column, and a detector to provide a characteristic retention time for the analyte. It is a form of liquid chromatography that utilizes smaller column size, smaller media inside the column, and higher mobile phase pressures. The detector provides information related to the analyte in the form of a two dimensional plot of time and detector signal output known as a chromatogram. Analyte retention time varies depending on the strength of its interactions with the stationary phase, the ratio/composition of solvent(s) used, and the flow rate of the mobile phase. This data is a good way of determining the column's separation properties of that particular sample. The resolution of mixture components can be calculated from the chromatogram. The resolution of components expresses the extent of separation between the components of the mixture. The higher the resolution of the chromatogram, the better the extent of separation of the samples the column gives. Once the properties of the instrument parameters, column interactions with the sample mixture and subsequent chromatogram that describes the separation has been ascertained, then the collection program can be more defined. The fractions can be collected by monitoring the detector output and when a components starts to elute the fraction collector is activated and the component collected in a specific vial. When the detector signal returns to base line the column eluent is then directed to waste until the next component starts eluting. Fraction collectors are in common use with liquid chromatographs. They are used to collect samples for further purification, subsequent examination by spectroscopic techniques or for biological or organoleptic testing.

There are four major separation modes of high performance liquid chromatography: reversed phase chromatography, normal-phase and adsorption chromatography, ion exchange chromatography, and size-exclusion chromatography. In reversed phase chromatography, the stationary phase is non-polar; reversed phase chromatography is useful for the separation of non-polar, polar, ionizable, and ionic molecules. In normal-phase chromatography, the stationary phase is polar, normal-phase chromatography is useful for water-sensitive compounds, geometric isomers, cis-trans isomers, class separations, and chiral compounds. In ion exchange chromatography, the stationary phase contains ionic groups and the mobile phase is an aqueous buffer, ion exchange chromatography is useful for inorganic and organic anions and cations. In size-exclusion chromatography, molecules diffuse into the pores of a porous medium and separate based on their relative size compared to the medium; size-exclusion chromatography is useful for polymer characterization and separation of proteins.

The table below shows typical column loads, flow rates, and column sizes to be used when scaling from analytical to semi-preparative scale using a Breeze 2 or Alliance HPLC system (Waters Corporation, Milford, Mass.).

| Typical Column I.D. | Maximum Flow Rate | Sample Load |
|---|---|---|
| 2 to 19 mm | 22.5 mL/min | µg to 10 s of mg |
| 4.6 to 30 mm | 50 mL/min | mg to g |
| 4.6 to 50 mm | 150 mL/min | mg to g |
| 7.8 to 75 mm | 300 mL/min | mg to 10 s of g |

The table below shows typical column loads, flow rates, and column sizes to be used when scaling for preparative scale using a Flash 400 large-scale purification system (Biotage AB, Uppsala, Sweden). Commercial scale can use much larger column sizes and flow rates but employs the same principle for separation.

|  | Flash 400M | Flash 400 L |
|---|---|---|
| Cartridge Diameter | 400 mm | 400 mm |
| Cartridge Length | 30 cm | 60 cm |
| Flow Rate (typical) | 7 L/min | 7 L/min |
| Column Void Volume | 25 L | 50 L |
| Packing Weight (KP-Sil silica) | 20 kg | 40 kg |
| Sample Size |  |  |
| 20% Load (g/run) | 4000 | 8000 |
| 5% Load (g/run) | 1000 | 2000 |
| 1% Load (g/run) | 200 | 400 |

The chromatography conditions would be the same for all separations, with the column size and flow rates being modified. The system to pump the solvent onto the columns would be different and depend on the scale of purification.

The term "stationary phase" as used herein, refers to the part of the chromatographic separation system through which the mobile phase flows where distribution of the solutes between the phases occurs. The stationary phase may be a solid or a liquid that is immobilized or adsorbed on a solid. In some embodiments, the stationary phase is a column.

In some embodiments, the stationary phase is composed of silica. In some embodiments, the stationary phase is a octadecylsilane (C18) column. In some embodiments, the stationary phase is a octylsilane (C8) column. In some embodiments, the stationary phase is a Discovery C18 or C8

HPLC column (Supelco Analytical). In some embodiments, the stationary phase is a Ascentis C18 HPLC column (Supelco Analytical).

In some embodiments, the stationary phase is composed of an organic polymer for example, polystyrene. In some embodiments, the stationary phase is highly cross-linked styrene-divinylbenzene.

In some embodiments, the column length is 25 m or less, 20 m or less, 15 m or less, 10 m or less, 5 m or less, 3 m or less, 25 cm or less, 20 cm or less, 15 cm or less, 10 cm or less, 5 cm or less, or 3 cm or less. In some embodiments, the column length is 25 m, 20 m, 15 m, 10 m, 5 m, 3 m, 25 cm, 20 cm, 15 cm, 10 cm, 5 cm, or 3 cm. In some embodiments, the column length is 25 m to 3 cm, 25 m to 5 cm, 25 m to 10 cm, 25 m to 15 cm, 25 m to 20 cm, 25 m to 25 cm, 25 m to 3 m, 25 m to 5 m, 25 m to 10 m, 25 m to 15 m, 25 m to 20 m, 20 m to 3 cm, 20 m to 5 cm, 20 m to 10 cm, 20 m to 15 cm, 20 m to 20 cm, 20 m to 25 cm, 20 m to 3 m, 20 m to 5 m, 20 m to 10 m, 20 m to 15 m, 15 m to 3 cm, 15 m to 5 cm, 15 m to 10 cm, 15 m to 15 cm, 15 m to 20 cm, 15 m to 25 cm, 15 m to 3 m, 15 m to 5 m, 15 m to 10 m, 10 m to 3 cm, 10 m to 5 cm, 10 m to 10 cm, 10 m to 15 cm, 10 m to 20 cm, 10 m to 25 cm, 10 m to 3 m, 10 m to 5 m, 5 m to 3 cm, 5 m to 5 cm, 5 m to 10 cm, 5 m to 15 cm, 5 m to 20 cm, 5 m to 25 cm, 5 m to 3 m, 3 m to 3 cm, 3 m to 5 cm, 3 m to 10 cm, 3 m to 15 cm, 3 m to 20 cm, 3 m to 25 cm, 25 cm to 3 cm, 25 cm to 5 cm, 25 cm to 10 cm, 25 cm to 15 cm, 25 cm to 20 cm, 20 cm to 3 cm, 20 cm to 5 cm, 20 cm to 10 cm, 20 cm to 15 cm, 15 cm to 3 cm, 15 cm to 5 cm, 15 cm to 10 cm, 10 cm to 3 cm, 10 cm to 5 cm, or 5 cm to 3 cm. The internal diameter of the column influences the detection sensitivity and separation selectivity.

The internal diameter of the column influences the detection sensitivity and separation selectivity. In some embodiments, the internal diameter of the column is 5 m or less, 4 m or less, 3 m or less, 2 m or less, 1 m or less, 50 cm or less, 40 cm or less, 30 cm or less, 20 cm or less, 10 cm or less, 5 cm or less, 1 cm or less, 0.9 cm or less, 0.8 cm or less, 0.7 cm or less, 0.6 cm or less, 0.5 cm or less, 0.4 cm or less, 0.3 cm or less, 0.2 cm or less, or 0.1 cm or less. In some embodiments, the internal diameter of the column is 5 m, 4 m, 3 m, 2 m, 1 m, 50 cm, 40 cm, 30 cm, 20 cm, 10 cm, 5 cm, 1 cm, 0.9 cm, 0.8 cm, 0.7 cm, 0.6 cm, 0.5 cm, 0.4 cm, 0.3 cm, 0.2 cm, or 0.1 cm In some embodiments, the internal diameter of the column is 5 m to 0.1 cm, 5 m to 0.5 cm, 5 m to 1 cm, 5 m to 10 cm, 5 m to 20 cm, 5 m to 30 cm, 5 m to 40 cm, 5 m to 50 cm, 5 m to 1 m, 5 m to 2 m, 5 m to 3 m, 5 m to 4 m, 4 m to 0.1 cm, 4 m to 0.5 cm, 4 m to 1 cm, 4 m to 10 cm, 4 m to 20 cm, 4 m to 30 cm, 4 m to 40 cm, 4 m to 50 cm, 4 m to 1 m, 4 m to 2 m, 4 m to 3 m, 3 m to 0.1 cm, 3 m to 0.5 cm, 3 m to 1 cm, 3 m to 10 cm, 3 m to 20 cm, 3 m to 30 cm, 3 m to 40 cm, 3 m to 50 cm, 3 m to 1 m, 3 m to 2 m, 2 m to 0.1 cm, 2 m to 0.5 cm, 2 m to 1 cm, 2 m to 10 cm, 2 m to 20 cm, 2 m to 30 cm, 2 m to 40 cm, 2 m to 50 cm, 2 m to 1 m, 1 m to 0.1 cm, 1 m to 0.5 cm, 1 m to 1 cm, 1 m to 10 cm, 1 m to 20 cm, 1 m to 30 cm, 1 m to 40 cm, 1 m to 50 cm, 50 cm to 0.1 cm, 50 cm to 0.5 cm, 50 cm to 1 cm, 50 cm to 10 cm, 50 cm to 20 cm, 50 cm to 30 cm, 50 cm to 40 cm, 40 cm to 0.1 cm, 40 cm to 0.5 cm, 40 cm to 1 cm, 40 cm to 10 cm, 40 cm to 20 cm, 40 cm to 30 cm, 30 cm to 0.1 cm, 30 cm to 0.5 cm, 30 cm to 1 cm, 30 cm to 10 cm, 30 cm to 20 cm, 20 cm to 0.1 cm, 20 cm to 0.5 cm, 20 cm to 1 cm, 20 cm to 10 cm, 10 cm to 0.1 cm, 10 cm to 0.5 cm, 10 cm to 1 cm, 1 cm to 0.1 cm, 1 cm to 0.5 cm, or 0.5 cm to 0.1 cm.

The term "mobile phase" as used herein, refers to the phase that is moving in the bed, including the fraction of sample held by this phase. The term mobile phase encompasses the terms mobile phase A and mobile phase B.

The term "UV transparent" as used herein, means that the object allows all light to pass through.

In some embodiments, the mobile phase comprises an organic solvent, a buffer, and an ion pairing agent. In some embodiments, the mobile phase comprises an organic solvent and a buffer. In some embodiments, the mobile phase comprises an organic solvent and an ion pairing agent.

In some embodiments, the organic solvent is added to the mobile phase to lower the polarity. In some embodiments, the organic solvent is acetonitrile, ethanol, methanol, 1-propanol, 2-propanol, or water. In some embodiments, the solvent is UV transparent.

In some embodiments, the pH of the mobile phase is adjusted using a buffer. In some embodiments, the buffer is hydrochloric acid, phosphoric acid, trifluoroacetic acid, triethylammonium phosphate, ammonium acetate, or sodium hydroxide. In some embodiments, the buffer is UV transparent.

In some embodiments, the pH of the mobile phase is from 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, or 9 to 10.

In some embodiments, the concentration of the buffer in the mobile phase is from 0.01% to 0.1%, 0.01% to 0.09%, 0.01% to 0.08%, 0.01% to 0.07%, 0.01% to 0.06%, 0.01% to 0.05%, 0.01% to 0.04%, 0.01% to 0.03%, 0.01% to 0.02%, 0.02% to 0.1%, 0.02% to 0.09%, 0.02% to 0.08%, 0.02% to 0.07%, 0.02% to 0.06%, 0.02% to 0.05%, 0.02% to 0.04%, 0.02% to 0.03%, 0.03% to 0.1%, 0.03% to 0.09%, 0.03% to 0.08%, 0.03% to 0.07%, 0.03% to 0.06%, 0.03% to 0.05%, 0.03% to 0.04%, 0.04% to 0.1%, 0.04% to 0.09%, 0.04% to 0.08%, 0.04% to 0.07%, 0.04% to 0.06%, 0.04% to 0.05%, 0.05% to 0.1%, 0.05% to 0.09%, 0.05% to 0.08%, 0.05% to 0.07%, or 0.05% to 0.06%, 0.06% to 0.1%, 0.06% to 0.09%, 0.06% to 0.08%, 0.06% to 0.07%, 0.07% to 0.1%, 0.07% to 0.09%, 0.07% to 0.08%, 0.08% to 0.1%, 0.08% to 0.09%, or 0.09% to 0.1%. In some embodiments, the concentration of the buffer in the mobile phase is from 10 mM to 100 mM, 10 mM to 90 mM, 10 mM to 80 mM, 10 mM to 70 mM, 10 mM to 60 mM, 10 mM to 50 mM, 10 mM to 40 mM, 10 mM to 30 mM, 10 mM to 20 mM, 20 mM to 100 mM, 20 mM to 90 mM, 20 mM to 80 mM, 20 mM to 70 mM, 20 mM to 60 mM, 20 mM to 50 mM, 20 mM to 40 mM, 20 mM to 30 mM, 30 mM to 100 mM, 30 mM to 90 mM, 30 mM to 80 mM, 30 mM to 70 mM, 30 mM to 60 mM, 30 mM to 50 mM, 30 mM to 40 mM, 40 mM to 100 mM, 40 mM to 90 mM, 40 mM to 80 mM, 40 mM to 70 mM, 40 mM to 60 mM, 40 mM to 50 mM, 50 mM to 90 mM, 50 mM to 80 mM, 50 mM to 70 mM, 50 mM to 60 mM, 60 mM to 100 mM, 60 mM to 90 mM, 60 mM to 80 mM, 60 mM to 70 mM, 70 mM to 100 mM, 70 mM to 90 mM, 70 mM to 80 mM, 80 mM to 100 mM, 80 mM to 90 mM, or 90 mM to 100 mM.

Ion pairing agents bind to the solute by ionic interactions, which results in the modification of the solute hydrophobicity. In some embodiments, the ion pairing agent is trifluoroacetic acid, pentafluoropropionic acid, heptafluorobutyric acid, ammonium acetate, phosphoric acid, tetramethylammonium chloride, tetrabutylammonium chloride, or triethylamine. In some embodiments, the ion pairing agent is UV transparent.

In some embodiments, the concentration of the ion pairing agent in the mobile phase is from 0.01% to 0.1%, 0.01% to 0.09%, 0.01% to 0.08%, 0.01% to 0.07%, 0.01% to 0.06%, 0.01% to 0.05%, 0.01% to 0.04%, 0.01% to 0.03%, 0.01% to 0.02%, 0.02% to 0.1%, 0.02% to 0.09%, 0.02% to 0.08%, 0.02% to 0.07%, 0.02% to 0.06%, 0.02% to 0.05%, 0.02% to 0.04%, 0.02% to 0.03%, 0.03% to 0.1%, 0.03% to 0.09%, 0.03% to 0.08%, 0.03% to 0.07%, 0.03% to 0.06%, 0.03% to 0.05%, 0.03% to 0.04%, 0.04% to 0.1%, 0.04% to 0.09%, 0.04% to 0.08%, 0.04% to 0.07%, 0.04% to 0.06%, 0.04% to 0.05%, 0.05% to 0.1%, 0.05% to 0.09%, 0.05% to 0.08%, 0.05% to 0.07%, or 0.05% to 0.06%, 0.06% to 0.1%, 0.06% to 0.09%, 0.06% to 0.08%, 0.06% to 0.07%, 0.07% to 0.1%, 0.07% to 0.09%, 0.07% to 0.08%, 0.08% to 0.1%, 0.08% to 0.09%, or 0.09% to 0.1%. In some embodiments, the concentration of the ion pairing agent in the mobile phase is from 10 mM to 100 mM, 10 mM to 90 mM, 10 mM to 80 mM, 10 mM to 70 mM, 10 mM to 60 mM, 10 mM to 50 mM, 10 mM to 40 mM, 10 mM to 30 mM, 10 mM to 20 mM, 20 mM to 100 mM, 20 mM to 90 mM, 20 mM to 80 mM, 20 mM to 70 mM, 20 mM to 60 mM, 20 mM to 50 mM, 20 mM to 40 mM, 20 mM to 30 mM, 30 mM to 100 mM, 30 mM to 90 mM, 30 mM to 80 mM, 30 mM to 70 mM, 30 mM to 60 mM, 30 mM to 50 mM, 30 mM to 40 mM, 40 mM to 100 mM, 40 mM to 90 mM, 40 mM to 80 mM, 40 mM to 70 mM, 40 mM to 60 mM, 40 mM to 50 mM, 50 mM to 90 mM, 50 mM to 80 mM, 50 mM to 70 mM, 50 mM to 60 mM, 60 mM to 100 mM, 60 mM to 90 mM, 60 mM to 80 mM, 60 mM to 70 mM, 70 mM to 100 mM, 70 mM to 90 mM, 70 mM to 80 mM, 80 mM to 100 mM, 80 mM to 90 mM, or 90 mM to 100 mM.

The flow rate of the mobile phase can be adjusted. In some embodiments, the flow rate of the mobile phase is 0.5 mL/min to 20 mL/min, 0.5 mL/min to 10 mL/min, 0.5 mL/min to 9 mL/min, 0.5 mL/min to 8 mL/min, 0.5 mL/min to 7 mL/min, 0.5 mL/min to 6 mL/min, 0.5 mL/min to 5 mL/min, 0.5 ml/min to 4 mL/min, 0.5 mL/min to 3 mL/min, 0.5 mL/min to 2 mL/min, 0.5 mL/min to 1 mL/min, 1 mL/min to 20 mL/min, 1 mL/min to 10 mL/min, 1 mL/min to 9 mL/min, 1 mL/min to 8 mL/min, 1 mL/min to 7 mL/min, 1 mL/min to 6 mL/min, 1 mL/min to 5 mL/min, 1 ml/min to 4 mL/min, 1 mL/min to 3 mL/min, 1 mL/min to 2 mL/min, 2 mL/min to 20 mL/min, 2 mL/min to 10 mL/min, 2 mL/min to 9 mL/min, 2 mL/min to 8 mL/min, 2 mL/min to 7 mL/min, 2 mL/min to 6 mL/min, 2 mL/min to 5 mL/min, 2 ml/min to 4 mL/min, 2 mL/min to 3 mL/min, 3 mL/min to 20 mL/min, 3 mL/min to 10 mL/min, 3 mL/min to 9 mL/min, 3 mL/min to 8 mL/min, 3 mL/min to 7 mL/min, 3 mL/min to 6 mL/min, 3 mL/min to 5 mL/min, 3 ml/min to 4 mL/min, 4 mL/min to 20 mL/min, 4 mL/min to 10 mL/min, 4 mL/min to 9 mL/min, 4 mL/min to 8 mL/min, 4 mL/min to 7 mL/min, 4 mL/min to 6 mL/min, 4 mL/min to 5 mL/min, 5 mL/min to 20 mL/min, 5 mL/min to 10 mL/min, 5 mL/min to 9 mL/min, 5 mL/min to 8 mL/min, 5 mL/min to 7 mL/min, 5 mL/min to 6 mL/min, 6 mL/min to 20 mL/min, 6 mL/min to 10 mL/min, 6 mL/min to 9 mL/min, 6 mL/min to 8 mL/min, 6 mL/min to 7 mL/min, 7 mL/min to 20 mL/min, 7 mL/min to 10 mL/min, 7 mL/min to 9 mL/min, 7 mL/min to 8 mL/min, 8 mL/min to 20 mL/min, 8 mL/min to 10 mL/min, 8 mL/min to 9 mL/min, 9 mL/min to 20 mL/min, 9 mL/min to 10 mL/min, or 10 mL/min to 20 mL/min.

Commercial scale separations can employ much higher flow rates. In some embodiments, the flow rate of the mobile phase is 0.5 L/min to 20 L/min, 0.5 L/min to 10 L/min, 0.5 L/min to 9 L/min, 0.5 L/min to 8 L/min, 0.5 L/min to 7 L/min, 0.5 L/min to 6 L/min, 0.5 L/min to 5 L/min, 0.5 L/min to 4 L/min, 0.5 L/min to 3 L/min, 0.5 L/min to 2 L/min, 0.5 L/min to 1 L/min, 1 L/min to 20 L/min, 1 L/min to 10 L/min, 1 L/min to 9 L/min, 1 L/min to 8 L/min, 1 L/min to 7 L/min, 1 L/min to 6 L/min, 1 L/min to 5 L/min, 1 L/min to 4 L/min, 1 L/min to 3 L/min, 1 L/min to 2 L/min, 2 L/min to 20 L/min, 2 L/min to 10 L/min, 2 L/min to 9 L/min, 2 L/min to 8 L/min, 2 L/min to 7 L/min, 2 L/min to 6 L/min, 2 L/min to 5 L/min, 2 L/min to 4 L/min, 2 L/min to 3 L/min, 3 L/min to 20 L/min, 3 L/min to 10 L/min, 3 L/min to 9 L/min, 3 L/min to 8 L/min, 3 L/min to 7 L/min, 3 L/min to 6 L/min, 3 L/min to 5 L/min, 3 L/min to 4 L/min, 4 L/min to 20 L/min, 4 L/min to 10 L/min, 4 L/min to 9 L/min, 4 L/min to 8 L/min, 4 L/min to 7 L/min, 4 L/min to 6 L/min, 4 L/min to 5 L/min, 5 L/min to 20 L/min, 5 L/min to 10 L/min, 5 L/min to 9 L/min, 5 L/min to 8 L/min, 5 L/min to 7 L/min, 5 L/min to 6 L/min, 6 L/min to 20 L/min, 6 L/min to 10 L/min, 6 L/min to 9 L/min, 6 L/min to 8 L/min, 6 L/min to 7 L/min, 7 L/min to 20 L/min, 7 L/min to 10 L/min, 7 L/min to 9 L/min, 7 L/min to 8 L/min, 8 L/min to 20 L/min, 8 L/min to 10 L/min, 8 L/min to 9 L/min, 9 L/min to 20 L/min, 9 L/min to 10 L/min, or 10 L/min to 20 L/min.

The pressure of the mobile phase can be adjusted. In some embodiments, the pressure of the mobile phase is less than 20,000 psi, less than 15,000 psi, less than 10,000 psi, less than 9000 psi, less than 8000 psi, less than 7000 psi, less than 6000 psi, less than 5000 psi, less than 4000 psi, less than 3000 psi, less than 2000 psi, or less than 1000 psi. In some embodiments, the pressure of the mobile phase is from 1000 psi to 20,000 psi, 1000 psi to 15,000 psi, 1000 psi to 10,000 psi, 1000 psi to 9000 psi, 1000 psi to 8000 psi, 1000 psi to 7000 psi, 1000 psi to 6000 psi, 1000 psi to 5000 psi, 1000 psi to 4000 psi, 1000 psi to 3000 psi, 1000 psi to 2000 psi, 2000 psi to 20,000 psi, 2000 psi to 15,000 psi, 2000 psi to 10,000 psi, 2000 psi to 9000 psi, 2000 psi to 8000 psi, 2000 psi to 7000 psi, 2000 psi to 6000 psi, 2000 psi to 5000 psi, 2000 psi to 4000 psi, 2000 psi to 3000 psi, 3000 psi to 20,000 psi, 3000 psi to 15,000 psi, 3000 psi to 10,000 psi, 3000 psi to 9000 psi, 3000 psi to 8000 psi, 3000 psi to 7000 psi, 3000 psi to 6000 psi, 3000 psi to 5000 psi, 3000 psi to 4000 psi, 4000 psi to 20,000 psi, 4000 psi to 15,000 psi, 4000 psi to 10,000 psi, 4000 psi to 9000 psi, 4000 psi to 8000 psi, 4000 psi to 7000 psi, 4000 psi to 6000 psi, 4000 psi to 5000 psi, 5000 psi to 20,000 psi, 5000 psi to 15,000 psi, 5000 psi to 10,000 psi, 5000 psi to 9000 psi, 5000 psi to 8000 psi, 5000 psi to 7000 psi, 5000 psi to 6000 psi, 6000 psi to 20,000 psi, 6000 psi to 15,000 psi, 6000 psi to 10,000 psi, 6000 psi to 9000 psi, 6000 psi to 8000 psi, 6000 psi to 7000 psi, 7000 psi to 20,000 psi, 7000 psi to 15,000 psi, 7000 psi to 10,000 psi, 7000 psi to 9000 psi, 7000 psi to 8000 psi, 8000 psi to 20,000 psi, 8000 psi to 15,000 psi, 8000 psi to 10,000 psi, 8000 psi to 9000 psi, 9000 psi to 20,000 psi, 9000 psi to 15,000 psi, 9000 psi to 10,000 psi, 10,000 psi to 20,000 psi, 10,000 psi to 15,000 psi, or 15,000 psi to 20,000 psi.

The temperature can affect the viscosity of the mobile phase. In some embodiments, the temperature in the mobile phase is from 30° C. to 100° C., 30° C. to 90° C., 30° C. to 80° C., 30° C. to 70° C., 30° C. to 60° C., 30° C. to 50° C., 30° C. to 40° C., 40° C. to 100° C., 40° C. to 90° C., 40° C. to 80° C., 40° C. to 70° C., 40° C. to 60° C., 40° C. to 50° C., 50° C. to 100° C., 50° C. to 90° C., 50° C. to 80° C., 50° C. to 70° C., 50° C. to 60° C., 60° C. to 100° C., 60° C. to 90° C., 60° C. to 80° C., 60° C. to 70° C., 70° C. to 100° C., 70° C. to 90° C., 70° C. to 80° C., 80° C. to 100° C., 80° C. to 90° C., or 90° C. to 100° C. In some embodiments, the temperature in the mobile phase is 30° C., 40° C., 50° C., 60° C., 70° C., 80° C., 90° C., or 100° C.

In some embodiments, the composition of the mobile phase is kept constant ("isocratic elution") during the chromatographic process.

In some embodiments the composition of the mobile phase may be varied ("gradient elution") during the chromatographic process. In gradient elution, the mobile phase may be varied from low to high eluting strength. The eluting strength of the mobile phase is reflected by analyte retention times with high eluting strength producing fast elution and short retention times.

In gradient elution, an initial mobile phase (mobile phase A) and a final mobile phase (mobile phase B) are employed. In some embodiments, the concentration of the organic solvent is lower in mobile phase A than in mobile phase B.

In some embodiments, mobile phase A comprises an organic solvent, a buffer, and an ion pairing agent. In some embodiments, mobile phase A comprises an organic solvent and a buffer. In some embodiments, mobile phase A comprises an organic solvent and an ion pairing agent. In some embodiments, mobile phase A comprises a buffer and an ion pairing agent.

In some embodiments, the concentration of organic solvent in mobile phase A is from 1% to 50%, 1% to 40%, 1% to 30%, 1% to 20%, 1% to 10%, 1% to 5%, 5% to 50%, 5% to 40%, 5% to 30%, 5% to 20%, 5% to 10%, 10% to 50%, 10% to 40%, 10% to 30%, 10% to 20%, 20% to 50%, 20% to 40%, 20% to 30%, 30% to 50%, 30% to 40%, or 40% to 50%. In some embodiments, the concentration of organic solvent in mobile phase A is 50% or less, 45% or less, 40% or less, 35% or less, 30% or less, 25% or less, 20% or less, 15% or less, 10% or less, or 5% or less. In some embodiments, there is no organic solvent in mobile phase A.

In some embodiments, mobile phase B comprises an organic solvent, a buffer, and an ion pairing agent. In some embodiments, mobile phase B comprises an organic solvent and a buffer. In some embodiments, mobile phase B comprises an organic solvent and an ion pairing agent.

In some embodiments, the concentration of organic solvent in mobile phase B is from 50% to 100%, 50% to 95%, 50% to 90%, 50% to 80%, 50% to 70%, 50% to 60%, 60% to 100%, 60% to 95%, 60% to 90%, 60% to 80%, 60% to 70%, 70% to 100%, 70% to 95%, 70% to 90%, 70% to 80%, 80% to 100%, 80% to 95%, 80% to 90%, 90% to 100%, 90% to 95%, or 95% to 100%. In some embodiments, the concentration of organic solvent in mobile phase B is 50% or more, 55% or more, 60% or more, 65% or more, 70% or more, 75% or more, 80% or more, 85% or more, 90% or more, or 95% or more.

In gradient elution, the gradient can be measured in either volume mode or time mode. In volume mode, the gradient is based on the amount (based on mL or column volumes) of mobile phase that has passed through the column. In time mode, the gradient is based on the elapsed time.

In some embodiments, the concentration of mobile phase B in the gradient increases over a predetermined period of time. In some embodiments, the concentration of mobile phase B in the gradient increases over a predetermined period of time and then remains constant for a predetermined period of time. In some embodiments, the concentration of mobile phase B in the gradient remains constant for a predetermined period of time and then increases over a predetermined period of time.

In some embodiments, the concentration of mobile phase B in the gradient for a predetermined period of time is 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the predetermined period of time for the gradient is 1 minute, 2 min, 3 min, 4 min, 5 min, 6 min, 7 min, 8 min, 9 min, 10 min, 15 min, 20 min, 30 min, 40 min, 50 min, 60 min, 70 min, 80 min, 90 min, 100 min, 200 min, 300 min, 400 min, or 500 min. In some embodiments, the predetermined period of time for the gradient is from 1 min to 500 min, 1 min to 400 min, 1 min to 300 min, 1 min to 200 min, 1 min to 100 min, 1 min to 50 min, 1 min to 25 min, 1 min to 10 min, 1 min to 5 min, 1 min to 4 min, 1 min to 3 min, 1 min to 2 min, 2 min to 500 min, 2 min to 400 min, 2 min to 300 min, 2 min to 200 min, 2 min to 100 min, 2 min to 50 min, 2 min to 25 min, 2 min to 10 min, 2 min to 5 min, 2 min to 4 min, 2 min to 3 min, 3 min to 500 min, 3 min to 400 min, 3 min to 300 min, 3 min to 200 min, 3 min to 100 min, 3 min to 50 min, 3 min to 25 min, 3 min to 10 min, 3 min to 5 min, 3 min to 4 min, 4 min to 500 min, 4 min to 400 min, 4 min to 300 min, 4 min to 200 min, 4 min to 100 min, 4 min to 50 min, 4 min to 25 min, 4 min to 10 min, 4 min to 5 min, 5 min to 500 min, 5 min to 400 min, 5 min to 300 min, 5 min to 200 min, 5 min to 100 min, 5 min to 50 min, 5 min to 25 min, 5 min to 10 min, 10 min to 500 min, 10 min to 400 min, 10 min to 300 min, 10 min to 200 min, 10 min to 100 min, 10 min to 50 min, 10 min to 25 min, 25 min to 500 min, 25 min to 400 min, 25 min to 300 min, 25 min to 200 min, 25 min to 100 min, 25 min to 50 min, 50 min to 500 min, 50 min to 400 min, 50 min to 300 min, 50 min to 200 min, 50 min to 100 min, 100 min to 500 min, 100 min to 400 min, 100 min to 300 min, 100 min to 200 min, 200 min to 500 min, 200 min to 400 min, 200 min to 300 min, 300 min to 500 min, 300 min to 400 min, or 400 min to 500 min.

In some embodiments, the gradient is a linear gradient. In some embodiments, the concentration of mobile phase B in the gradient increases at a steady rate over time with the remaining concentration in the gradient composed of mobile phase A. In some embodiments, the concentration of mobile phase B increases by 0.1% per minute, 0.2% per minute, 0.3% per minute, 0.4% per minute, 0.5% per minute, 0.6% per minute, 0.7% per minute, 0.8% per minute, 0.9% per minute, 1% per minute, 1.1% per minute, 1.2% per minute, 1.3% per minute, 1.4% per minute, 1.5% per minute, 1.6% per minute, 1.7% per minute, 1.8% per minute, 1.9% per minute, 2% per minute, 3% per minute, 4% per minute, 5% per minute, 6% per minute, 7% per minute, 8% per minute, 9% per minute, or 10% per minute.

In some embodiments, the gradient is a step gradient (a series of isocratic elutions at different % B).

The "total cycle time" is the time measured from when the sample is loaded onto the column to when the mobile phase is discontinued. In some embodiments, the total cycle time is 10 min or more, 25 min or more, 50 min or more, 100 min or more, 200 min or more, 300 min or more, 400 min or more, 500 min or more, 600 min or more, 700 min or more, 800 min or more, 900 min or more, or 1000 min or more. In some embodiments, the total cycle time is 10 min to 500 min, 10 min to 400 min, 10 min to 300 min, 10 min to 200 min, 10 min to 100 min, 10 min to 50 min, 10 min to 25 min, 25 min to 500 min, 25 min to 400 min, 25 min to 300 min, 25 min to 200 min, 25 min to 100 min, 25 min to 50 min, 50 min to 500 min, 50 min to 400 min, 50 min to 300 min, 50 min to 200 min, 50 min to 100 min, 100 min to 500 min, 100 min to 400 min, 100 min to 300 min, 100 min to 200 min, 200 min to 500 min, 200 min to 400 min, 200 min to 300 min, 300 min to 500 min, 300 min to 400 min, or 400 min to 500 min.

In some embodiments, the alkylated cyclodextrin composition to be fractionated is dissolved in the initial mobile phase before it is loaded onto the stationary phase. In some embodiments, formic acid, acetic acid, or salt is added to the initial mobile phase to increase the solubility of the alkylated cyclodextrin composition to be fractionated before it is loaded onto the stationary phase.

The final yield of the fractionated alkylated cyclodextrin obtained at completion of the process will vary. The final yield of fractionated alkylated cyclodextrin composition based on the loaded unfractionated alkylated cyclodextrin composition can range from 10% to 95%, 10% to 90%, 10% to 80%, 10% to 70%, 10% to 60%, 10% to 50%, 10% to 40%, 10% to 30%, 10% to 20%, 20% to 95%, 20% to 90%, 20% to 80%, 20% to 70%, 20% to 60%, 20% to 50%, 20% to 40%, 20% to 30%, 30% to 95%, 30% to 90%, 30% to 80%, 30% to 70%, 30% to 60%, 30% to 50%, 30% to 40%, 40% to 95%, 40% to 90%, 40% to 80%, 40% to 70%, 40% to 60%, 40% to 50%, 50% to 95%, 50% to 90%, 50% to 80%, 50% to 70%, 50% to 60%, 60% to 95%, 60% to 90%, 60% to 80%, 60% to 70%, 70% to 95%, 70% to 90%, 70% to 80%, 80% to 95%, 80% to 90%, or 90% to 95%. In some embodiments, the final yield of fractionated alkylated cyclodextrin composition based on the loaded unfractionated alkylated cyclodextrin composition is 10% or more, 20% or more, 30% or more, 40% or more, 50% or more, 60% or more, 70% or more, 80% or more, 90% or more, or 95% or more.

In some embodiments, the phosphate level in the fractionated alkylated cyclodextrin composition is less than 5000 ppm, less than 1250 ppm, less than 1000 ppm, less than 200 ppm, less than 150 ppm, less than 125 ppm, less than 100 ppm, less than 95 ppm, less than 90 ppm, less than 85 ppm, less than 80 ppm, less than 75 ppm, less than 70 ppm, less than 65 ppm, less than 60 ppm, less than 55 ppm, less than 50 ppm, less than 45 ppm, less than 40 ppm, less than 35 ppm, less than 30 ppm, less than 25 ppm, less than 20 ppm, less than 15 ppm, less than 10 ppm, less than 5 ppm, less than 1 ppm, or less than 0.1 ppm. In some embodiments, the phosphate level in the fractionated alkylated cyclodextrin composition is 5000 ppm to 0.1 ppm, 5000 ppm to 1 ppm, 5000 ppm to 5 ppm, 5000 ppm to 10 ppm, 5000 ppm to 50 ppm, 5000 ppm to 100 ppm, 5000 ppm to 200 ppm, 5000 ppm to 1000 ppm, 5000 ppm to 1250 ppm, 1250 ppm to 0.1 ppm, 1250 ppm to 1 ppm, 1250 ppm to 5 ppm, 1250 ppm to 10 ppm, 1250 ppm to 50 ppm, 1250 ppm to 100 ppm, 1250 ppm to 200 ppm, 1250 ppm to 1000 ppm, 1000 ppm to 0.1 ppm, 1000 ppm to 1 ppm, 1000 ppm to 5 ppm, 1000 ppm to 10 ppm, 1000 ppm to 50 ppm, 1000 ppm to 100 ppm, 1000 ppm to 200 ppm, 200 ppm to 0.1 ppm, 200 ppm to 1 ppm, 200 ppm to 5 ppm, 200 ppm to 10 ppm, 200 ppm to 50 ppm, 200 ppm to 100 ppm, 100 ppm to 0.1 ppm, 100 ppm to 1 ppm, 100 ppm to 5 ppm, 100 ppm to 10 ppm, 100 ppm to 50 ppm, 50 ppm to 0.1 ppm, 50 ppm to 1 ppm, 50 ppm to 5 ppm, 50 ppm to 10 ppm, 10 ppm to 0.1 ppm, 10 ppm to 1 ppm, 10 ppm to 5 ppm, 5 ppm to 0.1 ppm, 5 ppm to 1 ppm, or 1 ppm to 0.1 ppm.

In some embodiments, the fractionated alkylated cyclodextrin compositions are substantially free of one or more UV-active impurities, which may have drug degrading properties. The presence of one or more UV-active impurities can be determined, inter alia, by UV/visible ("UV/vis") spectrophotometry. The UV-active impurities can include one or more low-molecular weight species (e.g., a species having a molecular weight less than 1,000 Da), such as, but not limited to a species generated as a side-product and/or decomposition product in the reaction mixture. As such, UV-active impurities include, but are not limited to, a glycosidic moiety, a ring-opened cyclodextrin species, a reducing sugar, a glucose degradation product (e.g., 3,4-dideoxyglucosone-3-ene, carbonyl-containing degradants such as 2-furaldehyde, 5-hydroxymethyl-2-furaldehyde, and the like), and combinations thereof.

The presence of UV-active impurities in the fractionated alkylated cyclodextrin composition can be measured by UV/vis in absorbance units (A.U.). In some embodiments, the fractionated alkylated cyclodextrin composition has an absorption of less than 1 A.U., less than 0.9 A.U., less than 0.8 A.U., less than 0.7 A.U., less than 0.6 A.U., 0.5 A.U., less than 0.4 A.U., less than 0.3 A.U., less than 0.2 A.U., or less than 0.1 A.U. [01%] The absorbance of the solution becomes linear with the concentration according to the formula:

$$A = \varepsilon l c$$

wherein
A=absorbance
$\varepsilon$=extinction coefficient
l=path length
c=molar concentration.

The presence of UV-active impurities in the fractionated alkylated cyclodextrin composition can be measured using UV/vis spectrophotometry at a wavelength of 245 to 270 nm using a cell having a path length of 1 cm. In some embodiments, the fractionated alkylated cyclodextrin composition has an absorption of less than 1 A.U. at a wavelength of 245 nm to 270 nm for an aqueous solution containing 200 mg of the fractionated alkylated cyclodextrin composition per mL of solution, less than 1 A.U. at a wavelength of 245 nm to 270 nm for an aqueous solution containing 300 mg of the fractionated alkylated cyclodextrin composition per mL of solution, less than 1 A.U. at a wavelength of 245 nm to 270 nm for an aqueous solution containing 400 mg of the fractionated alkylated cyclodextrin composition per mL of solution, less than 1 A.U. at a wavelength of 245 nm to 270 nm for an aqueous solution containing 500 mg of the fractionated alkylated cyclodextrin composition per mL of solution, 0.9 A.U. or less at a wavelength of 245 nm to 270 nm for an aqueous solution containing 200 mg of the fractionated alkylated cyclodextrin composition per mL of solution, 0.9 A.U. or less at a wavelength of 245 nm to 270 nm for an aqueous solution containing 300 mg of the fractionated alkylated cyclodextrin composition per mL of solution, 0.9 A.U. or less at a wavelength of 245 nm to 270 nm for an aqueous solution containing 400 mg of the fractionated alkylated cyclodextrin composition per mL of solution, 0.9 A.U. or less at a wavelength of 245 nm to 270 nm for an aqueous solution containing 500 mg of the fractionated alkylated cyclodextrin composition per mL of solution, 0.8 A.U. or less at a wavelength of 245 nm to 270 nm for an aqueous solution containing 200 mg of the fractionated alkylated cyclodextrin composition per mL of solution, 0.8 A.U. or less at a wavelength of 245 nm to 270 nm for an aqueous solution containing 300 mg of the fractionated alkylated cyclodextrin composition per mL of solution, 0.8 A.U. or less at a wavelength of 245 nm to 270 nm for an aqueous solution containing 400 mg of the fractionated alkylated cyclodextrin composition per mL of solution, 0.8 A.U. or less at a wavelength of 245 nm to 270 nm for an aqueous solution containing 500 mg of the fractionated alkylated cyclodextrin composition per mL of solution, 0.7 A.U. or less at a wavelength of 245 nm to 270 nm for an aqueous solution containing 200 mg of the fractionated alkylated cyclodextrin composition per mL of solution, 0.7 A.U. or less at a wavelength of 245 nm to 270 nm for an aqueous solution containing 300 mg of the fractionated alkylated cyclodextrin composition per mL of solution, 0.7 A.U. or less at a wavelength of 245 nm to 270 nm for an aqueous solution containing 400 mg of the fractionated alkylated cyclodextrin composition per mL of solution, 0.7 A.U. or less at a wavelength of 245 nm to 270 nm for an aqueous solution containing 500 mg of the fractionated alkylated cyclodextrin composition per mL of solution, 0.6 A.U. or less at a wavelength of 245 nm to 270 nm for an aqueous solution containing 200 mg of the fractionated alkylated cyclodextrin composition per mL of solution, 0.6 A.U. or less at a wavelength of 245 nm to 270 nm for an aqueous solution containing 300 mg of the fractionated alkylated cyclodextrin composition per mL of solution, 0.6 A.U. or less at a wavelength of 245 nm to 270 nm for an aqueous solution containing 400 mg of the fractionated alkylated cyclodextrin composition per mL of solution, 0.6 A.U. or less at a wavelength of 245 nm to 270 nm for an aqueous solution containing 500 mg of the fractionated alkylated cyclodextrin composition per mL of solution, 0.5 A.U. or less at a wavelength of 245 nm to 270 nm for an aqueous solution containing 200 mg of the fractionated alkylated cyclodextrin composition per mL of solution, 0.5 A.U. or less at a wavelength of 245 nm to 270 nm for an aqueous solution containing 300 mg of the fractionated alkylated cyclodextrin composition per mL of solution, 0.5 A.U. or less at a wavelength of 245 nm to 270 nm for an aqueous solution containing 400 mg of the fractionated alkylated cyclodextrin composition per mL of solution, 0.5 A.U. or less at a wavelength of 245 nm to 270 nm for an aqueous solution containing 500 mg of the fractionated alkylated cyclodextrin composition per mL of solution, 0.4 A.U. or less at a wavelength of 245 nm to 270 nm for an aqueous solution containing 200 mg of the fractionated alkylated cyclodextrin composition per mL of solution, 0.4 A.U. or less at a wavelength of 245 nm to 270 nm for an aqueous solution containing 300 mg of the fractionated alkylated cyclodextrin composition per mL of solution, 0.4 A.U. or less at a wavelength of 245 nm to 270 nm for an aqueous solution containing 400 mg of the fractionated alkylated cyclodextrin composition per mL of solution, 0.4 or less A.U. at a wavelength of 245 nm to 270 nm for an aqueous solution containing 500 mg of the fractionated alkylated cyclodextrin composition per mL of solution, 0.3 A.U. or less at a wavelength of 245 nm to 270 nm for an aqueous solution containing 200 mg of the fractionated alkylated cyclodextrin composition per mL of solution, 0.3 A.U. or less at a wavelength of 245 nm to 270 nm for an aqueous solution containing 300 mg of the fractionated alkylated cyclodextrin composition per mL of solution, 0.3 A.U. or less at a wavelength of 245 nm to 270 nm for an aqueous solution containing 400 mg of the fractionated alkylated cyclodextrin composition per mL of solution, 0.3 A.U. or less at a wavelength of 245 nm to 270 nm for an aqueous solution containing 500 mg of the fractionated alkylated cyclodextrin composition per mL of solution, 0.2 A.U. or less at a wavelength of 245 nm to 270 nm for an aqueous solution containing 200 mg of the fractionated alkylated cyclodextrin composition per mL of solution, 0.2 A.U. or less at a wavelength of 245 nm to 270 nm for an aqueous solution containing 300 mg of the fractionated alkylated cyclodextrin composition per mL of solution, 0.2 A.U. or less at a wavelength of 245 nm to 270 nm for an aqueous solution containing 400 mg of the fractionated alkylated cyclodextrin composition per mL of solution, or 0.2 A.U. or less at a wavelength of 245 nm to 270 nm for an aqueous solution containing 500 mg of the fractionated alkylated cyclodextrin composition per mL of solution.

The presence of a color-forming agent in the fractionated alkylated cyclodextrin composition can be measured using UV/vis spectrophotometry at a wavelength of 320 nm to 350 nm using a cell having a path length of 1 cm. In some embodiments, the fractionated alkylated cyclodextrin composition has an absorption of less than 1 A.U. at a wavelength of 320 nm to 350 nm for an aqueous solution containing 200 mg of the fractionated alkylated cyclodextrin composition per mL of solution, less than 1 A.U. at a wavelength of 320 nm to 350 nm for an aqueous solution containing 300 mg of the fractionated alkylated cyclodextrin composition per mL of solution, less than 1 A.U. at a wavelength of 320 nm to 350 nm for an aqueous solution containing 400 mg of the fractionated alkylated cyclodextrin composition per mL of solution, less than 1 A.U. at a wavelength of 320 nm to 350 nm for an aqueous solution containing 500 mg of the fractionated alkylated cyclodextrin composition per mL of solution, 0.9 A.U. or less at a wavelength of 320 nm to 350 nm for an aqueous solution containing 200 mg of the fractionated alkylated cyclodextrin composition per mL of solution, 0.9 A.U. or less at a wavelength of 320 nm to 350 nm for an aqueous solution containing 300 mg of the fractionated alkylated cyclodextrin composition per mL of solution, 0.9 A.U. or less at a wavelength of 320 nm to 350 nm for an aqueous solution containing 400 mg of the fractionated alkylated cyclodextrin composition per mL of solution, 0.9 A.U. or less at a wavelength of 320 nm to 350 nm for an aqueous solution containing 500 mg of the fractionated alkylated cyclodextrin composition per mL of solution, 0.8 A.U. or less at a wavelength of 320 nm to 350 nm for an aqueous solution containing 200 mg of the fractionated alkylated cyclodextrin composition per mL of solution, 0.8 A.U. or less at a wavelength of 320 nm to 350 nm for an aqueous solution containing 300 mg of the fractionated alkylated cyclodextrin composition per mL of solution, 0.8 A.U. or less at a wavelength of 320 nm to 350 nm for an aqueous solution containing 400 mg of the fractionated alkylated cyclodextrin composition per mL of solution, 0.8 A.U. or less at a wavelength of 320 nm to 350 nm for an aqueous solution containing 500 mg of the fractionated alkylated cyclodextrin composition per mL of solution, 0.7 A.U. or less at a wavelength of 320 nm to 350 nm for an aqueous solution containing 200 mg of the fractionated alkylated cyclodextrin composition per mL of solution, 0.7 A.U. or less at a wavelength of 320 nm to 350 nm for an aqueous solution containing 300 mg of the fractionated alkylated cyclodextrin composition per mL of solution, 0.7 A.U. or less at a wavelength of 320 nm to 350 nm for an aqueous solution containing 400 mg of the fractionated alkylated cyclodextrin composition per mL of solution, 0.7 A.U. or less at a wavelength of 320 nm to 350 nm for an aqueous solution containing 500 mg of the fractionated alkylated cyclodextrin composition per mL of solution, 0.6 A.U. or less at a wavelength of 320 nm to 350 nm for an aqueous solution containing 200 mg of the fractionated alkylated cyclodextrin composition per mL of solution, 0.6 A.U. or less at a wavelength of 320 nm to 350 nm for an aqueous solution containing 300 mg of the fractionated alkylated cyclodextrin composition per mL of solution, 0.6 A.U. or less at a wavelength of 320 nm to 350 nm for an aqueous solution containing 400 mg of the fractionated alkylated cyclodextrin composition per mL of solution, 0.6 A.U. or less at a wavelength of 320 nm to 350 nm for an aqueous solution containing 500 mg of the fractionated alkylated cyclodextrin composition per mL of solution, 0.5 A.U. or less at a wavelength of 320 nm to 350 nm for an aqueous solution containing 200 mg of the fractionated alkylated cyclodextrin composition per mL of solution, 0.5 A.U. or less at a wavelength of 320 nm to 350 nm for an aqueous solution containing 300 mg of the fractionated alkylated cyclodextrin composition per mL of solution, 0.5 A.U. or less at a wavelength of 320 nm to 350 nm for an aqueous solution containing 400 mg of the fractionated alkylated cyclodextrin composition per mL of solution, 0.5 A.U. or less at a wavelength of 320 nm to 350 nm for an aqueous solution containing 500 mg of the fractionated alkylated cyclodextrin composition per mL of solution, 0.4 A.U. or less at a wavelength of 320 nm to 350 nm for an aqueous solution containing 200 mg of the fractionated alkylated cyclodextrin composition per mL of solution, 0.4 A.U. or less at a wavelength of 320 nm to 350 nm for an aqueous solution containing 300 mg of the fractionated alkylated cyclodextrin composition per mL of solution, 0.4 A.U. or less at a wavelength of 320 nm to 350 nm for an aqueous solution containing 400 mg of the fractionated alkylated cyclodextrin composition per mL of solution, 0.4 A.U. or less at a wavelength of 320 nm to 350 nm for an aqueous solution containing 500 mg of the fractionated alkylated cyclodextrin composition per mL of solution, 0.3 A.U. or less at a wavelength of 320 nm to 350 nm for an aqueous solution containing 200 mg of the fractionated alkylated cyclodextrin composition per mL of solution, 0.3 A.U. or less at a wavelength of 320 nm to 350 nm for an aqueous solution containing 300 mg of the fractionated alkylated cyclodextrin composition per mL of solution, 0.3 A.U. or less at a wavelength of 320 nm to 350 nm for an aqueous solution containing 400 mg of the fractionated alkylated cyclodextrin composition per mL of solution, 0.3 A.U. or less at a wavelength of 320 nm to 350 nm for an aqueous solution containing 500 mg of the fractionated alkylated cyclodextrin composition per mL of solution, 0.2 A.U. or less at a wavelength of 320 nm to 350 nm for an aqueous solution containing 200 mg of the fractionated alkylated cyclodextrin composition per mL of solution, 0.2 A.U. or less at a wavelength of 320 nm to 350 nm for an aqueous solution containing 300 mg of the fractionated alkylated cyclodextrin composition per mL of solution, 0.2 A.U. or less at a wavelength of 320 nm to 350 nm for an aqueous solution containing 400 mg of the fractionated alkylated cyclodextrin composition per mL of solution, or 0.2 A.U. or less at a wavelength of 320 nm to 350 nm for an aqueous solution containing 500 mg of the fractionated alkylated cyclodextrin composition per mL of solution.

Methods of reducing the level of UV-active impurities and/or color forming agents may be found in WO 2009/134347 which is incorporated herein by reference in its entirety.

In some embodiments, the fractionated alkylated cyclodextrin composition comprises less than 1% wt., less than 0.5% wt., less than 0.2% wt., less than 0.1% wt., less than 0.08% wt., or less than 0.05% wt. of an alkali metal halide salt.

In some embodiments, the fractionated alkylated cyclodextrin composition comprises less than 1% wt., less than 0.5% wt., less than 0.25% wt., less than 0.1% wt., less than 0.08% wt., or less than 0.05% wt. of a hydrolyzed alkylating agent.

In some embodiments, the fractionated alkylated cyclodextrin composition comprises less than 500 ppm, less than 100 ppm, less than 50 ppm, less than 20 ppm, less than 10 ppm, less than 5 ppm, less than 2 ppm, less than 1 ppm, less than 500 ppb, or less than 250 ppb of an alkylating agent.

In some embodiments, the fractionated alkylated cyclodextrin composition comprises less than 0.5% wt., less than 0.2% wt., less than 0.1% wt., or less than 0.08% wt. of underivatized cyclodextrin.

In some embodiments, the chloride level as measured by weight ratio (w/w) in the fractionated alkylated cyclodextrin composition is 1% or less, 0.9% or less, 0.8% or less, 0.7% or less, 0.6% or less, 0.5% or less, 0.4% or less, 0.3% or less, 0.2% or less, 0.1% or less, 0.09% or less, 0.08% or less, 0.07% or less, 0.06% or less, 0.05% or less, 0.04% or less, 0.03% or less, 0.02% or less, or 0.01% or less. In some embodiments, the chloride level in the fractionated alkylated cyclodextrin composition is 1% to 0.01%, 0.9% to 0.01%, 0.8% to 0.01%, 0.7% to 0.01%, 0.6% to 0.01%, 0.5% to 0.01%, 0.4% to 0.01%, 0.3% to 0.01%, 0.2% to 0.01%, 0.1% to 0.01%, 0.09% to 0.01%, 0.08% to 0.01%, 0.07% to 0.01%, 0.06% to 0.01%, 0.05% to 0.01%, 0.04% to 0.01%, or 0.03% to 0.01%. Methods of lowering the chloride level in a cyclodextrin composition are described in WO 2013/130666 and WO 2014/066274, which are incorporated herein by reference in their entirety.

Methods of Detecting the Fractionated Alkylated Cyclodextrin Compositions

In some embodiments, the fractionated alkylated cyclodextrin can be detected using UV/Vis. In some embodiments, the fractionated alkylated cyclodextrin can be detected using refractive index detection. In some embodiments, the fractionated alkylated cyclodextrin can be detected using evaporative light scattering detection. In some embodiments, the fractionated alkylated cyclodextrin can be detected using capillary electrophoresis. In some embodiments, the fractionated alkylated cyclodextrin can be detected using a charged aerosol detector.

Methods of Evaluating the Fractionated Alkylated Cyclodextrin Compositions

The content of the fractionated alkylated cyclodextrin composition can be analyzed using capillary electrophoresis, a charged aerosol detector, mass spectrometry, and elemental analysis. In some embodiments, the content of a fractionated alkylated cyclodextrin composition can be determined using capillary electrophoresis. In some embodiments, the content of a fractionated alkylated cyclodextrin composition can be determined using a charged aerosol detector.

Uses of Fractionated Alkylated Cyclodextrin Compositions

By "complexed" is meant "being part of a clathrate or inclusion complex with," i.e., a "complexed" therapeutic agent is part of a clathrate or inclusion complex with a fractionated alkylated cyclodextrin. The term "major portion" refers to 50% or greater, by weight, on a molar basis. Thus, a formulation as described herein can contain an active agent of which more than about 50% by weight is complexed with a fractionated alkylated cyclodextrin. The actual percentage of active agent that is complexed will vary according to the complexation equilibrium binding constant characterizing the complexation of a specific fractionated alkylated cyclodextrin with a specific active agent. Also included are embodiments wherein the active agent is not complexed with the cyclodextrin or in which only a minor portion of the active agent is complexed with the fractionated alkylated cyclodextrin. It should be noted that a fractionated alkylated cyclodextrin can form one or more ionic bonds with a positively charged compound. This ionic association can occur regardless of whether the positively charged compound is complexed with the cyclodextrin by inclusion complexation.

Among other uses, a fractionated alkylated cyclodextrin composition can be used to solubilize and/or stabilize a variety of different materials and to prepare formulations for particular applications. The present fractionated alkylated cyclodextrin composition can provide enhanced solubility and/or enhanced chemical, thermochemical, hydrolytic, and/or photochemical stability of other ingredients in a composition. For example, a fractionated alkylated cyclodextrin composition can be used to stabilize an active agent in an aqueous medium. A fractionated alkylated cyclodextrin composition can also be used to increase the solubility of an active agent in an aqueous medium.

The fractionated alkylated cyclodextrin composition can include one or more active agents. The one or more active agents included in the composition can possess a wide range of water solubility, bioavailability, and hydrophilicity. Particularly suitable active agents include water insoluble, poorly water soluble, slightly water soluble, moderately water soluble, water soluble, very water soluble, hydrophobic, and/or hydrophilic therapeutic agents. It will be understood by a person of ordinary skill in the art that the one or more active agents present in a composition described herein is independently selected at each occurrence from any known active agent and from those disclosed herein. It is not necessary that the one or more active agents form a complex with the fractionated alkylated cyclodextrin, or form an ionic association with the fractionated alkylated cyclodextrin.

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents, pharmaceutically effective active agents, and other such compounds for pharmaceutical, veterinary, horticultural, household, food, culinary, agricultural, cosmetic, industrial, cleaning, confectionery, and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Representative pharmaceutically effective active agents include nutrients and nutritional agents, hematological agents, endocrine and metabolic agents, cardiovascular agents, renal and genitourinary agents, respiratory agents, central nervous system agents, gastrointestinal agents, antifungal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes, and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders, and hemin. Exemplary endocrine and metabolic agents include sex hormones, uterine-active agents, bisphosphonates, antidiabetic agents, glucose elevating agents, corticosteroids, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes. Antifungal agents suitable for use with the fractionated alkylated cyclodextrin composition described herein include, but are not limited to, posaconazole, voriconazole, clotrimazole, ketoconazole, oxiconazole, sertaconazole, tetconazole, fluconazole, itraconazole, and miconazole. Antipsychotic agents suitable for use with the fractionated alkylated cyclodextrin composition described herein include, but are not limited to, clozapine, prochlorperazine, haloperidol, thioridazine, thiothixene, risperidone, trifluoperazine hydrochloride, chlorpromazine, aripiprazole, loxapine, loxitane, olanzapine, quetiapine fumarate, risperidone, and ziprasidone.

Exemplary cardiovascular agents include nootropic agents, antiarrhythmic agents, calcium channel blocking agents, vasodilators, antiadrenergics/sympatholytics, renin angiotensin system antagonists, antihypertensive agent combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid, genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, respiratory inhalant products, nasal decongestants, respiratory enzymes, lung surfactants, antihistamines, nonnarcotic antitussives, and expectorants. Exemplary central nervous system agents include CNS stimulants, narcotic agonist analgesics, narcotic agonist-antagonist analgesics, central analgesics, acetaminophen, salicylates, nonnarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, injectable local anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including *H pylori* agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, cephalosporins and related antibiotics, carbapenem, monobactams, chloramphenicol, quinolones, fluoroquinolones, tetracyclines, macrolides, spectinomycin, streptogramins, vancomycin, oxalodinones, lincosamides, oral and parenteral aminoglycosides, colistimethate sodium, polymyxin b sulfate, bacitracin, metronidazole, sulfonamides, nitrofurans, methenamines, folate antagonists, antifungal agents, antimalarial preparations, antituberculosis agents, amebicides, antiviral agents, antiretroviral agents, leprostatics, antiprotozoals, anthelmintics, and cdc anti-infective agents. Exemplary biologic and immunological agents including immune globulins, monoclonal antibody agents, antivenins, agents for active immunization, allergenic extracts, immunologic agents, and antirheumatic agents. Exemplary dermatological agents include topical antihistamine preparations, topical anti-infectives, anti-inflammatory agents, anti-psoriatic agents, antiseborrheic products, arnica, astringents, cleansers, capsaicin, destructive agents, drying agents, enzyme preparations, topical immunomodulators, keratolytic agents, liver derivative complex, topical local anesthetics, minoxidil, eflornithine hydrochloride, photochemotherapy agents, pigment agents, topical poison ivy products, topical pyrimidine antagonist, pyrithione zinc, retinoids, rexinoids, scabicides/pediculicides, wound healing agents, emollients, protectants, sunscreens, ointment and lotion bases, rubs and liniments, dressings and granules, and physiological irrigating solutions. Exemplary ophthalmic agents include agents for glaucoma, mast cell stabilizers, ophthalmic antiseptics, ophthalmic phototherapy agents, ocular lubricants, artificial tears, ophthalmic hyperosmolar preparations, and contact lens products. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Exemplary active agents also include compounds that are sensitive to chloride levels. Exemplary chloride sensitive active agents include proteasome inhibitors such as bortezomib, disulfiram, epigallocatchin-3-gallate, salinosporamide A, and carfilzomib.

Exemplary active agents also include melphalan, topiramate, clopidogrel, ziprazadone, vestipitant, and pazopanib.

The above-listed active agents should not be considered exhaustive and is merely exemplary of the many embodiments considered within the scope of the present disclosure. Many other active agents can be administered with the formulation described herein.

A formulation described herein can be used to deliver two or more different active agents. Particular combinations of active agents can be provided in a formulation described herein. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; and 4) a first drug having a first type of biological activity and a different second drug having a different second type of biological activity. Exemplary combinations of active agents are described herein.

An active agent contained within a formulation described herein can be present as its pharmaceutically acceptable salt. As used herein, "pharmaceutically acceptable salt" refers to derivatives of the disclosed compounds wherein the active agent is modified by reacting it with an acid and/or base as needed to form an ionically bound pair. Examples of pharmaceutically acceptable salts include conventional non-toxic salts or the quaternary ammonium salts of a compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Suitable pharmaceutically acceptable salts can be prepared using an active agent that includes a basic or acidic group by conventional chemical methods. Suitable addition salts are found in *Remington's Pharmaceutical Sciences* (17th ed., Mack Publishing Co., Easton, Pa., 1985), the relevant disclosure of which is hereby incorporated by reference in its entirety.

Also provided is a combination composition comprising a mixture of at least two different fractionated alkylated cyclodextrin compositions, the mixture comprising:
  (a) a first fractionated alkylated cyclodextrin having a single degree of substitution;
  (b) a second fractionated alkylated cyclodextrin having a single degree of substitution,
  wherein the first fractionated alkylated cyclodextrin composition and second fractionated alkylated cyclodextrin composition are different and the combination of the first and second fractionated alkylated cyclodextrin is 60% by weight or more of all alkylated cyclodextrin in the composition.

In some embodiments, substituents of the first fractionated alkylated cyclodextrin and substituents of the second fractionated alkylated cyclodextrin are the same. In some embodiments, substituents of the first fractionated alkylated cyclodextrin and substituents of the second fractionated alkylated cyclodextrin are different. In some embodiments, substituents on the first fractionated alkylated cyclodextrin are a sulfoalkyl ether group, an ether group, an alkyl ether group, an alkenyl group, a hydroxyalkyl ether group, a hydroxyalkenyl ether group, a thioalkyl ether group, an aminoalkyl ether group a mercapto group, an amino group, an alkylamino group, a carboxyl group, an ester group, a nitro group, a halo group, an aldehyde group, or a 2,3-epoxypropyl group; and substituents on the second fractionated alkylated cyclodextrin are a sulfoalkyl ether group, an ether group, an alkyl ether group, an alkenyl group, a hydroxyalkyl ether group, a hydroxyalkenyl ether group, a thioalkyl ether group, an aminoalkyl ether group, a mercapto group, an amino group, an alkylamino group, a carboxyl group, an ester group, a nitro group, a halo group, an aldehyde group, or a 2,3-epoxypropyl group.

In some embodiments, the single degree of substitution of the first fractionated alkylated cyclodextrin and the single degree of substitution of the second fractionated alkylated cyclodextrin differ by 1, 2, 3, 4, 5, 6, 7, 8, 9, 10, or 11. In some embodiments, the single degree of substitution of the first fractionated alkylated cyclodextrin and the single degree of substitution of the second fractionated alkylated cyclodextrin are the same and the substituents on the first fractionated alkylated cyclodextrin and second fractionated alkylated cyclodextrin are different.

In some embodiments, the first fractionated alkylated cyclodextrin can be present in less than stoichiometric, stoichiometric, or greater than stoichiometric amounts with respect to the amount of second fractionated alkylated cyclodextrin present in the combination composition. In some embodiments, the combination composition comprises at least 5%, at least 10%, at least 20%, at least 30%, at least 40%, at least 50%, at least 60%, at least 70%, at least 80%, or at least 90% by weight of the first fractionated alkylated cyclodextrin composition. In some embodiments, the combination composition comprises at least 5%, at least 10%, at least 20%, at least 30%, at least 40%, at least 50%, at least 60%, at least 70%, at least 80%, or at least 90% by weight of the second fractionated alkylated cyclodextrin composition. The percentages can be based on a mole ratio or a weight ratio.

A method for solubilizing an active agent is also provided, the method comprising:
(a) providing a fractionated alkylated cyclodextrin composition comprising a fractionated alkylated cyclodextrin; and
(b) combining the fractionated alkylated cyclodextrin composition with an active agent.

The method of solubilizing an active agent can be performed wherein the composition comprising one or more active agents and a fractionated alkylated cyclodextrin composition is present as a dry solution, a wet solution, an inhalable composition, a parenteral composition, a solid solution, a solid mixture, a granulate, a gel, and other active agent compositions known to persons of ordinary skill in the art.

In some embodiments, the method of solubilizing an active agent provides an active agent assay of 98% or more, 98.5% or more, 99% or more, or 99.5% or more of the active agent after the composition comprising one or more active agents and a fractionated alkylated cyclodextrin composition comprising a fractionated alkylated cyclodextrin is maintained at a temperature of 80° C. for a period of 120 minutes.

Generally, the fractionated alkylated cyclodextrin composition is present in an amount sufficient to solubilize the active agent. In some embodiments, the molar ratio of fractionated alkylated cyclodextrin composition:active agent is 0.1:1 to 10:1, 0.1:1 to 5:1, 0.1 to 1:1, 0.1:1 to 0.8:1, 0.1:1 to 0.5:1, 0.5:1 to 10:1, 0.5:1 to 5:1, 0.5 to 1:1, 0.5:1 to 0.8:1, 1:1 to 10:1, 1:1 to 5:1, or 5:1 to 10:1.

In some embodiments, the solubility of the active agent with the fractionated alkylated cyclodextrin composition is increased (wt/wt on a mole basis) by 2-fold or more, 5-fold or more, 10-fold or more, 15-fold or more, 20-fold or more, 25-fold or more, 30-fold or more, 35-fold or more, 40-fold or more, 45-fold or more, or 50-fold or more compared to the solubility of the active agent without the fractionated alkylated cyclodextrin composition.

Also provided is a method of comparatively analyzing the solubilizing ability of a fractionated alkylated cyclodextrin composition and an unfractionated alkylated cyclodextrin composition comprising:
(a) combining an unfractionated alkylated cyclodextrin composition with an active agent;
(b) combining a fractionated alkylated cyclodextrin composition with an active agent, wherein the active agent is the same as in (a);
(c) comparing the solubility of the active agent in (a) to the solubility of the active agent in (b).

In some embodiments, the solubility of the active agent with a fractionated alkylated cyclodextrin composition is increased (wt/wt on a mole basis) by 2-fold or more, 5-fold or more, 10-fold or more, 15-fold or more, 20-fold or more, 25-fold or more, 30-fold or more, 35-fold or more, 40-fold or more, 45-fold or more, or 50-fold or more compared to the solubility of the active agent with an unfractionated alkylated cyclodextrin composition.

Also provided is a method of comparatively analyzing the solubilizing ability of two fractionated alkylated cyclodextrin compositions comprising:
(a) combining a first fractionated alkylated cyclodextrin composition with an active agent;
(b) combining a second fractionated alkylated cyclodextrin composition with an active agent, wherein the first and second fractionated alkylated cyclodextrin compositions are different, and wherein the active agent is the same as in (a);
(c) comparing the solubility of the active agent in (a) to the solubility of the active agent in (b).

In some embodiments, the solubility of the active agent with the first fractionated alkylated cyclodextrin composition is increased (wt/wt on a mole basis) by 2-fold or more, 5-fold or more, 10-fold or more, 15-fold or more, 20-fold or more, 25-fold or more, 30-fold or more, 35-fold or more, 40-fold or more, 45-fold or more, or 50-fold or more compared to the solubility of the active agent with the second unfractionated alkylated cyclodextrin composition.

A method for stabilizing an active agent is also provided, the method comprising:
(a) providing a fractionated alkylated cyclodextrin composition comprising an alkylated cyclodextrin; and
(b) combining the alkylated cyclodextrin composition with an active agent.

The method of stabilizing an active agent can be performed wherein the composition comprising one or more active agents and a fractionated alkylated cyclodextrin composition is present as a dry solution, a wet solution, an inhalable composition, a parenteral composition, a solid solution, a solid mixture, a granulate, a gel, and other active agent compositions known to persons of ordinary skill in the art.

In some embodiments, the method of stabilizing an active agent provides an active agent assay of 98% or more, 98.5% or more, 99% or more, or 99.5% or more of the active agent after the composition comprising one or more active agents and a fractionated alkylated cyclodextrin composition comprising a fractionated alkylated cyclodextrin is maintained at a temperature of 80° C. for a period of 120 minutes.

Generally, the fractionated alkylated cyclodextrin composition is present in an amount sufficient to stabilize the active agent. In some embodiments, the molar ratio of fractionated alkylated cyclodextrin composition:active agent is 0.1:1 to 10:1, 0.1:1 to 5:1, 0.1 to 1:1, 0.1:1 to 0.8:1, 0.1:1 to 0.5:1, 0.5:1 to 10:1, 0.5:1 to 5:1, 0.5 to 1:1, 0.5:1 to 0.8:1, 1:1 to 10:1, 1:1 to 5:1, or 5:1 to 10:1. In some embodiments, the molar ratio of fractionated alkylated cyclodextrin composition:active agent is greater than 10:1.

In some embodiments, the composition comprising the active agent and the fractionated alkylated cyclodextrin composition are maintained in a stability chamber for 1 day or more, 5 days or more, 10 days or more, 20 days or more, 30 days or more, 40 days or more, 50 days or more, 60 days or more, 70 days or more, 80 days or more, 90 days or more, 100 days or more, 110 days or more, or 120 days or more.

In some embodiments, the stability of the active agent with the fractionated alkylated cyclodextrin composition is increased (wt/wt on a mole basis) by 2-fold or more, 5-fold or more, 10-fold or more, 15-fold or more, 20-fold or more, 25-fold or more, 30-fold or more, 35-fold or more, 40-fold or more, 45-fold or more, or 50-fold or more compared to the stability of the active agent without the fractionated alkylated cyclodextrin composition.

Also provided is a method of comparatively analyzing the stabilizing ability of a fractionated alkylated cyclodextrin composition and an unfractionated alkylated cyclodextrin composition comprising:
(a) combining an unfractionated alkylated cyclodextrin composition with an active agent;
(b) combining a fractionated alkylated cyclodextrin composition with an active agent, wherein the active agent is the same as in (a);
(c) comparing the stability of the active agent in (a) to the solubility of the active agent in (b).

In some embodiments, the stability of the active agent with the fractionated alkylated cyclodextrin composition is increased (wt/wt on a mole basis) by 2-fold or more, 5-fold or more, 10-fold or more, 15-fold or more, 20-fold or more, 25-fold or more, 30-fold or more, 35-fold or more, 40-fold or more, 45-fold or more, or 50-fold or more compared to the stability of the active agent with an unfractionated alkylated cyclodextrin composition.

Also provided is a method of comparatively analyzing the stabilizing ability of two fractionated alkylated cyclodextrin compositions comprising:
(a) combining a first fractionated alkylated cyclodextrin composition with an active agent;
(b) combining a second fractionated alkylated cyclodextrin composition with an active agent, wherein the first and second fractionated alkylated cyclodextrin compositions are different and wherein the active agent is the same as in (a);
(c) comparing the stability of the active agent in (a) to the stability of the active agent in (b).

In some embodiments, the stability of the active agent with the first fractionated alkylated cyclodextrin composition is increased (wt/wt on a mole basis) by 2-fold or more, 5-fold or more, 10-fold or more, 15-fold or more, 20-fold or more, 25-fold or more, 30-fold or more, 35-fold or more, 40-fold or more, 45-fold or more, or 50-fold or more compared to the stability of the active agent with the second unfractionated alkylated cyclodextrin composition.

The fractionated alkylated cyclodextrin in the combination composition need not bind with another material, such as an active agent, present in a formulation containing it. However, if a fractionated alkylated cyclodextrin binds with another material, such a bond can be formed as a result of an inclusion complexation, an ion pair formation, a hydrogen bond, and/or a Van der Waals interaction.

An anionic derivatized fractionated alkylated cyclodextrin can complex or otherwise bind with an acid-ionizable agent. As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrometrically using methods such as $^1$H-NMR, $^{13}$C-NMR, or circular dichroism, for example, and by analysis of the phase solubility data for the acid-ionizable agent and anionic derivatized cyclodextrin. The artisan of ordinary skill in the art will be able to use these conventional methods to approximate the amount of each type of binding that is occurring in solution to determine whether or not binding between the species is occurring predominantly by non-covalent ionic binding or inclusion complex formation. Under conditions where non-covalent ionic bonding predominates over inclusion complex formation, the amount of inclusion complex formation, measured by NMR or circular dichroism, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term "non-covalent ionic bond" refers to a bond formed between an anionic species and a cationic species. A bond is non-covalent such that the two species together form a salt or ion pair. An anionic derivatized cyclodextrin provides the anionic species of the ion pair and the acid-ionizable agent provides the cationic species of the ion pair. Since an anionic derivatized fractionated alkylated cyclodextrin is multi-valent, it can form an ion pair with one or more acid-ionizable or otherwise cationic agents.

A liquid formulation described herein can be converted to a solid formulation for reconstitution. A reconstitutable solid composition of the present disclosure comprises an active agent, a derivatized fractionated alkylated cyclodextrin and optionally at least one other pharmaceutical excipient. A reconstitutable composition can be reconstituted with an aqueous liquid to form a liquid formulation that is preserved. The composition can comprise an admixture (minimal to no presence of an inclusion complex) of a solid derivatized fractionated alkylated cyclodextrin and an active agent-containing solid and optionally at least one solid pharmaceutical excipient, such that a major portion of the active agent is not complexed with the derivatized fractionated alkylated cyclodextrin prior to reconstitution. Alternatively, the composition can comprise a solid mixture of a derivatized fractionated alkylated cyclodextrin and an active agent, wherein a major portion of the active agent is complexed with the derivatized fractionated alkylated cyclodextrin prior to reconstitution. A reconstitutable solid composition can also comprise a derivatized fractionated alkylated cyclodextrin and an active agent where substantially all or at least a major portion of the active agent is complexed with the derivatized fractionated alkylated cyclodextrin.

A reconstitutable solid composition can be prepared according to any of the following processes. A liquid formulation as described herein is first prepared, then a solid is formed by lyophilization (freeze-drying), spray-drying, spray freeze-drying, antisolvent precipitation, aseptic spray drying, various processes utilizing supercritical or near supercritical fluids, or other methods known to those of ordinary skill in the art to make a solid for reconstitution.

A liquid vehicle included in a formulation described herein can comprise an aqueous liquid carrier (e.g., water), an aqueous alcohol, an aqueous organic solvent, a non-aqueous liquid carrier, and combinations thereof.

The formulation described herein can include one or more pharmaceutical excipients such as a conventional preservative, antifoaming agent, antioxidant, buffering agent, acidifying agent, alkalizing agent, bulking agent, colorant, complexation-enhancing agent, cryoprotectant, electrolyte, glucose, emulsifying agent, oil, plasticizer, solubility-enhancing agent, stabilizer, tonicity modifier, flavors, sweeteners, adsorbents, antiadherent, binder, diluent, direct compression excipient, disintegrant, glidant, lubricant, opaquant, polishing agent, complexing agents, fragrances, other excipients known by those of ordinary skill in the art for use in formulations, and combinations thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids, trolamine, and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other α-hydroxy acids, hydrochloric acid, ascorbic acid, phosphoric acid, sulfuric acid, tartaric acid, nitric acid, and others known to those of ordinary skill in the art.

As used herein, the term "antiadherent" is intended to mean an agent that prevents the sticking of solid dosage formulation ingredients to punches and dies in a tableting machine during production. Such compounds include, by way of example and without limitation, magnesium stearate, talc, calcium stearate, glyceryl behenate, polyethylene glycol, hydrogenated vegetable oil, mineral oil, stearic acid, and other materials known to one of ordinary skill in the art.

As used herein, the term "binder" is intended to mean a substance used to cause adhesion of powder particles in solid dosage formulations. Such compounds include, by way of example and without limitation, acacia, alginic acid, carboxymethylcellulose sodium, poly(vinylpyrrolidone), a compressible sugar, ethylcellulose, gelatin, liquid glucose, methylcellulose, povidone, pregelatinized starch, and other materials known to one of ordinary skill in the art.

When needed, binders can also be included in the dosage forms. Exemplary binders include acacia, tragacanth, gelatin, starch, cellulose materials such as methyl cellulose and sodium carboxymethylcellulose, alginic acids and salts thereof, polyethylene glycol, guar gum, polysaccharide, bentonites, sugars, invert sugars, poloxamers (Pluronic™ F68 (BASF, Florham Park, N.J.), Pluronic™ F127 (BASF, Florham Park, N.J.), collagen, albumin, gelatin, cellulosics in non-aqueous solvents, combinations thereof, and others known to those of ordinary skill in the art. Other binders include, for example, polypropylene glycol, polyoxyethylene-polypropylene copolymer, polyethylene ester, polyethylene sorbitan ester, polyethylene oxide, combinations thereof, and other materials known to one of ordinary skill in the art.

As used herein, a conventional preservative is a compound used to at least reduce the rate at which bioburden increases, but maintains bioburden steady or reduces bioburden after contamination. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl or butyl parabens, and others known to those of ordinary skill in the art. It is understood that some preservatives can interact with the alkylated cyclodextrin thus reducing the preservative effectiveness. Nevertheless, by adjusting the choice of preservative and the concentrations of preservative and the alkylated cyclodextrin adequately preserved formulations can be found.

As used herein, the term "diluent" or "filler" is intended to mean an inert substance used as a filler to create the desired bulk, flow properties, and compression characteristics in the preparation of a liquid or solid dosage form. Such compounds include, by way of example and without limitation, a liquid vehicle (e.g., water, alcohol, solvents, and the like), dibasic calcium phosphate, kaolin, lactose, dextrose, magnesium carbonate, sucrose, mannitol, microcrystalline cellulose, powdered cellulose, precipitated calcium carbonate, sorbitol, starch, and other materials known to one of ordinary skill in the art.

As used herein, the term "direct compression excipient" is intended to mean a compound used in compressed solid dosage forms. Such compounds include, by way of example and without limitation, dibasic calcium phosphate, and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, sodium metabisulfite, and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, 4-(2-hydroxyethyl)-1-piperazineethanesulfonic acid, lactic acid, tartaric acid, potassium metaphosphate, potassium phosphate, monobasic sodium acetate, sodium bicarbonate, tris, sodium tartrate, sodium citrate anhydrous and dehydrate, and others known to those of ordinary skill in the art.

A complexation-enhancing agent can be added to a formulation described herein. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water-soluble polymers, hydroxy acids, and other organic compounds typically used in preserved formulations to enhance the complexation of a particular agent with cyclodextrins.

Hydrophilic polymers can be used as complexation-enhancing, solubility-enhancing and/or water activity reducing agents to improve the performance of formulations containing a CD-based preservative. Loftsson has disclosed a number of polymers suitable for combined use with a cyclodextrin (underivatized or derivatized) to enhance the performance and/or properties of the cyclodextrin. Suitable polymers are disclosed in *Pharmazie* 56:746 (2001); *Int. J. Pharm.* 212:29 (2001); Cyclodextrin: From Basic Research to Market, 10th Int'l Cyclodextrin Symposium, Ann Arbor, Mich., US, May 21-24, p. 10-15 (2000); PCT Int'l Pub. No. WO 99/42111; *Pharmazie* 53:733 (1998); *Pharm. Technol. Eur.* 9:26 (1997); *J. Pharm. Sci.* 85:1017 (1996); European Patent Appl. No. 0 579 435; Proc. of the 9th Int'l Symposium on Cyclodextrins, Santiago de Comostela, E S, May 31-Jun. 3, 1998, pp. 261-264 (1999); *S.T.P. Pharma Sciences* 9:237 (1999); *Amer. Chem. Soc. Symposium Series* 737 (Polysaccharide Applications):24-45 (1999); *Pharma. Res.* 15:1696 (1998); *Drug Dev. Ind. Pharm.* 24:365 (1998); *Int. J. Pharm.* 163:115 (1998); Book of Abstracts, 216th Amer. Chem. Soc. Nat'l Meeting, Boston, August 23-27 CELL-016 (1998); *J. Controlled Release* 44:95 (1997); *Pharm. Res.* (1997) 14(11), S203; *Invest. Ophthalmol. Vis. Sci.* 37:1199 (1996); Proc. of the 23rd Int'l Symposium on Controlled Release of Bioactive Materials 453-454 (1996); *Drug Dev. Ind. Pharm.* 22:401 (1996); Proc. of the 8th Int'l Symposium on Cyclodextrins, Budapest, HU, Mar. 31-Apr. 2, 1996, pp. 373-376 (1996); *Pharma. Sci.* 2:277 (1996); *Eur. J. Pharm. Sci.* 4S:S144 (1996); 3rd Eur. Congress of Pharma. Sci. Edinburgh, Scotland, UK Sep. 15-17, 1996; *Pharmazie* 51:39 (1996); *Eur. J. Pharm. Sci.* 4S:S143 (1996); U.S. Pat. Nos. 5,472,954 and 5,324,718; *Int. J. Pharm.* 126:73 (1995); Abstracts of Papers of the Amer. Chem. Soc. 209:33-CELL (1995); *Eur. J. Pharm. Sci.* 2:297 (1994); *Pharm. Res.* 11:S225 (1994); *Int. J. Pharm.* 104:181 (1994); and *Int. J. Pharm.* 110:169 (1994), the entire disclosures of which are hereby incorporated by reference in their entirety.

Other suitable polymers are well-known excipients commonly used in the field of pharmaceutical formulations and are included in, for example, *Remington's Pharmaceutical Sciences*, 18th ed., pp. 291-294, A. R. Gennaro (editor), Mack Publishing Co., Easton, Pa. (1990); A. Martin et al., *Physical Pharmacy. Physical Chemical Principles in Pharmaceutical Sciences*, 3d ed., pp. 592-638 (Lea & Febinger, Philadelphia, Pa. (1983); A. T. Florence et al., *Physicochemical Principles of Pharmacy*, 2d ed., pp. 281-334, MacMillan Press, London, UK (1988), the disclosures of which are incorporated herein by reference in their entirety. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropylcellulose, their mixed ethers such as hydroxypropylmethylcellulose and other mixed ethers such as hydroxyethyl-ethylcellulose and hydroxypropylethylcellulose, hydroxypropylmethylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present disclosure.

As used herein, a fragrance is a relatively volatile substance or combination of substances that produces a detectable aroma, odor or scent. Exemplary fragrances include those generally accepted as safe by the U.S. Food and Drug Administration.

As used herein, the term "glidant" is intended to mean an agent used in solid dosage formulations to promote flowability of the solid mass. Such compounds include, by way of example and without limitation, colloidal silica, cornstarch, talc, calcium silicate, magnesium silicate, colloidal silicon, tribasic calcium phosphate, silicon hydrogel, and other materials known to one of ordinary skill in the art.

As used herein, the term "lubricant" is intended to mean a substance used in solid dosage formulations to reduce friction during compression. Such compounds include, by way of example and without limitation, calcium stearate, magnesium stearate, polyethylene glycol, talc, mineral oil, stearic acid, zinc stearate, and other materials known to one of ordinary skill in the art.

As used herein, the term "opaquant" is intended to mean a compound used to render a coating opaque. An opaquant can be used alone or in combination with a colorant. Such compounds include, by way of example and without limitation, titanium dioxide, talc, and other materials known to one of ordinary skill in the art.

As used herein, the term "polishing agent" is intended to mean a compound used to impart an attractive sheen to solid dosage forms. Such compounds include, by way of example and without limitation, carnauba wax, white wax, and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel®, FMC BioPolymer, Philadelphia, Pa.), carboxymethylcellulose calcium, croscarmellose sodium, alginic acid, sodium alginate, cellulose polacrilin potassium (e.g., Amberlite®, Rohm and Haas, Philadelphia, Pa.), alginates, sodium starch glycolate, gums, agar, guar, locust bean, karaya, pectin, tragacanth, crospovidone, and other materials known to one of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate, sodium saccharin, and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose, and others known to those of ordinary skill in the art. In some embodiments, the tonicity of the liquid formulation approximates the tonicity of blood or plasma.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol, and others known to those of ordinary skill in the art.

As used herein, the term "bulking agent" is intended to mean a compound used to add bulk to the solid product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

As used herein, the term "emulsifier" or "emulsifying agent" is intended to mean a compound added to one or more of the phase components of an emulsion for the purpose of stabilizing the droplets of the internal phase within the external phase. Such compounds include, by way of example and without limitation, lecithin, polyoxylethylene-polyoxypropylene ethers, polyoxylethylene-sorbitan monolaurate, polysorbates, sorbitan esters, stearyl alcohol, tyloxapol, tragacanth, xanthan gum, acacia, agar, alginic acid, sodium alginate, bentonite, carbomer, sodium carboxymethylcellulose, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

A solubility-enhancing agent can be added to the formulation described herein. A solubility-enhancing agent is a compound, or compounds, that enhance(s) the solubility of the active agent when in a liquid formulation. When such an agent is present, the ratio of cyclodextrin/active agent can be changed. Suitable solubility enhancing agents include one or more organic solvents, detergents, soaps, surfactants, and other organic compounds typically used in parenteral formulations to enhance the solubility of a particular agent.

Suitable organic solvents include, for example, ethanol, glycerin, polyethylene glycols, propylene glycol, poloxomers, and others known to those of ordinary skill in the art.

Formulations comprising the alkylated cyclodextrin composition described herein can include oils (e.g., fixed oils, peanut oil, sesame oil, cottonseed oil, corn oil olive oil, and the like), fatty acids (e.g., oleic acid, stearic acid, isostearic acid, and the like), fatty acid esters (e.g., ethyl oleate, isopropyl myristate, and the like), fatty acid glycerides, acetylated fatty acid glycerides, and combinations thereof. Formulations comprising the alkylated cyclodextrin composition described herein can also include alcohols (e.g., ethanol, iso-propanol, hexadecyl alcohol, glycerol, propylene glycol, and the like), glycerol ketals (e.g., 2,2-dimethyl-1,3-dioxolane-4-methanol, and the like), ethers (e.g., poly (ethylene glycol) 450, and the like), petroleum hydrocarbons (e.g., mineral oil, petrolatum, and the like), water, surfactants, suspending agents, emulsifying agents, and combinations thereof.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Formulations comprising the alkylated cyclodextrin composition described herein can also include biological salt(s), sodium chloride, potassium chloride, and other electrolyte(s).

Since some active agents are subject to oxidative degradation, a liquid formulation described herein can be substantially oxygen-free. For example, the headspace of a container containing a liquid formulation can made oxygen-free, substantially oxygen-free, or oxygen-reduced by purging the headspace with an inert gas (e.g., nitrogen, argon, carbon dioxide, and the like), or by bubbling an inert gas through a liquid formulation. For long-term storage, a liquid formulation containing an active agent subject to oxidative degradation can be stored in an oxygen-free or oxygen-reduced environment. Removal of oxygen from the formulation will enhance preservation of the formulation against aerobic microbes; whereas, addition of oxygen to the formulation will enhance preservation against anaerobic microbes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep, non-humans, and humans.

A formulation described herein will comprise an active agent present in an effective amount. By the term "effective amount," is meant the amount or quantity of active agent that is sufficient to elicit the required or desired response, or in other words, the amount that is sufficient to elicit an appreciable biological response when administered to a subject.

The compositions described herein can be present in formulations for dosage forms such as a reconstitutable solid, tablet, capsule, pill, troche, patch, osmotic device, stick, suppository, implant, gum, effervescent composition, injectable liquid, ophthalmic or nasal solutions, or inhalable powders or solutions.

Also provided are methods of preparing a liquid formulation comprising one or more active agents and a fractionated alkylated cyclodextrin composition, wherein the fractionated alkylated cyclodextrin composition comprises an alkylated cyclodextrin. A first method comprises: forming a first aqueous solution comprising a fractionated alkylated cyclodextrin composition; forming a second solution or suspension comprising one or more active agents; and mixing the first and second solutions to form a liquid formulation. A similar second method comprises adding one or more active agents directly to a first solution without formation of the second solution. A third method comprises adding a fractionated alkylated cyclodextrin composition directly to the solution/suspension containing one or more active agents. A fourth method comprises adding a solution comprising one or more active agents to a powdered or particulate fractionated alkylated cyclodextrin composition. A fifth method comprises adding one or more active agents directly to a powdered or particulate fractionated alkylated cyclodextrin composition, and adding the resulting mixture to a second solution. A sixth method comprises creating a liquid formulation by any of the above methods and then isolating a solid material by lyophilization, spray-drying, aseptic spray drying, spray-freeze-drying, antisolvent precipitation, a process utilizing a supercritical or near supercritical fluid, or another method known to those of ordinary skill in the art to make a powder for reconstitution.

Specific embodiments of the methods of preparing a liquid formulation include those wherein: 1) the method further comprises sterile filtering the formulation using a filtration medium having a pore size of 0.1 μm or larger; 2) the liquid formulation is sterilized by irradiation or autoclaving; 3) the method further comprises isolating a solid from the solution; 4) the solution is purged with nitrogen or argon or other inert pharmaceutically acceptable gas such that a substantial portion of the oxygen dissolved in, and/or in surface contact with, the solution is removed.

A reconstitutable solid pharmaceutical composition comprising one or more active agents, a fractionated alkylated cyclodextrin composition and optionally at least one other pharmaceutical excipient is also provided. When this composition is reconstituted with an aqueous liquid to form a preserved liquid formulation, it can be administered by injection, infusion, topically, by inhalation, or orally to a subject.

Some embodiments of the reconstitutable solid pharmaceutical composition includes those wherein: 1) the pharmaceutical composition comprises an admixture of a fractionated alkylated cyclodextrin composition and a solid comprising one or more active agents and optionally at least one solid pharmaceutical excipient, such that a major portion of the active agent is not complexed with an alkylated cyclodextrin prior to reconstitution; and/or 2) the composition comprises a solid mixture of a fractionated alkylated cyclodextrin composition and one or more active agents, wherein a major portion of the one or more active agents is complexed with the fractionated alkylated cyclodextrin prior to reconstitution.

A composition described herein can be used in a pharmaceutical dosage form, pharmaceutical composition or other such combination of materials. These fractionated alkylated cyclodextrin compositions are also useful as, but not limited to, analytical reagents, food and cosmetics adjuvants and/or additives, and as environmental clean-up agents.

In view of the above description and the examples below, one of ordinary skill in the art will be able to practice the invention as claimed without undue experimentation. The foregoing will be better understood with reference to the following examples that detail certain procedures for the preparation of molecules, compositions, and formulations according to the present disclosure. All references made to these examples are for the purposes of illustration. The following examples should not be considered exhaustive, but merely illustrative of only a few of the many embodiments contemplated by the present disclosure.

EXAMPLES

Example 1

Analysis of SBE-CD Derivative Compositions Using Capillary Electrophoresis

A Beckman P/ACE 2210 capillary electrophoresis system coupled with a UV absorbance detector (Beckman Instruments, Inc., Fullerton, Calif.) was used to analyze solutions of each SBE-β CD derivative and SBE-γ CD derivative. The separation was performed at 25° C. using a fused silica capillary (50 μm inner diameter, 57 cm total length, and 50 cm effective length) with a pH adjusted running buffer (30 mM benzoic acid and 100 mM TRIS (tris-hydroxymethyl-aminomethanol)).

The silica capillary was treated with the following wash sequence before each injection: water, 0.01 N NaOH, and running buffer. The detector was set at 214 nm. The voltage was 30 kV. Samples were introduced by pressure injections: 20 s at 0.5 psi. An exemplary capillary electrophoresis electropherogram of a sample of Captisol® (Batch 17CX01.HQ00026) is provided in FIG. 1.

Example 2

$SBE_{6.6}$-β-CD Synthesis

A $SBE_{6.6}$-β-CD composition was synthesized according to the following procedure, in which a β-cyclodextrin in an alkaline aqueous medium was derivatized with an SBE precursor to form the $SBE_{6.6}$-β-CD. An aqueous solution of sodium hydroxide was prepared by charging 61.8 kg of sodium hydroxide to 433 kg of water for a 12.5% w/w solution. The reactor contents were heated to 40° C. to 50° C. before beginning the addition of 270 kg of β-CD over 30 to 60 minutes. The reaction temperature was adjusted to 65° C. to 95° C. before the addition of 259 kg of 1,4-butane sultone over 30 to 60 minutes. Over the next 6 hours the pH of the solution was maintained above 9 using an aqueous solution of sodium hydroxide. Following the reaction an additional 13.5 kg of sodium hydroxide as a 20% solution was charged to the reaction. The contents were maintained at 70° C. to 80° C. until the residual level of 1,4-butane sultone was sufficiently low. The contents were cooled to less than 30° C. and the reaction solution was adjusted to pH 6.5-7.5 with aqueous solution of hydrochloric acid. This process yielded 350 to 450 kg of $SAE_{6.6}$-CD.

Example 3

$SBE_{6.6}$-β-CD Diafiltration and Ultrafiltration

The $SBE_{6.6}$-β-CD of Example 2 was purified by the following procedure. The reaction solution was diluted with 800 kg of water. The solution was transferred and further diluted with 500 kg of water. Diafiltration was initiated using a Millipore Helicon Automated Ultrafiltration System using 1000 MWCO spiral wound regenerated cellulose membranes having at least 750 ft$^2$ of membrane area and maintaining a constant solution volume (t 1%) until a sample of the returnate had 25 ppm or less of sodium chloride. The solution was concentrated by ultrafiltration until an appropriate solution mass was achieved.

Example 4

$SBE_{6.6}$-β-CD Carbon Processing

Following the diafiltration and ultrafiltration in Example 3, the $SBE_{6.6}$-β-CD was carbon purified by the following procedure. A column was charged with 32 kg (11-12% wt. of the starting amount of β-cyclodextrin) of Shirasagi® DC32 granular activated carbon and washed thoroughly with water until the wash samples have a constant conductivity. The ratio of $SBE_{6.6}$-β-CD to activated carbon was 8.4:1 to 8.5:1. Once washed, the reaction solution was passed (recycled) through the carbon for at least 2 hours to complete a first treatment cycle.

A second column was charged with 32 kg (about 11-12% wt. of the starting amount of β-cyclodextrin) of Shirasagi® DC32 granular activated carbon and washed thoroughly with water until the wash samples had a constant conductivity. Once washed, the reaction solution was passed through the carbon for at least 2 hours to complete a second treatment cycle.

Example 5

SBE$_{6.6}$-β-CD Concentration and Isolation

The carbon-treated SBE$_{6.6}$-β-CD solutions prepared in Example 4 were concentrated and isolated using the following procedure. A SBE$_{6.6}$-β-CD solution was filtered through 0.65 μm and 0.22 μm filters and then concentrated at a reduced pressure of −0.6 bar to −0.7 bar at a temperature of 65° C. to 72° C., with agitation at 70 rpm to 100 rpm, until a solution having a SBE$_{6.6}$-β-CD concentration of 50% by weight was achieved. The concentrated solution was cooled to below 60° C., and then filtered through 0.65 μm and 0.22 μm filters. The filtered solution was then spray dried using a fluidized spray dryer ("FSD") system at an inlet temperature of 170° C., an initial pressure of 20 bar, and chambers 1-3 having set points of 125° C., 105° C., and 100° C., respectively.

Example 6

Figure 2:
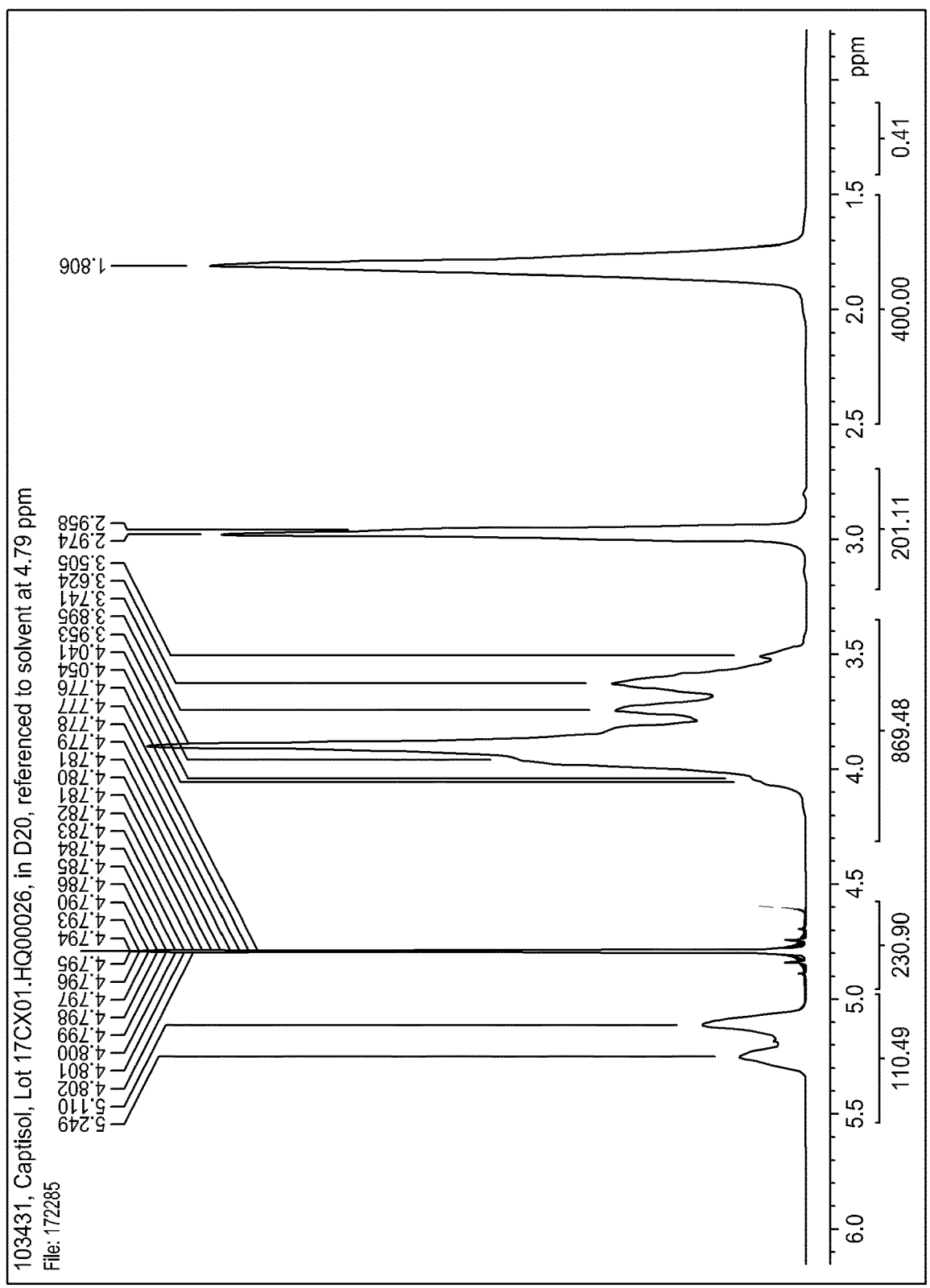
FIG. 2 provides an exemplary $^1$H-NMR for a sample of Captisol® (Batch 17CX01.HQ00026).
Figure 3:
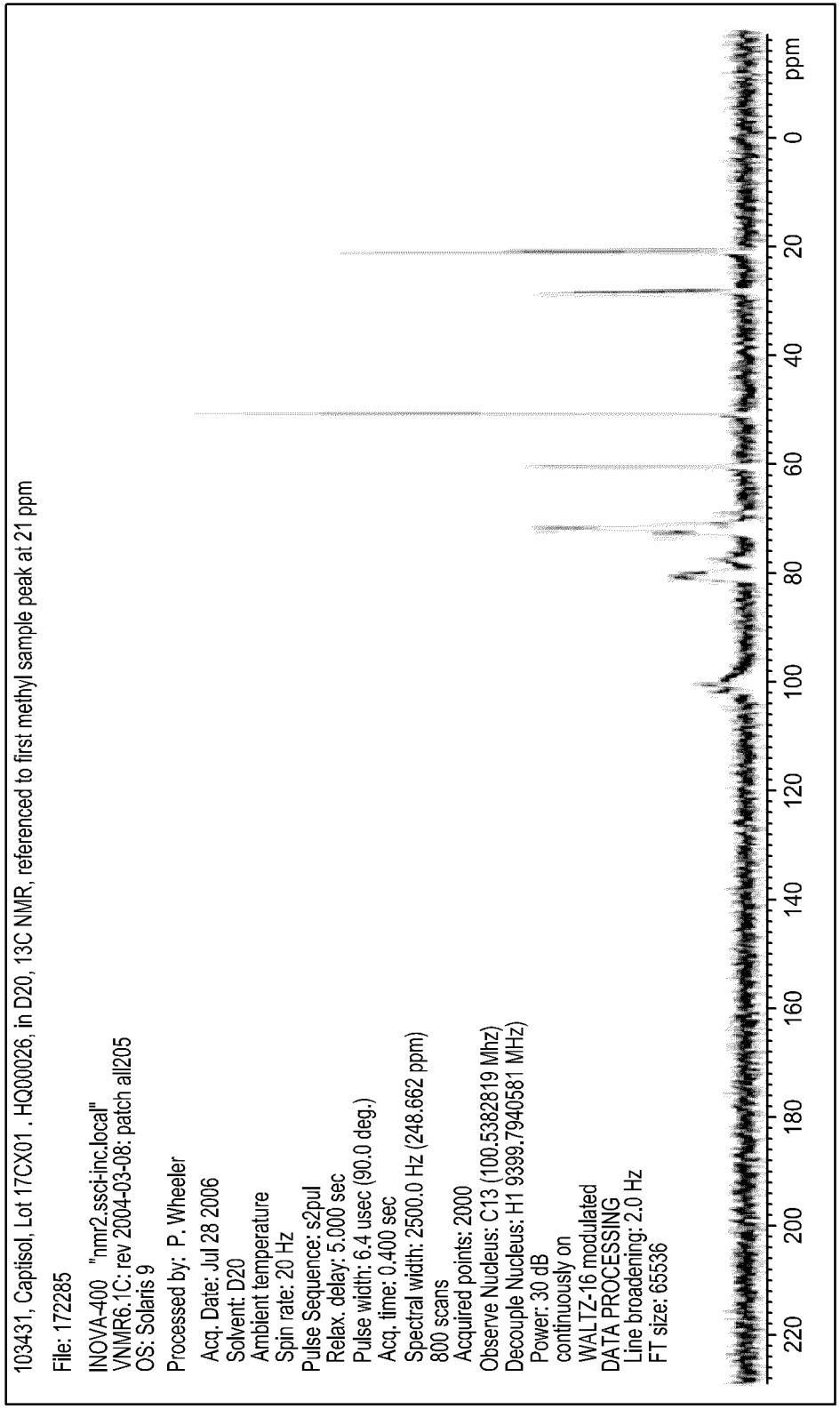
FIG. 3 provides an exemplary $^{13}$C-NMR spectra for a sample of Captisol® (Batch 17CX01.HQ00026).

Determination of Cyclodextrin Substitution Pattern by $^{1}$H-NMR, $^{13}$C-NMR, COSY-NMR, and HMQC on Bruker Avance®400 or 500 Instrument Determination of the substitution pattern is conducted according to the method of Example 6 of U.S. Pat. No. 7,625,878, the relevant disclosures of which are hereby incorporated by reference. Exemplary $^{1}$H-NMR and $^{13}$C-NMR spectra for a sample of Captisol® (Batch 17CX01.HQ00026) are respectively provided in FIG. 2 and FIG. 3.

Example 7

HPLC Separation and Collection of a Fractionated SBE-CD

An exemplary fractionated SBE-CD composition can be prepared using the following procedure. A SBE-CD (1%) in HPLC grade water could be injected into a Series 20A Prominence HPLC (Shimadzu Scientific Instruments) using a Discovery C18 chromatographic column (Supelco Analytical) and a Corona Charged Aerosol Detector (ESA Bioscience). Mobile Phase A: 5% acetonitrile/95% 30 mM ammonium acetate and 7.5 mM tributylamine; Mobile Phase B: 90% acetonitrile/10% 30 mM ammonium acetate and 7.5 mM tributylamine. The mobile phase gradient started at 75% A:25% B and ramped to 60% A:40% B over 25 minutes. The column temperature was held at 30° C. and the pump flow was held at 1 mL/min.

Charged aerosol detection is a unique detection technique in which the HPLC column eluent is first nebulized with a nitrogen stream into suitable size particle droplets. A secondary nitrogen stream is charged positively as it passes a high voltage corona wire. The amount of charge acquired by the particle is directly proportional to the concentration of ions contained in the droplet and then transferred to a collector where this charge is measured by a highly sensitive electrometer generating a signal in direct proportion to the quantity of analyte present in the sample. As the charged aerosol detector (CAD) is a destructive detection method the flow is split to divert the majority volume to a fraction collector and individual solutions of modified cyclodextrins containing the same number of alkylated units can be collected. To further purify the collected fractions of singly substituted cyclodextrins, the individual solutions can be dried under vacuum to remove the organic and buffer constituents of the mobile phase (water, acetonitrile, ammonium acetate, and tributylamine) which are volatile to leave highly pure singly substituted cyclodextrin.

Example 8

Semi-Preparative HPLC Separation and Collection of Fractionated SBE-CD

An exemplary similarly fractionated SBE-CD composition can be prepared on a semi-preparative scale using the following procedure. 10 mg of a SBE-CD (in water) with an ADS of between 2 and 14 could be loaded onto a Series 20A Prominence HPLC (Shimadzu Scientific Instruments) using a 10 μm Discovery C18 (25 cm×21.1 mm) chromatographic column (Supelco Analytical) and a Corona Charged Aerosol Detector (ESA Bioscience) or evaporative light scattering detector (ELSD). Mobile Phase A: 5% acetonitrile/95% 30 mM ammonium acetate and 7.5 mM tributylamine; Mobile Phase B: 90% acetonitrile/10% 30 mM ammonium acetate and 7.5 mM tributylamine. The mobile phase gradient could start at 95% A:5% B and ramp to 50% A:50% B over 120 minutes. Alternatively an appropriate isocratic run could be performed using the same mobile phase of acetonitrile, ammonium acetate, and tributylamine buffer for run times as long as 120 minutes. The column temperature would be held between 20° C. and 30° C. and the flow rate would be held between 5 mL/min and 15 mL/min. As the charged aerosol detector is a destructive detection method the flow would split to divert the majority volume to a fraction collector and individual solutions of modified cyclodextrins containing the same number of alkylated units would be collected. The purified fractions of singly substituted cyclodextrins would be evaporated to dryness under vacuum to remove the organic and buffer constituents of the mobile phase. The weight of each fraction of material isolated would depend on the ADS of the material loaded on the column.

Example 9

Commercial Scale HPLC Separation and Collection of Fractionated SBE-CD

An exemplary fractionated SBE-CD composition can be prepared on a commercial scale using the following procedure. Grams to kilograms of a SBE-CD with an ADS of between 2 and 14 could be loaded onto a 10 to 40 inch diameter C18 HPLC column. Mobile Phase A: 5% acetonitrile/95% 30 mM ammonium acetate and 7.5 mM tributylamine; Mobile Phase B: 90% acetonitrile/10% 30 mM ammonium acetate and 7.5 mM tributylamine. The mobile phase gradient could start at 95% A:5% B and ramp to 50% A:50% B for a run time up to 360 minutes. Alternatively, an isocratic gradient could be used with a mixture of acetonitrile, ammonium acetate, and tributylamine buffer for run times as long as 360 minutes. The column would be held at between 20° C. and 30° C. and the flow rate would be held between 20 mL/min and 200 L/min. The fractionation of the material would either not be monitored by a detector and each fraction isolated by time or an in-line CAD or ELSD detector would determine when fractions would be taken. The purified fractions of singly substituted cyclodextrins would be evaporated to dryness under vacuum to remove the organic and buffer constituents of the mobile phase. The weight of each fraction of material isolated would depend on the ADS of the material loaded on the column.

Example 10

Comparison of Captisol Separation Using Capillary Electrophoresis and Charged Aerosol Detector Capillary electrophoresis (CE) separates ions and other molecules based on their movement under the influence of voltage across a capillary. When ions are introduced to a charge they will migrate to the oppositely charged electrode. Therefore, for SBE-CD, the negatively charged sulfobutyl ether groups will migrate to the positively charged electrode. In addition to the separation based on the charge, CE also separates based on the hydrodynamic size of the ion or compound. Hydrodynamic size can be correlated with the mass of a molecule. In the case of SBE-CD that is a mixture of sulfobutyl ether species, CE can separate based on the number of charges on a fraction of the SBE species. Therefore SBE species with one SBE group (SBE1) on a cyclodextrin will separate first due to the lower mass of that species. In comparison SBE with ten SBE groups (SBE10) on a cyclodextrin will separate last based on the higher mass of that species. These SBE-CD species are indirectly detected on CE through the disappearance of benzoic acid in the run buffer. Benzoic acid will seek out the cavity of the SBE-CD and no longer be seen by detector. It is conceivable that CE could be used to isolate nanoliter ($1/1000^{th}$ of a microliter) amounts of each fraction. This would however lead to fractions that contained benzoic acid and excess sodium hydroxide.

The HPLC method using an in-line CAD detector will separate ions or molecules on a C18 column using the ion pairing capacity of the mobile phase. In this way, the SBE-CD fractions are separated by charge with the lowest charged species (SBE1) eluting first and the highest charged species (SBE10) eluting last. Once these species are separated by the HPLC method they can be detected by the Corona CAD detector which nebulizes a fraction of the HPLC eluent using nitrogen. The dried droplets are then charged with another stream of nitrogen and a voltage wire. The amount of charge of the ion is proportion to the ion size. The majority of the HPLC elute is collected in a fraction collector system that based on the output of the CAD detector will collect single SBE-CD fractions.

Example 11

Evaluation of Fractionated SAE-CD in the Solubilization of Drug Derivatives

Various fractionated SAE-CD lots can be evaluated for their ability to solubilize several drug derivatives using the following procedure. 0.04 M stock solutions of each selected SAE-CD can be prepared with purified water. Clarity of solutions can be determined by visual inspection or instrumentally. A clear solution is at least clear by visual inspection with the unaided eye. Each drug derivative, tested in duplicate, can be added to either 2 or 4 mL of the SAE-CD solution.

The drug derivatives can be weighed in amounts in excess of the anticipated solubilities directly into Teflon-lined screw-capped vials. These amounts provide a minimum of 3 mg/mL of solids. Each vial can then receive the appropriate amount of SAE-CD solution. The vials can be vortexed and sonicated to aid in wetting the solids with the fluid. The vials can then be placed on a lab quake or a roller mixer for equilibration. The vials can be visually inspected periodically to assure that the solids were adequately being wetted and in contact with the fluid. The time points for sampling would typically be 24 hours.

At the end of the equilibration time for each stage, the vials can be decanted or centrifuged and 1 ml of the supernatant removed. The removed supernatant could then be filtered using a 0.22 µm syringe filter and diluted with the mobile phase to an appropriate concentration within the standard curve. The samples can then be analyzed by HPLC to determine concentration of solubilized drug derivatives.

Example 12

Evaluation of SAE-CD in the Solubilization of Posaconazole

Comparative evaluation of various fractionated SAE-CD lots processed with a single or a double carbon treatment with posaconazole can be examined by Hunter colorimetric and HPLC analysis. A general solubility procedure is provided below. Aqueous solution samples of posaconazole (5 mg/mL) and 100 mM of a fractionated SAE-CD at pH 3 can be prepared. All solution samples could be filtered through a 0.22 mm PVDF filter, and separated into vials. The initial solution can be analyzed on a Perkin Elmer Lambda 35 UV/Vis spectrophotometer, scanning from 190 to 400 nm at a speed of 240 nm/min with a slit of 1 nm and analyzed on a Hunter Lab Ultrascan colorimeter using Hunter Lab Universal Software (version 4.10). Samples can be added to a 1 cm Hunter cuvette The sample can be blanked against water before analysis. Remaining samples can be placed into a 60° C. oven for 7 days before reanalyzing for color changes. The UV analysis can be performed to show the initial content of the fractionated SAE-CD UV impurities while the Hunter color analysis of the formulation samples is an indicator of Posaconazole stability in solution with the fractionated SAE-CD. The greater the color the more impurities are formed.

Example 13

Evaluation of SAE-CD in the Stability of an API Drug Formulation

Comparative evaluation of various fractionated SAE-CD lots processed with a single or a double carbon treatment with an API drug formulation can be examined by UV spectroscopy and HPLC analysis. A general solubility procedure is provided below. Aqueous solution samples of the API drug formulation can be prepared with an API concentration of 7.5 mg/mL and fractionated SAE-CD concentration of 150 mg/mL.

Tartaric acid can be added to water until the fractionated SAE-CD is dissolved. A solution should be achieved within about 10 minutes and the API is added. The mixture can be stirred about an hour and heated before sterilely filtering the solution. The formulation can be performed on multiple fractionated SAE-CD lots, some that have had a single carbon treatment and others that have had two carbon treatments. Solution samples can be placed into a stability chamber at 50° C. for up to 3 months. Samples can be removed during this time and HPLC analysis performed.

Example 14

Figure 4:
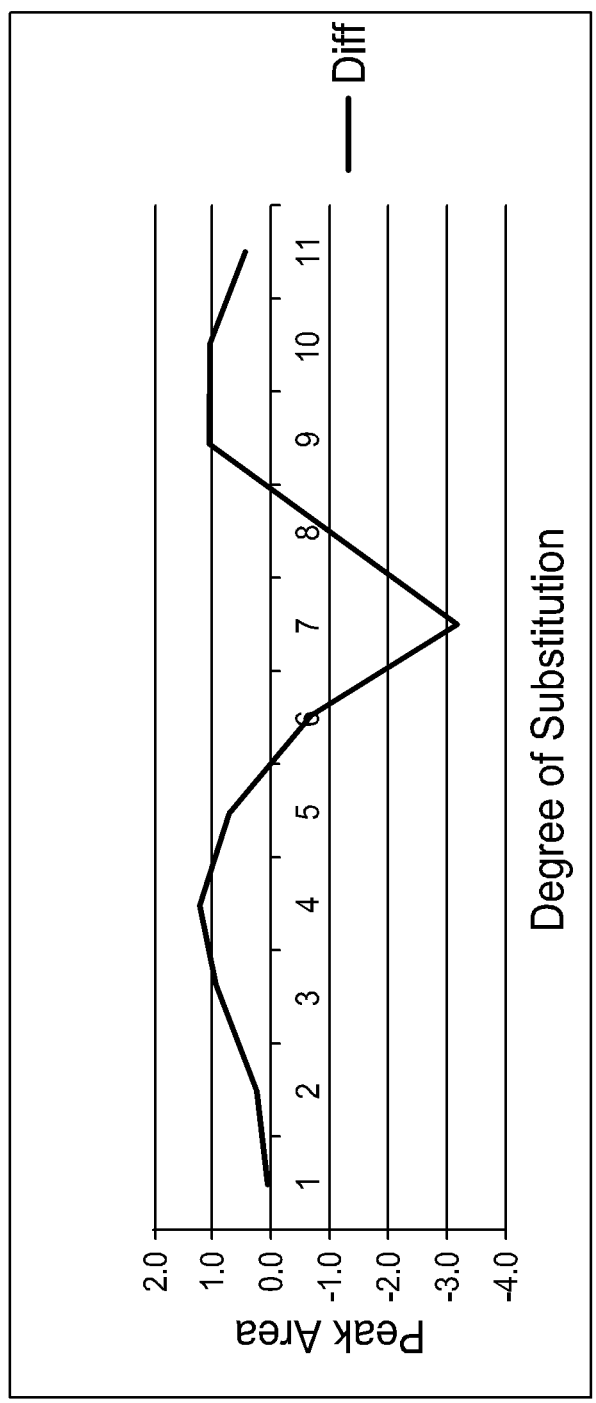
FIG. 4 provides a graphic representation comparing the calculated peak area for each degree of substitution for a SBE-CD composition using capillary electrophoresis and high performance liquid chromatography coupled with a charged aerosol detector.

Comparison of Normalized Area Percent of SBE-CD Using Capillary Electrophoresis and a Charged Aerosol Detector As shown in the following Table, normalized area percent (labeled norm area) for single substitutions of a SBE-CD sample (Lot No. 17CX1.HQ00033) was measured using capillary electrophoresis (labeled CE) and a Series 20A Prominence HPLC (Shimadzu Scientific Instruments) using a 10 µm Discovery C18 (25 cm×21.1 mm) chromatographic column (Supelco Analytical) and a Corona Charged Aerosol Detector (ESA Bioscience). Average degree of substitution (ADS) was also measured for both methods with capillary electrophoresis providing an ADS of 6.75 and Charged Aerosol Detector providing an ADS of 6.74. As shown in FIG. 4, comparison of the normalized area percent measurements (labeled Diff) showed similar results for capillary electrophoresis and a Charged Aerosol Detector. Other methods of determining the content of each fraction include mass spectroscopy and elemental analysis. However, these methods have been found to be limited in sensitivity and result in large variation in the ADS measurement.

| Peak No. | SBE-CD | CE | norm area | C18 HPLC | norm area | Diff |
|---|---|---|---|---|---|---|
| 1 | I | 0.0 | 0.0 | 0.07 | 0.07 | 0.1 |
| 2 | II | 0.2 | 0.4 | 0.44 | 0.88 | 0.2 |
| 3 | III | 1.3 | 3.9 | 2.15 | 6.45 | 0.9 |
| 4 | IV | 5.0 | 20.0 | 6.19 | 24.76 | 1.2 |
| 5 | V | 12.4 | 62.0 | 13.05 | 65.25 | 0.7 |
| 6 | VI | 21.3 | 127.8 | 20.67 | 124.02 | −0.6 |
| 7 | VII | 27.4 | 191.8 | 24.16 | 169.12 | −3.2 |
| 8 | VIII | 21.2 | 169.6 | 20.02 | 160.16 | −1.2 |
| 9 | IX | 8.9 | 80.0 | 9.98 | 89.82 | 1.1 |
| 10 | X | 1.9 | 19.0 | 2.87 | 28.7 | 1.0 |
| 11 | XI | 0.0 | 0.0 | 0.4 | 4.4 | 0.4 |
| | | | ADS = 6.75 | | ADS = 6.74 | |

Example 15

Preparation of a $SBE_{10.5}$-β-CD Composition

A $SBE_{10.5}$-β-CD composition was prepared using the following procedure. A β-cyclodextrin was dissolved in an aqueous solution of sodium hydroxide (11 equivalents), heated to 50° C., and stirred until the β-cyclodextrin was completely dissolved. Once dissolution was complete, the reaction temperature was increased to 70° C. to 75° C. before the addition of 20 equivalents of 1,4-butanesultone over 120 minutes. The reaction was heated at 70° C. for at least an additional 16 hours. Following the reaction, the mixture was cooled and diluted with water (roughly one half the total reaction volume). The solution was neutralized with HCl to a pH of 6.5 to 7.5, purified with carbon, and filtered through a 0.45 µm filter.

The solution was purified by ultrafiltration using a Millipore Helicon Automated Ultrafiltration System using 1000 MWCO spiral wound regenerated cellulose membranes having at least 750 ft² of membrane area and maintaining a constant solution volume (±1%). The ultrafiltration end point was determined by capillary electrophoresis wherein the filtrate showed no or substantially no presence of 4-hydroxybutane-1-sulfonic acid and/or Disodium Bis (4-Sulfobutyl)Ether, and by Osmolarity, wherein the permeate samples had little to no ion present. The resulting solution was concentrated to roughly a 50% solution by rotary evaporation at 50° C. to 60° C. under a less than 30 mmHg vacuum. The solution was freeze-dried to produce 49.1 grams of $SBE_{10.5}$-β-CD with a yield of 98.1% based on the starting β-cyclodextrin material.

The following Table presents the calculation of the ADS as determined by the peak areas from Charged Aerosol Detector. The ADS of the SBE-CD was determined to be 10.5.

| SBE-CD fraction | Migration Time (mm) | Peak Area | Corrected Area | Normalized Area |
|---|---|---|---|---|
| I | | | | |
| II | | | | |
| III | | | | |
| IV | | | | |
| V | | | | |
| VI | | | | |
| VII | | | | |
| VIII | 20.529 | 4535 | 11045.35048 | 7.094127317 |
| IX | 21.875 | 20875 | 47714.28571 | 30.64558416 |
| X | 23.058 | 28807 | 62466.38911 | 40.12045776 |
| XI | 24.2 | 16684 | 34471.07438 | 22.13983077 |
| XII | 25.425 | 1798 | 3535.889872 | 2.271005612 |
| Sum | | | 155697.0997 | |

Example 16

Procedure for Evaluating the Solubility of Active Agents in Fractionated Alkylated Cyclodextrin Compositions Fractionated alkylated cyclodextrin compositions can be evaluated for their ability to solubilize active agents using the following procedure. A 0.04 M stock solution of each fractionated alkylated cyclodextrin composition can be prepared with purified water. Clarity of solutions can be determined by visual inspection or instrumentally. A clear solution is at least clear by visual inspection with the unaided eye.

The active agent, in amounts in excess of the anticipated solubility (a minimum of 3 mg/mL), can be measured directly into a Teflon-lined screw-capped vial. To the vial can be added between 2 mL and 4 mL of the fractionated alkylated cyclodextrin composition solution. The vial can be vortexed and sonicated to aid in wetting the solids with the fluid. The vial can then be placed on a lab quake or a roller mixer for equilibration. The vial can be visually inspected periodically to assure that the solids are adequately being wetted and are in contact with the fluid. The time points for sampling is typically 24 hours for a sample.

At the end of the equilibration time for each stage, the vial can be decanted or centrifuged and 1 ml of the supernatant can be removed. The removed supernatant can be filtered using a 0.22 µm syringe filter, and diluted with the mobile phase to an appropriate concentration within the standard curve. The samples can be analyzed by HPLC to determine the concentration of solubilized active agents.

Example 17

Procedure for Comparing Solubility of Itraconazole in a SBE-CD Composition and a Fractionated SBE-CD Composition Using the procedure of Example 16, individual fractionated SBE-CD compositions (having a single degree of substitution of 1, 2, 3, 4, 5, 6, 7, 8, 9, and 10) can be compared to an unfractionated SBE$_{6.5}$-CD composition (containing a mixture of substituents having a degree of substitution from 1-10) for the ability to solubilize itraconazole. The samples can be examined by analytical methods including HPLC to determine which fractionated SBE-CD compositions have improved solubility compared to the unfractionated SBE-CD.

Figure 5:
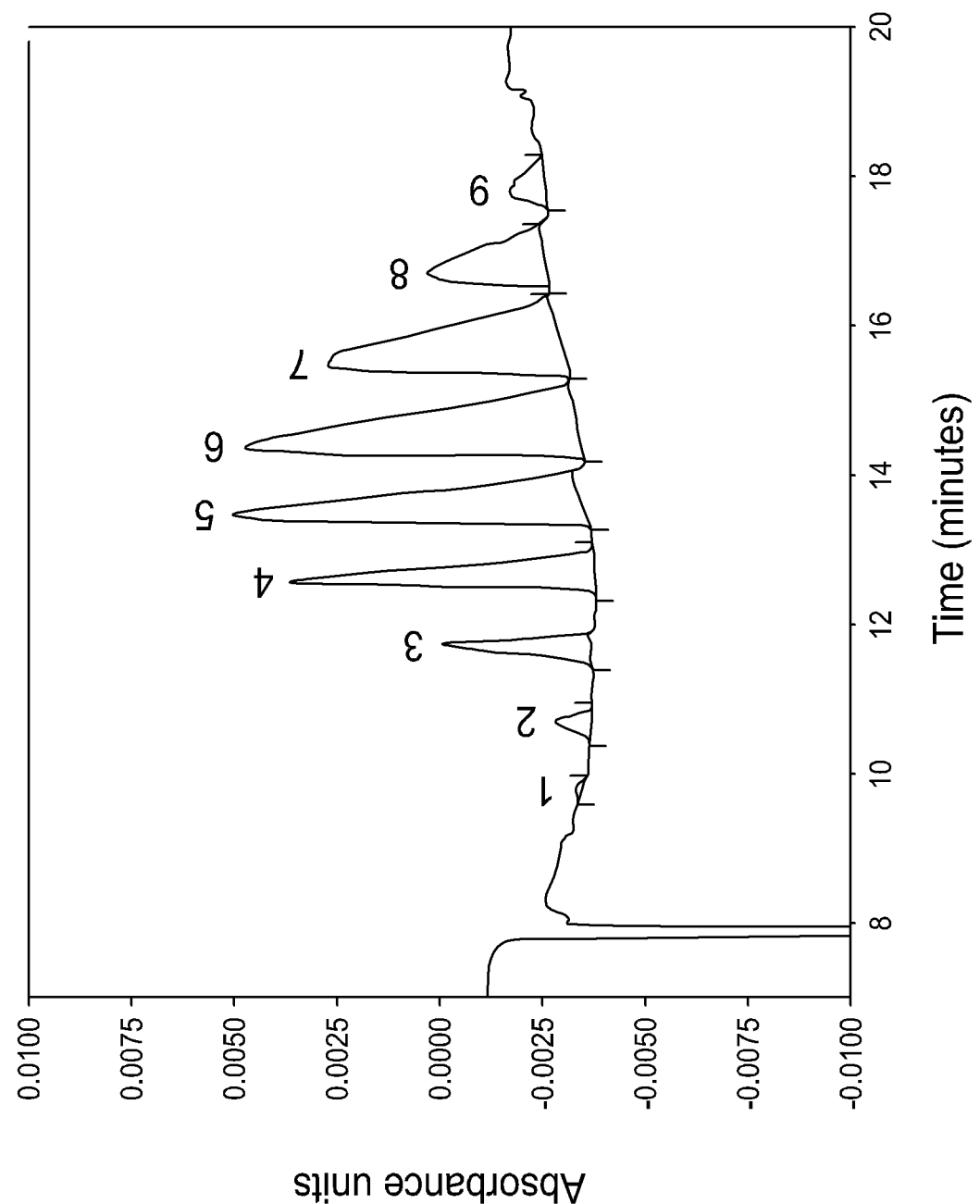
FIG. 5 provides a chromatograph of a SBE-CD composition obtained using a charged aerosol detector.
Figure 6:
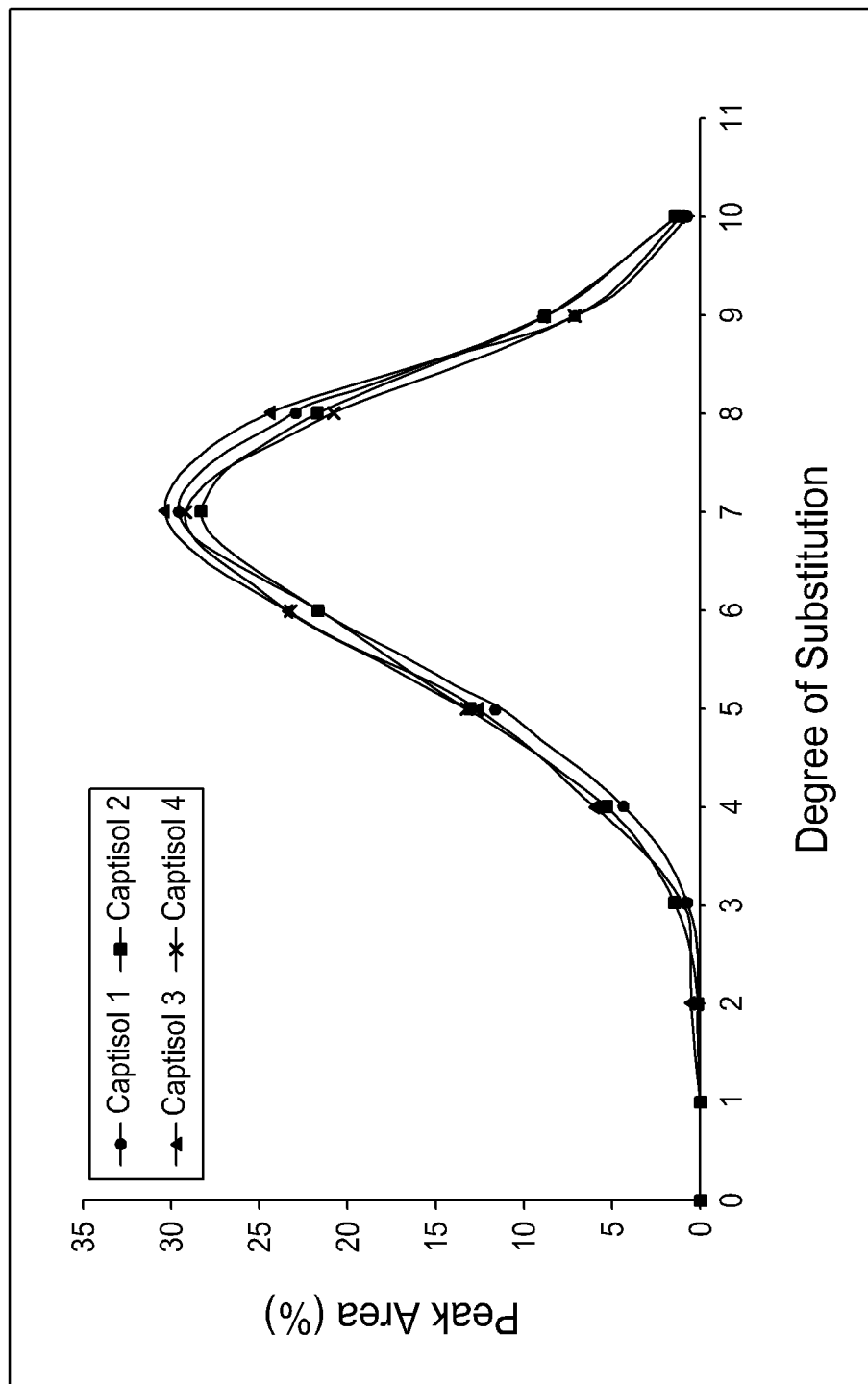
FIG. 6 provides a graphic representation of the distribution pattern obtained using capillary electrophoresis for four mixtures of Captisol®.

A chromatograph of a SBE-CD composition obtained according to the method of Example 7 is shown in FIG. 5. As shown in FIG. 5, the composition contains 4-7 substitutions with smaller amounts of 3 and 8 substitutions present. The chromatograph of FIG. 5 provides the fingerprint for the purified and isolated fractions of SBE-CD. To provide contrast, a fingerprint for a mixed SBE-CD composition is shown in FIG. 6. Calculations of area and area percent for the chromatograph of FIG. 5 are provided in the following Table.

| Peak No. | Migration Time (min) | Area (mV* min) | Area Percent |
| --- | --- | --- | --- |
| 1 | 9.796 | 1790 | 0.189 |
| 2 | 10.721 | 11697 | 1.232 |
| 3 | 11.758 | 42215 | 4.446 |
| 4 | 12.596 | 118249 | 12.455 |
| 5 | 13.492 | 201492 | 21.222 |
| 6 | 14.408 | 261918 | 27.587 |
| 7 | 15.517 | 207461 | 21.851 |
| 8 | 16.729 | 84987 | 8.951 |
| 9 | 17.837 | 19626 | 2.067 |
| Totals | | 949435 | 100 |

Example 18

Procedure for Comparing Stability of Aripiprazole in a SBE-CD Composition and a Fractionated SBE-CD Composition Individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to stabilize aripiprazole. Aqueous solutions of aripiprazole (concentration of 7.5 mg/mL) and the individual SBE-CD compositions (concentration of 150 mg/mL) can be prepared. An aqueous solution of aripiprazole (concentration of 7.5 mg/mL) and the unfractionated SBE-CD composition (concentration of 150 mg/mL) can also be prepared.

Tartaric acid can be dissolved in water and then can be added to the solutions containing aripriprazole and the individual SBE-CD compositions and the solution containing aripiprazole and the unfractionated SBE-CD composition. The mixture can be stirred for about an hour and heated before sterilely filtering the solution. Individual solution samples can be placed into a stability chamber at 50° C. for up to 6 months. After 6 months, individual solution samples can be tested using analytical HPLC and the results from the individual fractionated SBE-CD compositions can be compared to the results from the unfractionated SBE-CD composition.

Example 19

Procedure for Comparing the Ability of a SBE-CD Composition and a Fractionated SBE-CD Composition to Reduce Vacuolization in Rats Individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to reduce the extent of vacuolization in rats.

Aqueous solutions of the individual fractionated SBE-CD compositions and the unfractionated SBE-CD composition can be obtained by diluting a 500 mg/mL concentration of the SBE-CD composition with water as needed to achieve a 1500 mg/kg or 3000 mg/kg single dosing in rats. Animals can be sacrificed after 24 hours or 7 days of dosing. Kidney tissue slides can be examined and the results from the individual fractionated SBE-CD compositions can be compared to the results from the unfractionated SBE-CD composition.

Example 20

Procedure for Comparing the Ability of a SBE-CD Composition and a Fractionated SBE-CD Composition to Reduce the Extent of Cytokine Activity Individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to reduce the extent of cytokine activity in in vitro models.

Example 21

Procedure for Comparing the Ability of a SBE-CD Composition and a Fractionated SBE-CD Composition to Reduce Site Injection Irritation Individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to reduce site injection irritation in animal models.

Example 22

Procedure for Comparing the Ability of a SBE-CD Composition and a Fractionated SBE-CD Composition to Reduce the Temperature of Samples During Formulation Individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to reduce the temperature of samples during formulation as measured by calorimetry.

Example 23

Procedure for Comparing Solubility of Budesonide in a SBE-CD Composition and a Fractionated SBE-CD Composition Using the procedure of Example 16, individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to solubilize budesonide.

The samples can be examined by analytical methods including HPLC to determine which fractionated SBE-CD compositions have improved solubility compared to the unfractionated SBE-CD.

Example 24

Procedure for Comparing Stability of Carfilzomib in a SBE-CD Composition and a Fractionated SBE-CD Composition Individual fractionated SBE-CD compositions (having a single degree of substitution of 1, 2, 3, 4, 5, 6, 7, 8, 9, and 10) can be compared to an unfractionated SBE-CD composition (containing a mixture of substituents having a degree of substitution from 1-10) for the ability to stabilize carfilzomib. Aqueous solutions of carfilzomib (concentration of 7.5 mg/mL) and the individual SBE-CD compositions (concentration of 150 mg/mL) can be prepared. An aqueous solution of carfilzomib (concentration of 7.5 mg/mL) and the unfractionated SBE-CD composition (concentration of 150 mg/mL) can also be prepared.

Tartaric acid can be dissolved in water and then can be added to the solutions containing carfilzomib and the individual SBE-CD compositions and the solution containing carfilzomib and the unfractionated SBE-CD composition. The mixture can be stirred for about an hour and heated before sterilely filtering the solution. Individual solution samples can be placed into a stability chamber at 50° C. for up to 6 months. After 6 months, individual solution samples can be tested using analytical HPLC and the results from the individual fractionated SBE-CD compositions can be compared to the results from the unfractionated SBE-CD composition.

CONCLUSION

These examples illustrate possible embodiments of the present invention. While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the appended claims in any way.

All of the various aspects, embodiments, and options described herein can be combined in any and all variations.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A process for preparing a fractionated alkylated cyclodextrin composition comprising an alkylated cyclodextrin, the process comprising:
   (a) preparing a solution comprising an alkylated cyclodextrin composition;
   (b) passing the solution through a reversed phase high performance liquid chromatography system having a stationary phase and a mobile phase; and
   (c) collecting a fractionated alkylated cyclodextrin composition comprising 85% by weight or more alkylated cyclodextrin having a selected single degree of substitution relative to all alkylated cyclodextrin in the composition; wherein the single degree of substitution is 4, 5, 6, 7, 8, 9, 10, 11, or 12;
   wherein the alkylated cyclodextrin is a sulfoalkyl ether cyclodextrin of Formula (II):

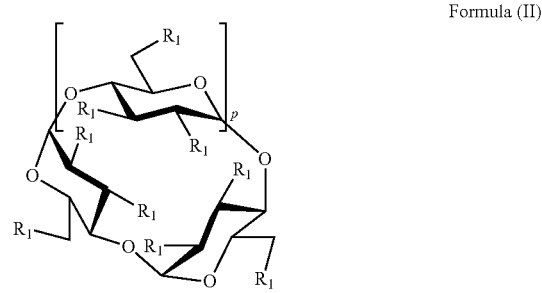

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

2. The process of claim 1, wherein the chromatographic separation system is high performance liquid chromatography.

3. The process of claim 1, wherein the stationary phase is a silica gel column.

4. The process of claim 1, wherein the mobile phase comprises acetonitrile.

5. The process of claim 4, wherein the mobile phase further comprises an ammonium acetate buffer.

6. The process of claim 1, wherein $R_1$ is independently selected at each occurrence from —OH or —O—($C_4$ alkylene)-$SO_3^-$-T, and -T is $Na^+$ at each occurrence.

7. The process of claim 1, further comprising combining the fractionated alkylated cyclodextrin composition with one or more excipients.

8. The process of claim 1, further comprising combining the fractionated alkylated cyclodextrin composition with an active agent.

* * * * *